(12) United States Patent
Korolev et al.

(10) Patent No.: US 8,686,138 B2
(45) Date of Patent: Apr. 1, 2014

(54) HETEROLEPTIC PYRROLECARBALDIMINE PRECURSORS

(75) Inventors: Andrey V. Korolev, Newark, DE (US); Clément Lansalot-Matras, Tsukuba (JP)

(73) Assignee: American Air Liquide, Inc., Fremont, CA (US)

( * ) Notice: Subject to any disclaimer, the term of this patent is extended or adjusted under 35 U.S.C. 154(b) by 5 days.

(21) Appl. No.: 13/341,251

(22) Filed: Dec. 30, 2011

(65) Prior Publication Data
US 2013/0023670 A1    Jan. 24, 2013

Related U.S. Application Data

(60) Provisional application No. 61/510,604, filed on Jul. 22, 2011.

(51) Int. Cl.
*C07F 15/00* (2006.01)
*C07F 17/02* (2006.01)

(52) U.S. Cl.
USPC ......................................... 544/225; 548/108

(58) Field of Classification Search
USPC ......................................... 544/225; 548/108
See application file for complete search history.

(56) References Cited

U.S. PATENT DOCUMENTS

| | | | |
|---|---|---|---|
| 2005/0227007 | A1 | 10/2005 | Bradley et al. |
| 2005/0240028 | A1 | 10/2005 | Grushin |
| 2006/0063898 | A1 | 3/2006 | Inoue et al. |
| 2008/0241575 | A1 | 10/2008 | Lavoie et al. |
| 2008/0305260 | A1 | 12/2008 | Shenai-Khatkhate et al. |
| 2009/0205968 | A1 | 8/2009 | Thompson et al. |
| 2009/0208637 | A1 | 8/2009 | Chen et al. |
| 2010/0119406 | A1 | 5/2010 | Dussarrat et al. |

FOREIGN PATENT DOCUMENTS

JP    2001 261639    9/2001

OTHER PUBLICATIONS

Donald H. Buckley. NASA Scientific and Technical Publications, Washington DC, Apr. 1976. pp. 1-17.*
Amemiya, Kensuke et al., "High energy aluminum ion implantation using a variable energy radio frequency quadrupole implanter," J. Vac. Sci. Technol., A 16(2), Mar./Apr. 1998, pp. 472-476.
Chakravorty, A. et al., "Identification of the geometrical isomers of some tris-chelate cobalt(III) complexes by nuclear resonance," Inorganic Chemistry, 3 (11), Nov. 1964, pp. 1521-1524.
Costes, J.P. et al., "Geometrical and optical isomers of the nickel(II) complexes of chiral, tetradentate unmixed and mixed Schiff bases: CD and NMR spectroscopic studies," Polyhedron 14 (15/16), 1995, pp. 2179-2187.
Felch, S.B. et al., "Plasma doping for the fabrication of ultra-shallow junctions," Surface Coatings Technology, 156(103) 2002, p. 229-236.
Holm, R.H. et al., "The synthesis, structures, and solution equilibria of bis(pyrrole-2-aldimino)metal(II) complexes," Inorganic Chemistry 5 (4), Apr. 1966, pp. 625-635.
Iverson, C.N. et al., "C—H bond activation by unsymmetrical 2-(N-arylimino)pyrrolide Pt complexes: Geometric effects on reactivity," J. Am. Chem. Soc., 125, 2003, pp. 12674-12675.
Matsui, S. et al., "Efficient ethylene polymerisation catalysis by a cationic benzyl hafnium complex containing pyrrolide-imine ligands," J. Chem. Soc. Dalton Trans. 2002, pp. 4529-4531.
Mehta, P, et al., "Study of mixed ligand complexes of nickel(II), copper(II), palladium(II) and platinum(II) with pyrrole-2 carboxaldehyde and acetylacetone," Journal of the Indian Chemical Society, 61 (7), 1984, pp. 571-572.
Pucci, D. et al., "Unsuspected mesomorphism in 'tail-free'cyclopalladated 3,5-disubstituted-2-(2'-pyridyl)pyrroles," Chem. Commun., 12, 2009, pp. 1550-1552.
Yokoi, H. et al., "Spectroscopic and redox properties of pseudotetrahedral copper(II) complexes. Their relationship to copper proteins," Inorganic Chemistry, 16 (6), 1977, pp. 1341-1349.
Yoshida, Y. et al., "New titanium complexes having two pyrrolide-Imine chelate ligands: Syntheses, structures, and ethylene polymerization behavior," Organometallics, 20, 2001, pp. 4793-4799.
Arnaiz, A. et al., "Synthesis, structural preference and catalytic activity of neutral and cationic methylpalladium(II) complexes containing n-arylpyridine-2-carbaldimine chelating ligands," Collect. Czech. Chem. Commun., vol. 67 (2002), pp. 1200-1214.
Gomes, C.S.B. et al., "Octahedral Co(III) complexes of 2-(phenylimino)pyrrol ligands: Synthesis and structural characterisation," Inorganica Chimica Acta, vol. 367, No. 1, Feb. 28, 2011, pp. 151-157.
Grushin, V.V. et al., "Water as an ideal solvent for the synthesis of easily hydrolyzable compounds: High-yield preparation of 2-pyrrolecarbaldimines and their CVD/ALD-relevant Cu(II) derivatives in $H_2O$," Adv. Synth. Catal. 2004, vol. 346, pp. 1457-1460.
International Search Report and Written Opinion for corresponding PCT/US2012/047711, Feb. 5, 2013.
International Search Report and Written Opinion for related PCT/US2012/047694, Feb. 1, 2013.
International Search Report and Written Opinion for related PCT/US2012/047698, Feb. 1, 2013.

* cited by examiner

*Primary Examiner* — Shawquia Young
(74) *Attorney, Agent, or Firm* — Patricia E. McQueeney

(57) ABSTRACT

Disclosed are precursors having a pyrrolecarbaldiminates ligand and methods of synthesizing the same. The pyrrolecarbaldiminates ligand may be substituted.

19 Claims, No Drawings

HETEROLEPTIC PYRROLECARBALDIMINE PRECURSORS

CROSS-REFERENCE TO RELATED APPLICATIONS

This application claims the benefit of U.S. Provisional Application No. 61/510,604, filed Jul. 22, 2011, the entire contents of which are incorporated herein by reference.

TECHNICAL FIELD

Disclosed are metalloid-containing precursors having the formula (1) or (2):

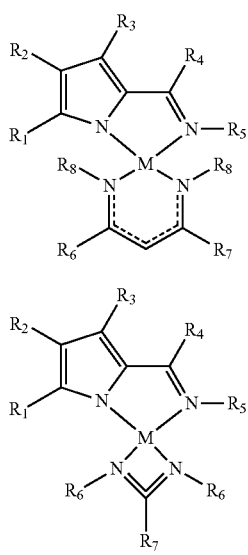

wherein:
M is an element selected from Pd, Pt, or Ru; and
each of $R_1$, $R_2$, $R_3$, $R_4$, $R_5$, $R_6$, $R_7$ and $R_8$ is independently selected from H; a C1-C4 linear, branched, or cyclic alkyl group; a C1-C4 linear, branched, or cyclic alkylsilyl group (mono, bis, or tris alkyl); a C1-C4 linear, branched, or cyclic alkylamino group; or a C1-C4 linear, branched, or cyclic fluoroalkyl group.

Also disclosed are methods of synthesizing the disclosed metalloid-containing precursors and using the disclosed metalloid-containing precursors to deposit metalloid-containing films on one or more substrates via vapor deposition processes.

BACKGROUND

Due to their good stability, chelate complexes of the pyrrole ring systems such as porphyrins have been quite thoroughly studied and characterized. The coordination of a pyrrolecarbaldimine with an alkyl group as a substituent of the imine function has been studied with Cobalt, Nickel, Palladium, Copper (*Inorg. Chem.* 1964, 3, 1521; *Inorg. Chem.* 1966, 5, 625; *Inorg. Chem.* 1977, 16, 1341).

Numerous and important applications have been found for pyrrolecarbaldimine complexes such as post-metallocene catalysis of ethylene polymerization with titanium (*Organometallics*, 2001, 20, 4793) and hafnium (*J. Chem. Soc. Dalton Trans.* 2002, 4529) complexes, and facile C—H activation with platinum derivatives (*J. Am. Chem. Soc.* 2003, 125, 12674).

Heteroleptic complexes including at least one pyrrolecarbaldimine ligand are scarcely reported in the literature. Journal of the Indian Chemical Society (1984), 61(7), 571-2 describes a method of synthesizing heteroleptic nickel, copper, palladium and platinum pyrrolylcarbaldimine/acetylacetonate compounds. Chemical Communications (2009), (12), 1550-1552 describes a method for synthesizing heteroleptic palladium pyrrolylcarbaldimine/fluorinated acetylacetonate. Polyhedron (1995), 14(15/16), 2179-87 describes a method of synthesizing nickel pyrrolylcarbaldimine/ketoiminato where the pyrrolylcarbaldimine and the ketoiminato are bridged.

SUMMARY

Disclosed are metalloid-containing precursors having one of the following

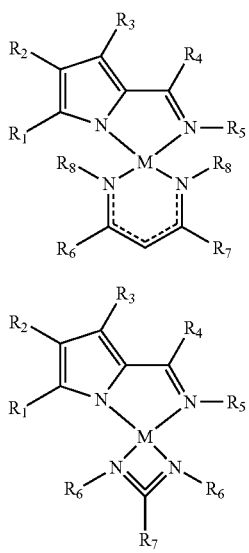

wherein:
M is an element selected from the group consisting of Pd, Pt, and Ru; and
each of $R_1$, $R_2$, $R_3$, $R_4$, $R_5$, $R_6$, $R_7$ and $R_8$ is independently selected from H; a C1-C4 linear, branched, or cyclic alkyl group; a C1-C4 linear, branched, or cyclic alkylsilyl group (mono, bis, or tris alkyl); a C1-C4 linear, branched, or cyclic alkylamino group; or a C1-C4 linear, branched, or cyclic fluoroalkyl group. The disclosed metalloid-containing precursors may further include one or more of the following aspects:
the metalloid-containing precursor being (N,N'-2,4-pentanediketiminate)(pyrrolecarbaldiminate) palladium (II);
the metalloid-containing precursor being (N,N'-2,4-pentanediketiminate)(pyrrolecarbaldmethyliminate) palladium (II);
the metalloid-containing precursor being (N,N'-2,4-pentanediketiminate)(pyrrolecarbaldethyliminate) palladium (II);
the metalloid-containing precursor being (N,N'-2,4-pentanediketiminate)(pyrrolecarbaldisopropyliminate) palladium(II);

the metalloid-containing precursor being (N,N'-2,4-pentanediketiminate)(pyrrolecarbaldpropyliminate) palladium (II);

the metalloid-containing precursor being (N,N'-2,4-pentanediketiminate)(pyrrolecarbaldnbutyliminate) palladium (II);

the metalloid-containing precursor being (N,N'-2,4-pentanediketiminate)(pyrrolecarbaldsecbutyliminate) palladium (II);

the metalloid-containing precursor being (N,N'-2,4-pentanediketiminate)(pyrrolecarbaldisobutyliminate) palladium (II);

the metalloid-containing precursor being (N,N'-2,4-pentanediketiminate)(pyrrolecarbaldtertbutyliminate) palladium (II);

the metalloid-containing precursor being (N,N'-2,4-pentanediketiminate)(pyrrolecarbaldtrimethylsilyliminate) palladium (II);

the metalloid-containing precursor being (N,N'-dimethyl-2,4-pentanediketiminate)(pyrrolecarbaldiminate) palladium(II);

the metalloid-containing precursor being (N,N'-dimethyl-2,4-pentanediketiminate)(pyrrolecarbaldmethyliminate) palladium (II);

the metalloid-containing precursor being (N,N'-dimethyl-2,4-pentanediketiminate)(pyrrolecarbaldethyliminate) palladium (II);

the metalloid-containing precursor being (N,N'-dimethyl-2,4-pentanediketiminate)(pyrrolecarbaldisopropyliminate) palladium(II);

the metalloid-containing precursor being (N,N'-dimethyl-2,4-pentanediketiminate)(pyrrolecarbaldpropyliminate) palladium (II);

the metalloid-containing precursor being (N,N'-dimethyl-2,4-pentanediketiminate)(pyrrolecarbaldnbutyliminate) palladium (II);

the metalloid-containing precursor being (N,N'-dimethyl-2,4-pentanediketiminate)(pyrrolecarbaldsecbutyliminate) palladium (II);

the metalloid-containing precursor being (N,N'-dimethyl-2,4-pentanediketiminate)(pyrrolecarbaldisobutyliminate) palladium (II);

the metalloid-containing precursor being (N,N'-dimethyl-2,4-pentanediketiminate)(pyrrolecarbaldtertbutyliminate) palladium (II);

the metalloid-containing precursor being (N,N'-dimethyl-2,4-pentanediketiminate)(pyrrolecarbaldtrimethylsilyliminate) palladium (II);

the metalloid-containing precursor being (N,N'-diethyl-2,4-pentanediketiminate)(pyrrolecarbaldiminate) palladium(II);

the metalloid-containing precursor being (N,N'-diethyl-2,4-pentanediketiminate)(pyrrolecarbaldmethyliminate) palladium (II);

the metalloid-containing precursor being (N,N'-diethyl-2,4-pentanediketiminate)(pyrrolecarbaldethyliminate) palladium (II);

the metalloid-containing precursor being (N,N'-diethyl-2,4-pentanediketiminate)(pyrrolecarbaldisopropyliminate) palladium(II);

the metalloid-containing precursor being (N,N'-diethyl-2,4-pentanediketiminate)(pyrrolecarbaldpropyliminate) palladium (II);

the metalloid-containing precursor being (N,N'-diethyl-2,4-pentanediketiminate)(pyrrolecarbaldnbutyliminate) palladium (II);

the metalloid-containing precursor being (N,N'-diethyl-2,4-pentanediketiminate)(pyrrolecarbaldsecbutyliminate) palladium (II);

the metalloid-containing precursor being (N,N'-diethyl-2,4-pentanediketiminate)(pyrrolecarbaldisobutyliminate) palladium (II);

the metalloid-containing precursor being (N,N'-diethyl-2,4-pentanediketiminate)(pyrrolecarbaldtertbutyliminate) palladium (II);

the metalloid-containing precursor being (N,N'-diethyl-2,4-pentanediketiminate)(pyrrolecarbaldtrimethylsilyliminate) palladium (II);

the metalloid-containing precursor being (N,N'-diisopropyl-2,4-pentanediketiminate)(pyrrolecarbaldiminate) palladium(II);

the metalloid-containing precursor being (N,N'-diisopropyl-2,4-pentanediketiminate)(pyrrolecarbaldmethyliminate) palladium (II);

the metalloid-containing precursor being (N,N'-diisopropyl-2,4-pentanediketiminate)(pyrrolecarbaldethyliminate) palladium (II);

the metalloid-containing precursor being (N,N'-diisopropyl-2,4-pentanediketiminate)(pyrrolecarbaldisopropyliminate) palladium(II);

the metalloid-containing precursor being (N,N'-diisopropyl-2,4-pentanediketiminate)(pyrrolecarbaldpropyliminate) palladium (II);

the metalloid-containing precursor being (N,N'-diisopropyl-2,4-pentanediketiminate)(pyrrolecarbaldnbutyliminate) palladium (II);

the metalloid-containing precursor being (N,N'-diisopropyl-2,4-pentanediketiminate)(pyrrolecarbaldsecbutyliminate) palladium (II);

the metalloid-containing precursor being (N,N'-diisopropyl-2,4-pentanediketiminate)(pyrrolecarbaldisobutyliminate) palladium (II);

the metalloid-containing precursor being (N,N'-diisopropyl-2,4-pentanediketiminate)(pyrrolecarbaldtertbutyliminate) palladium (II);

the metalloid-containing precursor being (N,N'-diisopropyl-2,4-pentanediketiminate)(pyrrolecarbaldtrimethylsilyliminate)palladium (II);

the metalloid-containing precursor being (N,N'-dipropyl-2,4-pentanediketiminate)(pyrrolecarbaldiminate) palladium(II);

the metalloid-containing precursor being (N,N'-dipropyl-2,4-pentanediketiminate)(pyrrolecarbaldmethyliminate) palladium (II);

the metalloid-containing precursor being (N,N'-dipropyl-2,4-pentanediketiminate)(pyrrolecarbaldethyliminate) palladium (II);

the metalloid-containing precursor being (N,N'-dipropyl-2,4-pentanediketiminate)(pyrrolecarbaldisopropyliminate) palladium(II);

the metalloid-containing precursor being (N,N'-dipropyl-2,4-pentanediketiminate)(pyrrolecarbaldpropyliminate) palladium (II);

the metalloid-containing precursor being (N,N'-dipropyl-2,4-pentanediketiminate)(pyrrolecarbaldnbutyliminate) palladium (II);

the metalloid-containing precursor being (N,N'-dipropyl-2,4-pentanediketiminate)(pyrrolecarbaldsecbutyliminate) palladium (II);

the metalloid-containing precursor being (N,N'-dipropyl-2,4-pentanediketiminate)(pyrrolecarbaldisobutyliminate) palladium (II);

the metalloid-containing precursor being (N,N'-dipropyl-2,4-pentanediketiminate)(pyrrolecarbaldtertbutyliminate) palladium (II);

the metalloid-containing precursor being (N,N'-dipropyl-2,4-pentanediketiminate)(pyrrolecarbaldtrimethylsilyliminate)palladium (II);

the metalloid-containing precursor being (N,N'-di-tert-butyl-2,4-pentanediketiminate)(pyrrolecarbaldiminate) palladium(II);

the metalloid-containing precursor being (N,N'-di-tert-butyl-2,4-pentanediketiminate)(pyrrolecarbaldmethyliminate) palladium (II);

the metalloid-containing precursor being (N,N'-di-tert-butyl-2,4-pentanediketiminate)(pyrrolecarbaldethyliminate) palladium (II);

the metalloid-containing precursor being (N,N'-di-tert-butyl-2,4-pentanediketiminate)(pyrrolecarbaldisopropyliminate) palladium(II);

the metalloid-containing precursor being (N,N'-di-tert-butyl-2,4-pentanediketiminate)(pyrrolecarbaldpropyliminate) palladium (II);

the metalloid-containing precursor being (N,N'-di-tert-butyl-2,4-pentanediketiminate)(pyrrolecarbaldnbutyliminate) palladium (II);

the metalloid-containing precursor being (N,N'-di-tert-butyl-2,4-pentanediketiminate)(pyrrolecarbaldsecbutyliminate) palladium (II);

the metalloid-containing precursor being (N,N'-di-tert-butyl-2,4-pentanediketiminate)(pyrrolecarbaldisobutyliminate) palladium (II);

the metalloid-containing precursor being (N,N'-di-tert-butyl-2,4-pentanediketiminate)(pyrrolecarbaldtertbutyliminate) palladium (II);

the metalloid-containing precursor being (N,N'-di-tert-butyl-2,4-pentanediketiminate)(pyrrolecarbaldtrimethylsilyliminate)palladium (II);

the metalloid-containing precursor being (N,N'-diisopropylformamidinate)(pyrrolecarbaldiminate) palladium (II);

the metalloid-containing precursor being (N,N'-diisopropylformamidinate)(pyrrolecarbaldmethyliminate) palladium (II);

the metalloid-containing precursor being (N,N'-diisopropylformamidinate)(pyrrolecarbaldethyliminate) palladium (II);

the metalloid-containing precursor being (N,N'-diisopropylformamidinate)(pyrrolecarbaldisopropyliminate) palladium(II);

the metalloid-containing precursor being (N,N'-diisopropylformamidinate)(pyrrolecarbaldpropyliminate) palladium (II);

the metalloid-containing precursor being (N,N'-diisopropylformamidinate)(pyrrolecarbaldnbutyliminate) palladium (II);

the metalloid-containing precursor being (N,N'-diisopropylformamidinate)(pyrrolecarbaldsecbutyliminate) palladium (II);

the metalloid-containing precursor being (N,N'-diisopropylformamidinate)(pyrrolecarbaldisobutyliminate) palladium (II);

the metalloid-containing precursor being (N,N'-diisopropylformamidinate)(pyrrolecarbaldtertbutyliminate) palladium(II);

the metalloid-containing precursor being (N,N'-diisopropylformamidinate)(pyrrolecarbaldtrimethylsilyliminate) palladium (II);

the metalloid-containing precursor being (N,N'-diisopropylacetamidinate)(pyrrolecarbaldiminate) palladium (II);

the metalloid-containing precursor being (N,N'-diisopropylacetamidinate)(pyrrolecarbaldmethyliminate) palladium (II);

the metalloid-containing precursor being (N,N'-diisopropylacetamidinate)(pyrrolecarbaldethyliminate) palladium (II);

the metalloid-containing precursor being (N,N'-diisopropylacetamidinate)(pyrrolecarbaldisopropyliminate) palladium(II);

the metalloid-containing precursor being (N,N'-diisopropylacetamidinate)(pyrrolecarbaldpropyliminate) palladium (II);

the metalloid-containing precursor being (N,N'-diisopropylacetamidinate)(pyrrolecarbaldnbutyliminate) palladium (II);

the metalloid-containing precursor being (N,N'-diisopropylacetamidinate)(pyrrolecarbaldsecbutyliminate) palladium (II);

the metalloid-containing precursor being (N,N'-diisopropylacetamidinate)(pyrrolecarbaldisobutyliminate) palladium (II);

the metalloid-containing precursor being (N,N'-diisopropylacetamidinate)(pyrrolecarbaldtertbutyliminate) palladium (II);

the metalloid-containing precursor being (N,N'-diisopropylacetamidinate)(pyrrolecarbaldtrimethylsilyliminate) palladium (II);

the metalloid-containing precursor being (N,N'-diisopropyl-N,N'-dimethylguanidinate)(pyrrolecarbaldiminate) palladium(II);

the metalloid-containing precursor being (N,N'-diisopropyl-N,N'-dimethylguanidinate)(pyrrolecarbaldmethyliminate) palladium (II);

the metalloid-containing precursor being (N,N'-diisopropyl-N,N'-dimethylguanidinate)(pyrrolecarbaldethyliminate) palladium (II);

the metalloid-containing precursor being (N,N'-diisopropyl-N,N'-dimethylguanidinate)(pyrrolecarbaldisopropyliminate) palladium(II);

the metalloid-containing precursor being (N,N'-diisopropyl-N,N'-dimethylguanidinate)(pyrrolecarbaldpropyliminate) palladium (II);

the metalloid-containing precursor being (N,N'-diisopropyl-N,N'-dimethylguanidinate)(pyrrolecarbaldnbutyliminate) palladium (II);

the metalloid-containing precursor being (N,N'-diisopropyl-N,N'-dimethylguanidinate)(pyrrolecarbaldsecbutyliminate) palladium (II);

the metalloid-containing precursor being (N,N'-diisopropyl-N,N'-dimethylguanidinate)(pyrrolecarbaldisobutyliminate) palladium (II);

the metalloid-containing precursor being (N,N'-diisopropyl-N,N'-dimethylguanidinate)(pyrrolecarbaldtertbutyliminate) palladium (II);

the metalloid-containing precursor being (N,N'-diisopropyl-N,N'-dimethylguanidinate)(pyrrolecarbaldtrimethylsilyliminate) palladium (II);

the metalloid-containing precursor being (N,N'-2,4-pentanediketiminate)(pyrrolecarbaldiminate) platinum(II);

the metalloid-containing precursor being (N,N'-2,4-pentanediketiminate)(pyrrolecarbaldmethyliminate) platinum (II);

the metalloid-containing precursor being (N,N'-2,4-pentanediketiminate)(pyrrolecarbaldethyliminate) platinum (II);
the metalloid-containing precursor being (N,N'-2,4-pentanediketiminate)(pyrrolecarbaldisopropyliminate) platinum (II);
the metalloid-containing precursor being (N,N'-2,4-pentanediketiminate)(pyrrolecarbaldpropyliminate) platinum (II);
the metalloid-containing precursor being (N,N'-2,4-pentanediketiminate)(pyrrolecarbaldnbutyliminate) platinum (II);
the metalloid-containing precursor being (N,N'-2,4-pentanediketiminate)(pyrrolecarbaldsecbutyliminate) platinum (II);
the metalloid-containing precursor being (N,N'-2,4-pentanediketiminate)(pyrrolecarbaldisobutyliminate) platinum (II);
the metalloid-containing precursor being (N,N'-2,4-pentanediketiminate)(pyrrolecarbaldtertbutyliminate) platinum (II);
the metalloid-containing precursor being (N,N'-2,4-pentanediketiminate)(pyrrolecarbaldtrimethylsilyliminate) platinum (II);
the metalloid-containing precursor being (N,N'-dimethyl-2,4-pentanediketiminate)(pyrrolecarbaldiminate) platinum (II);
the metalloid-containing precursor being (N,N'-dimethyl-2,4-pentanediketiminate)(pyrrolecarbaldmethyliminate) platinum (II);
the metalloid-containing precursor being (N,N'-dimethyl-2,4-pentanediketiminate)(pyrrolecarbaldethyliminate) platinum (II);
the metalloid-containing precursor being (N,N'-dimethyl-2,4-pentanediketiminate)(pyrrolecarbaldisopropyliminate) platinum (II);
the metalloid-containing precursor being (N,N'-dimethyl-2,4-pentanediketiminate)(pyrrolecarbaldpropyliminate) platinum (II);
the metalloid-containing precursor being (N,N'-dimethyl-2,4-pentanediketiminate)(pyrrolecarbaldnbutyliminate) platinum (II);
the metalloid-containing precursor being (N,N'-dimethyl-2,4-pentanediketiminate)(pyrrolecarbaldsecbutyliminate) platinum (II);
the metalloid-containing precursor being (N,N'-dimethyl-2,4-pentanediketiminate)(pyrrolecarbaldisobutyliminate) platinum (II);
the metalloid-containing precursor being (N,N'-dimethyl-2,4-pentanediketiminate)(pyrrolecarbaldtertbutyliminate) platinum (II);
the metalloid-containing precursor being (N,N'-dimethyl-2,4-pentanediketiminate)(pyrrolecarbaldtrimethylsilyliminate) platinum (II);
the metalloid-containing precursor being (N,N'-diethyl-2,4-pentanediketiminate)(pyrrolecarbaldiminate) platinum (II);
the metalloid-containing precursor being (N,N'-diethyl-2,4-pentanediketiminate)(pyrrolecarbaldmethyliminate) platinum (II);
the metalloid-containing precursor being (N,N'-diethyl-2,4-pentanediketiminate)(pyrrolecarbaldethyliminate) platinum (II);
the metalloid-containing precursor being (N,N'-diethyl-2,4-pentanediketiminate)(pyrrolecarbaldisopropyliminate) platinum (II);
the metalloid-containing precursor being (N,N'-diethyl-2,4-pentanediketiminate)(pyrrolecarbaldpropyliminate) platinum (II);
the metalloid-containing precursor being (N,N'-diethyl-2,4-pentanediketiminate)(pyrrolecarbaldnbutyliminate) platinum (II);
the metalloid-containing precursor being (N,N'-diethyl-2,4-pentanediketiminate)(pyrrolecarbaldsecbutyliminate) platinum (II);
the metalloid-containing precursor being (N,N'-diethyl-2,4-pentanediketiminate)(pyrrolecarbaldisobutyliminate) platinum (II);
the metalloid-containing precursor being (N,N'-diethyl-2,4-pentanediketiminate)(pyrrolecarbaldtertbutyliminate) platinum (II);
the metalloid-containing precursor being (N,N'-diethyl-2,4-pentanediketiminate)(pyrrolecarbaldtrimethylsilyliminate) platinum (II);
the metalloid-containing precursor being (N,N'-diisopropyl-2,4-pentanediketiminate)(pyrrolecarbaldiminate) platinum (II);
the metalloid-containing precursor being (N,N'-diisopropyl-2,4-pentanediketiminate)(pyrrolecarbaldmethyliminate) platinum (II);
the metalloid-containing precursor being (N,N'-diisopropyl-2,4-pentanediketiminate)(pyrrolecarbaldethyliminate) platinum (II);
the metalloid-containing precursor being (N,N'-diisopropyl-2,4-pentanediketiminate)(pyrrolecarbaldisopropyliminate) platinum (II);
the metalloid-containing precursor being (N,N'-diisopropyl-2,4-pentanediketiminate)(pyrrolecarbaldpropyliminate) platinum (II);
the metalloid-containing precursor being (N,N'-diisopropyl-2,4-pentanediketiminate)(pyrrolecarbaldnbutyliminate) platinum (II);
the metalloid-containing precursor being (N,N'-diisopropyl-2,4-pentanediketiminate)(pyrrolecarbaldsecbutyliminate) platinum (II);
the metalloid-containing precursor being (N,N'-diisopropyl-2,4-pentanediketiminate)(pyrrolecarbaldisobutyliminate) platinum (II);
the metalloid-containing precursor being (N,N'-diisopropyl-2,4-pentanediketiminate)(pyrrolecarbaldtertbutyliminate) platinum (II);
the metalloid-containing precursor being (N,N'-diisopropyl-2,4-pentanediketiminate)(pyrrolecarbaldtrimethylsilyliminate) platinum (II);
the metalloid-containing precursor being (N,N'-dipropyl-2,4-pentanediketiminate)(pyrrolecarbaldiminate) platinum (II);
the metalloid-containing precursor being (N,N'-dipropyl-2,4-pentanediketiminate)(pyrrolecarbaldmethyliminate) platinum (II);
the metalloid-containing precursor being (N,N'-dipropyl-2,4-pentanediketiminate)(pyrrolecarbaldethyliminate) platinum (II);
the metalloid-containing precursor being (N,N'-dipropyl-2,4-pentanediketiminate)(pyrrolecarbaldisopropyliminate) platinum (II);
the metalloid-containing precursor being (N,N'-dipropyl-2,4-pentanediketiminate)(pyrrolecarbaldpropyliminate) platinum (II);
the metalloid-containing precursor being (N,N'-dipropyl-2,4-pentanediketiminate)(pyrrolecarbaldnbutyliminate) platinum (II);

the metalloid-containing precursor being (N,N'-dipropyl-2,4-pentanediketiminate)(pyrrolecarbaldsecbutyliminate) platinum (II);

the metalloid-containing precursor being (N,N'-dipropyl-2,4-pentanediketiminate)(pyrrolecarbaldisobutyliminate) platinum (II);

the metalloid-containing precursor being (N,N'-dipropyl-2,4-pentanediketiminate)(pyrrolecarbaldtertbutyliminate) platinum (II);

the metalloid-containing precursor being (N,N'-dipropyl-2,4-pentanediketiminate)(pyrrolecarbaldtrimethylsilyliminate) platinum (II);

the metalloid-containing precursor being (N,N'-di-tert-butyl-2,4-pentanediketiminate)(pyrrolecarbaldiminate) platinum (II);

the metalloid-containing precursor being (N,N'-di-tert-butyl-2,4-pentanediketiminate)(pyrrolecarbaldmethyliminate) platinum (II);

the metalloid-containing precursor being (N,N'-di-tert-butyl-2,4-pentanediketiminate)(pyrrolecarbaldethyliminate) platinum (II);

the metalloid-containing precursor being (N,N'-di-tert-butyl-2,4-pentanediketiminate)(pyrrolecarbaldisopropyliminate) platinum (II);

the metalloid-containing precursor being (N,N'-di-tert-butyl-2,4-pentanediketiminate)(pyrrolecarbaldpropyliminate) platinum (II);

the metalloid-containing precursor being (N,N'-di-tert-butyl-2,4-pentanediketiminate)(pyrrolecarbaldnbutyliminate) platinum (II);

the metalloid-containing precursor being (N,N'-di-tert-butyl-2,4-pentanediketiminate)(pyrrolecarbaldsecbutyliminate) platinum (II);

the metalloid-containing precursor being (N,N'-di-tert-butyl-2,4-pentanediketiminate)(pyrrolecarbaldisobutyliminate) platinum (II);

the metalloid-containing precursor being (N,N'-di-tert-butyl-2,4-pentanediketiminate)(pyrrolecarbaldtertbutyliminate) platinum (II);

the metalloid-containing precursor being (N,N'-di-tert-butyl-2,4-pentanediketiminate)(pyrrolecarbaldtrimethylsilyliminate) platinum (II);

the metalloid-containing precursor being (N,N'-diisopropylformamidinate)(pyrrolecarbaldiminate) platinum (II);

the metalloid-containing precursor being (N,N'-diisopropylformamidinate)(pyrrolecarbaldmethyliminate) platinum (II);

the metalloid-containing precursor being (N,N'-diisopropylformamidinate)(pyrrolecarbaldethyliminate) platinum (II);

the metalloid-containing precursor being (N,N'-diisopropylformamidinate)(pyrrolecarbaldisopropyliminate) platinum (II);

the metalloid-containing precursor being (N,N'-diisopropylformamidinate)(pyrrolecarbaldpropyliminate) platinum (II);

the metalloid-containing precursor being (N,N'-diisopropylformamidinate)(pyrrolecarbaldnbutyliminate) platinum (II);

the metalloid-containing precursor being (N,N'-diisopropylformamidinate)(pyrrolecarbaldsecbutyliminate) platinum (II);

the metalloid-containing precursor being (N,N'-diisopropylformamidinate)(pyrrolecarbaldisobutyliminate) platinum (II);

the metalloid-containing precursor being (N,N'-diisopropylformamidinate)(pyrrolecarbaldtertbutyliminate) platinum (II);

the metalloid-containing precursor being (N,N'-diisopropylformamidinate)(pyrrolecarbaldtrimethylsilyliminate) platinum (II);

the metalloid-containing precursor being (N,N'-diisopropylacetamidinate)(pyrrolecarbaldiminate) platinum (II);

the metalloid-containing precursor being (N,N'-diisopropylacetamidinate)(pyrrolecarbaldmethyliminate) platinum (II);

the metalloid-containing precursor being (N,N'-diisopropylacetamidinate)(pyrrolecarbaldethyliminate) platinum (II);

the metalloid-containing precursor being (N,N'-diisopropylacetamidinate)(pyrrolecarbaldisopropyliminate) platinum (II);

the metalloid-containing precursor being (N,N'-diisopropylacetamidinate)(pyrrolecarbaldpropyliminate) platinum (II);

the metalloid-containing precursor being (N,N'-diisopropylacetamidinate)(pyrrolecarbaldnbutyliminate) platinum (II);

the metalloid-containing precursor being (N,N'-diisopropylacetamidinate)(pyrrolecarbaldsecbutyliminate) platinum (II);

the metalloid-containing precursor being (N,N'-diisopropylacetamidinate)(pyrrolecarbaldisobutyliminate) platinum (II);

the metalloid-containing precursor being (N,N'-diisopropylacetamidinate)(pyrrolecarbaldtertbutyliminate) platinum (II);

the metalloid-containing precursor being (N,N'-diisopropylacetamidinate)(pyrrolecarbaldtrimethylsilyliminate) platinum (II);

the metalloid-containing precursor being (N,N'-diisopropyl-N,N'-dimethylguanidinate)(pyrrolecarbaldiminate) platinum (II);

the metalloid-containing precursor being (N,N'-diisopropyl-N,N'-dimethylguanidinate)(pyrrolecarbaldmethyliminate) platinum (II);

the metalloid-containing precursor being (N,N'-diisopropyl-N,N'-dimethylguanidinate)(pyrrolecarbaldethyliminate) platinum (II);

the metalloid-containing precursor being (N,N'-diisopropyl-N,N'-dimethylguanidinate)(pyrrolecarbaldisopropyliminate) platinum (II);

the metalloid-containing precursor being (N,N'-diisopropyl-N,N'-dimethylguanidinate)(pyrrolecarbaldpropyliminate) platinum (II);

the metalloid-containing precursor being (N,N'-diisopropyl-N,N'-dimethylguanidinate)(pyrrolecarbaldnbutyliminate) platinum (II);

the metalloid-containing precursor being (N,N'-diisopropyl-N,N'-dimethylguanidinate)(pyrrolecarbaldsecbutyliminate) platinum (II);

the metalloid-containing precursor being (N,N'-diisopropyl-N,N'-dimethylguanidinate)(pyrrolecarbaldisobutyliminate) platinum (II);

the metalloid-containing precursor being (N,N'-diisopropyl-N,N'-dimethylguanidinate)(pyrrolecarbaldtertbutyliminate) platinum (II);

the metalloid-containing precursor being (N,N'-diisopropyl-N,N'-dimethylguanidinate)(pyrrolecarbaldtrimethylsilyliminate) platinum (II);

the metalloid-containing precursor being (N,N'-2,4-pentanediketiminate)(pyrrolecarbaldiminate) ruthenium (II);

the metalloid-containing precursor being (N,N'-2,4-pentanediketiminate)(pyrrolecarbaldmethyliminate) ruthenium (II);

the metalloid-containing precursor being (N,N'-2,4-pentanediketiminate)(pyrrolecarbaldethyliminate) ruthenium (II);

the metalloid-containing precursor being (N,N'-2,4-pentanediketiminate)(pyrrolecarbaldisopropyliminate) ruthenium (II);

the metalloid-containing precursor being (N,N'-2,4-pentanediketiminate)(pyrrolecarbaldpropyliminate) ruthenium (II);

the metalloid-containing precursor being (N,N'-2,4-pentanediketiminate)(pyrrolecarbaldnbutyliminate) ruthenium (II);

the metalloid-containing precursor being (N,N'-2,4-pentanediketiminate)(pyrrolecarbaldsecbutyliminate) ruthenium (II);

the metalloid-containing precursor being (N,N'-2,4-pentanediketiminate)(pyrrolecarbaldisobutyliminate) ruthenium (II);

the metalloid-containing precursor being (N,N'-2,4-pentanediketiminate)(pyrrolecarbaldtertbutyliminate) ruthenium (II);

the metalloid-containing precursor being (N,N'-2,4-pentanediketiminate)(pyrrolecarbaldtrimethylsilyliminate) ruthenium (II);

the metalloid-containing precursor being (N,N'-dimethyl-2,4-pentanediketiminate)(pyrrolecarbaldiminate) ruthenium (II);

the metalloid-containing precursor being (N,N'-dimethyl-2,4-pentanediketiminate)(pyrrolecarbaldmethyliminate) ruthenium (II);

the metalloid-containing precursor being (N,N'-dimethyl-2,4-pentanediketiminate)(pyrrolecarbaldethyliminate) ruthenium (II);

the metalloid-containing precursor being (N,N'-dimethyl-2,4-pentanediketiminate)(pyrrolecarbaldisopropyliminate) ruthenium (II);

the metalloid-containing precursor being (N,N'-dimethyl-2,4-pentanediketiminate)(pyrrolecarbaldpropyliminate) ruthenium (II);

the metalloid-containing precursor being (N,N'-dimethyl-2,4-pentanediketiminate)(pyrrolecarbaldnbutyliminate) ruthenium (II);

the metalloid-containing precursor being (N,N'-dimethyl-2,4-pentanediketiminate)(pyrrolecarbaldsecbutyliminate) ruthenium (II);

the metalloid-containing precursor being (N,N'-dimethyl-2,4-pentanediketiminate)(pyrrolecarbaldisobutyliminate) ruthenium (II);

the metalloid-containing precursor being (N,N'-dimethyl-2,4-pentanediketiminate)(pyrrolecarbaldtertbutyliminate) ruthenium (II);

the metalloid-containing precursor being (N,N'-dimethyl-2,4-pentanediketiminate)(pyrrolecarbaldtrimethylsilyliminate) ruthenium (II);

the metalloid-containing precursor being (N,N'-diethyl-2,4-pentanediketiminate)(pyrrolecarbaldiminate) ruthenium (II);

the metalloid-containing precursor being (N,N'-diethyl-2,4-pentanediketiminate)(pyrrolecarbaldmethyliminate) ruthenium (II);

the metalloid-containing precursor being (N,N'-diethyl-2,4-pentanediketiminate)(pyrrolecarbaldethyliminate) ruthenium (II);

the metalloid-containing precursor being (N,N'-diethyl-2,4-pentanediketiminate)(pyrrolecarbaldisopropyliminate) ruthenium (II);

the metalloid-containing precursor being (N,N'-diethyl-2,4-pentanediketiminate)(pyrrolecarbaldpropyliminate) ruthenium (II);

the metalloid-containing precursor being (N,N'-diethyl-2,4-pentanediketiminate)(pyrrolecarbaldnbutyliminate) ruthenium (II);

the metalloid-containing precursor being (N,N'-diethyl-2,4-pentanediketiminate)(pyrrolecarbaldsecbutyliminate) ruthenium (II);

the metalloid-containing precursor being (N,N'-diethyl-2,4-pentanediketiminate)(pyrrolecarbaldisobutyliminate) ruthenium (II);

the metalloid-containing precursor being (N,N'-diethyl-2,4-pentanediketiminate)(pyrrolecarbaldtertbutyliminate) ruthenium (II);

the metalloid-containing precursor being (N,N'-diethyl-2,4-pentanediketiminate)(pyrrolecarbaldtrimethylsilyliminate) ruthenium (II);

the metalloid-containing precursor being (N,N'-diisopropyl-2,4-pentanediketiminate)(pyrrolecarbaldiminate) ruthenium (II);

the metalloid-containing precursor being (N,N'-diisopropyl-2,4-pentanediketiminate)(pyrrolecarbaldmethyliminate) ruthenium (II);

the metalloid-containing precursor being (N,N'-diisopropyl-2,4-pentanediketiminate)(pyrrolecarbaldethyliminate) ruthenium (II);

the metalloid-containing precursor being (N,N'-diisopropyl-2,4-pentanediketiminate)(pyrrolecarbaldisopropyliminate) ruthenium (II);

the metalloid-containing precursor being (N,N'-diisopropyl-2,4-pentanediketiminate)(pyrrolecarbaldpropyliminate) ruthenium (II);

the metalloid-containing precursor being (N,N'-diisopropyl-2,4-pentanediketiminate)(pyrrolecarbaldnbutyliminate) ruthenium (II);

the metalloid-containing precursor being (N,N'-diisopropyl-2,4-pentanediketiminate)(pyrrolecarbaldsecbutyliminate) ruthenium (II);

the metalloid-containing precursor being (N,N'-diisopropyl-2,4-pentanediketiminate)(pyrrolecarbaldisobutyliminate) ruthenium (II);

the metalloid-containing precursor being (N,N'-diisopropyl-2,4-pentanediketiminate)(pyrrolecarbaldtertbutyliminate) ruthenium (II);

the metalloid-containing precursor being (N,N'-diisopropyl-2,4-pentanediketiminate)(pyrrolecarbaldtrimethylsilyliminate) ruthenium (II);

the metalloid-containing precursor being (N,N'-dipropyl-2,4-pentanediketiminate)(pyrrolecarbaldiminate) ruthenium (II);

the metalloid-containing precursor being (N,N'-dipropyl-2,4-pentanediketiminate)(pyrrolecarbaldmethyliminate) ruthenium (II);

the metalloid-containing precursor being (N,N'-dipropyl-2,4-pentanediketiminate)(pyrrolecarbaldethyliminate) ruthenium (II);

the metalloid-containing precursor being (N,N'-dipropyl-2,4-pentanediketiminate)(pyrrolecarbaldisopropyliminate) ruthenium (II);

the metalloid-containing precursor being (N,N'-dipropyl-2,4-pentanediketiminate)(pyrrolecarbaldpropyliminate) ruthenium (II);

the metalloid-containing precursor being (N,N'-dipropyl-2,4-pentanediketiminate)(pyrrolecarbaldnbutyliminate) ruthenium (II);

the metalloid-containing precursor being (N,N'-dipropyl-2,4-pentanediketiminate)(pyrrolecarbaldsecbutyliminate) ruthenium (II);

the metalloid-containing precursor being (N,N'-dipropyl-2,4-pentanediketiminate)(pyrrolecarbaldisobutyliminate) ruthenium (II);

the metalloid-containing precursor being (N,N'-dipropyl-2,4-pentanediketiminate)(pyrrolecarbaldtertbutyliminate) ruthenium (II);

the metalloid-containing precursor being (N,N'-dipropyl-2,4-pentanediketiminate)(pyrrolecarbaldtrimethylsilyliminate) ruthenium (II);

the metalloid-containing precursor being (N,N'-di-tert-butyl-2,4-pentanediketiminate)(pyrrolecarbaldiminate) ruthenium (II);

the metalloid-containing precursor being (N,N'-di-tert-butyl-2,4-pentanediketiminate)(pyrrolecarbaldmethyliminate) ruthenium (II);

the metalloid-containing precursor being (N,N'-di-tert-butyl-2,4-pentanediketiminate)(pyrrolecarbaldethyliminate) ruthenium (II);

the metalloid-containing precursor being (N,N'-di-tert-butyl-2,4-pentanediketiminate)(pyrrolecarbaldisopropyliminate) ruthenium (II);

the metalloid-containing precursor being (N,N'-di-tert-butyl-2,4-pentanediketiminate)(pyrrolecarbaldpropyliminate) ruthenium (II);

the metalloid-containing precursor being (N,N'-di-tert-butyl-2,4-pentanediketiminate)(pyrrolecarbaldnbutyliminate) ruthenium (II);

the metalloid-containing precursor being (N,N'-di-tert-butyl-2,4-pentanediketiminate)(pyrrolecarbaldsecbutyliminate) ruthenium (II);

the metalloid-containing precursor being (N,N'-di-tert-butyl-2,4-pentanediketiminate)(pyrrolecarbaldisobutyliminate) ruthenium (II);

the metalloid-containing precursor being (N,N'-di-tert-butyl-2,4-pentanediketiminate)(pyrrolecarbaldtertbutyliminate) ruthenium (II);

the metalloid-containing precursor being (N,N'-di-tert-butyl-2,4-pentanediketiminate)(pyrrolecarbaldtrimethylsilyliminate) ruthenium (II);

the metalloid-containing precursor being (N,N'-diisopropylformamidinate)(pyrrolecarbaldiminate) ruthenium (II);

the metalloid-containing precursor being (N,N'-diisopropylformamidinate)(pyrrolecarbaldmethyliminate) ruthenium (II);

the metalloid-containing precursor being (N,N'-diisopropylformamidinate)(pyrrolecarbaldethyliminate) ruthenium (II);

the metalloid-containing precursor being (N,N'-diisopropylformamidinate)(pyrrolecarbaldisopropyliminate) ruthenium (II);

the metalloid-containing precursor being (N,N'-diisopropylformamidinate)(pyrrolecarbaldpropyliminate) ruthenium (II);

the metalloid-containing precursor being (N,N'-diisopropylformamidinate)(pyrrolecarbaldnbutyliminate) ruthenium (II);

the metalloid-containing precursor being (N,N'-diisopropylformamidinate)(pyrrolecarbaldsecbutyliminate) ruthenium (II);

the metalloid-containing precursor being (N,N'-diisopropylformamidinate)(pyrrolecarbaldisobutyliminate) ruthenium (II);

the metalloid-containing precursor being (N,N'-diisopropylformamidinate)(pyrrolecarbaldtertbutyliminate) ruthenium (II);

the metalloid-containing precursor being (N,N'-diisopropylformamidinate)(pyrrolecarbaldtrimethylsilyliminate) ruthenium (II);

the metalloid-containing precursor being (N,N'-diisopropylacetamidinate)(pyrrolecarbaldiminate) ruthenium (II);

the metalloid-containing precursor being (N,N'-diisopropylacetamidinate)(pyrrolecarbaldmethyliminate) ruthenium (II);

the metalloid-containing precursor being (N,N'-diisopropylacetamidinate)(pyrrolecarbaldethyliminate) ruthenium (II);

the metalloid-containing precursor being (N,N'-diisopropylacetamidinate)(pyrrolecarbaldisopropyliminate) ruthenium (II);

the metalloid-containing precursor being (N,N'-diisopropylacetamidinate)(pyrrolecarbaldpropyliminate) ruthenium (II);

the metalloid-containing precursor being (N,N'-diisopropylacetamidinate)(pyrrolecarbaldnbutyliminate) ruthenium (II);

the metalloid-containing precursor being (N,N'-diisopropylacetamidinate)(pyrrolecarbaldsecbutyliminate) ruthenium (II);

the metalloid-containing precursor being (N,N'-diisopropylacetamidinate)(pyrrolecarbaldisobutyliminate) ruthenium (II);

the metalloid-containing precursor being (N,N'-diisopropylacetamidinate)(pyrrolecarbaldtertbutyliminate) ruthenium (II);

the metalloid-containing precursor being (N,N'-diisopropylacetamidinate)(pyrrolecarbaldtrimethylsilyliminate) ruthenium (II);

the metalloid-containing precursor being (N,N'-diisopropyl-N,N'-dimethylguanidinate)(pyrrolecarbaldiminate) ruthenium (II);

the metalloid-containing precursor being (N,N'-diisopropyl-N,N'-dimethylguanidinate)(pyrrolecarbaldmethyliminate) ruthenium (II);

the metalloid-containing precursor being (N,N'-diisopropyl-N,N'-dimethylguanidinate)(pyrrolecarbaldethyliminate) ruthenium (II);

the metalloid-containing precursor being (N,N'-diisopropyl-N,N'-dimethylguanidinate)(pyrrolecarbaldisopropyliminate) ruthenium (II);

the metalloid-containing precursor being (N,N'-diisopropyl-N,N'-dimethylguanidinate)(pyrrolecarbaldpropyliminate) ruthenium (II);

the metalloid-containing precursor being (N,N'-diisopropyl-N,N'-dimethylguanidinate)(pyrrolecarbaldnbutyliminate) ruthenium (II);

the metalloid-containing precursor being (N,N'-diisopropyl-N,N'-dimethylguanidinate)(pyrrolecarbaldsecbutyliminate) ruthenium (II);

the metalloid-containing precursor being (N,N'-diisopropyl-N,N'-dimethylguanidinate)(pyrrolecarbaldisobutyliminate) ruthenium (II);

the metalloid-containing precursor being (N,N'-diisopropyl-N,N'-dimethylguanidinate)(pyrrolecarbaldtertbutyliminate) ruthenium (II); and the metalloid-containing precursor being (N,N'-diisopropyl-N,N'-dimethylguanidinate)(pyrrolecarbaldtrimethylsilyliminate) ruthenium (II).

Also disclosed are processes for the deposition of a metalloid-containing film on a substrate. At least one metalloid-containing precursor is introduced into a reactor having at least one substrate disposed therein. At least part of the metalloid-containing precursor is deposited onto the at least one substrate to form the metalloid-containing film. The at least one metalloid-containing precursor has one of the following formulae:

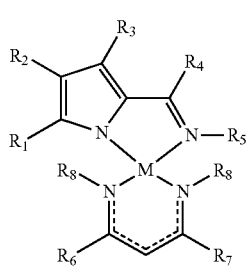

(1)

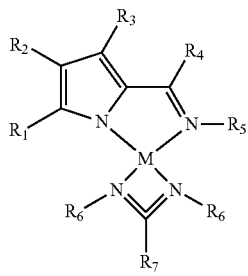

(2)

wherein:
M is an element selected from the group consisting of Pd, Pt, and Ru; and
each of $R_1$, $R_2$, $R_3$, $R_4$, $R_5$, $R_6$, $R_7$ and $R_8$ is independently selected from H; a C1-C4 linear, branched, or cyclic alkyl group; a C1-C4 linear, branched, or cyclic alkylsilyl group (mono, bis, or tris alkyl); a C1-C4 linear, branched, or cyclic alkylamino group; or a C1-C4 linear, branched, or cyclic fluoroalkyl group. The disclosed processes may further include one or more of the following aspects:
introducing at least one reactant into the reactor;
the reactant being selected from the group consisting of $H_2$, $NH_3$, $SiH_4$, $Si_2H_6$, $Si_3H_8$, $SiH_2Me_2$, $SiH_2Et_2$, $N(SiH_3)_3$, hydrogen radicals thereof, and mixtures thereof;
the reactant being selected from the group consisting of: $O_2$, $O_3$, $H_2O$, NO, $N_2O$, oxygen radicals thereof, and mixtures thereof;
the metalloid-containing precursor and the reactant being introduced into the reactor substantially simultaneously;
the reactor being configured for chemical vapor deposition;
the reactor being configured for plasma enhanced chemical vapor deposition;
the metalloid-containing precursor and the reactant being introduced into the chamber sequentially;
the reactor being configured for atomic layer deposition;
the reactor being configured for plasma enhanced atomic layer deposition;
the metalloid-containing precursor being (N,N'-2,4-pentanediketiminate)(pyrrolecarbaldiminate) palladium (II);
the metalloid-containing precursor being (N,N'-2,4-pentanediketiminate)(pyrrolecarbaldmethyliminate) palladium (II);
the metalloid-containing precursor being (N,N'-2,4-pentanediketiminate)(pyrrolecarbaldethyliminate) palladium (II);
the metalloid-containing precursor being (N,N'-2,4-pentanediketiminate)(pyrrolecarbaldisopropyliminate) palladium(II);
the metalloid-containing precursor being (N,N'-2,4-pentanediketiminate)(pyrrolecarbaldpropyliminate) palladium (II);
the metalloid-containing precursor being (N,N'-2,4-pentanediketiminate)(pyrrolecarbaldnbutyliminate) palladium (II);
the metalloid-containing precursor being (N,N'-2,4-pentanediketiminate)(pyrrolecarbaldsecbutyliminate) palladium (II);
the metalloid-containing precursor being (N,N'-2,4-pentanediketiminate)(pyrrolecarbaldisobutyliminate) palladium (II);
the metalloid-containing precursor being (N,N'-2,4-pentanediketiminate)(pyrrolecarbaldtertbutyliminate) palladium (II);
the metalloid-containing precursor being (N,N'-2,4-pentanediketiminate)(pyrrolecarbaldtrimethylsilyliminate) palladium (II);
the metalloid-containing precursor being (N,N'-dimethyl-2,4-pentanediketiminate)(pyrrolecarbaldiminate) palladium(II);
the metalloid-containing precursor being (N,N'-dimethyl-2,4-pentanediketiminate)(pyrrolecarbaldmethyliminate) palladium (II);
the metalloid-containing precursor being (N,N'-dimethyl-2,4-pentanediketiminate)(pyrrolecarbaldethyliminate) palladium (II);
the metalloid-containing precursor being (N,N'-dimethyl-2,4-pentanediketiminate)(pyrrolecarbaldisopropyliminate) palladium(II);
the metalloid-containing precursor being (N,N'-dimethyl-2,4-pentanediketiminate)(pyrrolecarbaldpropyliminate) palladium (II);
the metalloid-containing precursor being (N,N'-dimethyl-2,4-pentanediketiminate)(pyrrolecarbaldnbutyliminate) palladium (II);
the metalloid-containing precursor being (N,N'-dimethyl-2,4-pentanediketiminate)(pyrrolecarbaldsecbutyliminate) palladium (II);
the metalloid-containing precursor being (N,N'-dimethyl-2,4-pentanediketiminate)(pyrrolecarbaldisobutyliminate) palladium (II);
the metalloid-containing precursor being (N,N'-dimethyl-2,4-pentanediketiminate)(pyrrolecarbaldtertbutyliminate) palladium (II);
the metalloid-containing precursor being (N,N'-dimethyl-2,4-pentanediketiminate)(pyrrolecarbaldtrimethylsilyliminate) palladium (II);
the metalloid-containing precursor being (N,N'-diethyl-2,4-pentanediketiminate)(pyrrolecarbaldiminate) palladium(II);

the metalloid-containing precursor being (N,N'-diethyl-2,4-pentanediketiminate)(pyrrolecarbaldmethyliminate) palladium (II);

the metalloid-containing precursor being (N,N'-diethyl-2,4-pentanediketiminate)(pyrrolecarbaldethyliminate) palladium (II);

the metalloid-containing precursor being (N,N'-diethyl-2,4-pentanediketiminate)(pyrrolecarbaldisopropyliminate) palladium(II);

the metalloid-containing precursor being (N,N'-diethyl-2,4-pentanediketiminate)(pyrrolecarbaldpropyliminate) palladium (II);

the metalloid-containing precursor being (N,N'-diethyl-2,4-pentanediketiminate)(pyrrolecarbaldnbutyliminate) palladium (II);

the metalloid-containing precursor being (N,N'-diethyl-2,4-pentanediketiminate)(pyrrolecarbaldsecbutyliminate) palladium (II);

the metalloid-containing precursor being (N,N'-diethyl-2,4-pentanediketiminate)(pyrrolecarbaldisobutyliminate) palladium (II);

the metalloid-containing precursor being (N,N'-diethyl-2,4-pentanediketiminate)(pyrrolecarbaldtertbutyliminate) palladium (II);

the metalloid-containing precursor being (N,N'-diethyl-2,4-pentanediketiminate)(pyrrolecarbaldtrimethylsilyliminate) palladium (II);

the metalloid-containing precursor being (N,N'-diisopropyl-2,4-pentanediketiminate)(pyrrolecarbaldiminate) palladium(II);

the metalloid-containing precursor being (N,N'-diisopropyl-2,4-pentanediketiminate)(pyrrolecarbaldmethyliminate) palladium (II);

the metalloid-containing precursor being (N,N'-diisopropyl-2,4-pentanediketiminate)(pyrrolecarbaldethyliminate) palladium (II);

the metalloid-containing precursor being (N,N'-diisopropyl-2,4-pentanediketiminate)(pyrrolecarbaldisopropyliminate) palladium(II);

the metalloid-containing precursor being (N,N'-diisopropyl-2,4-pentanediketiminate)(pyrrolecarbaldpropyliminate) palladium (II);

the metalloid-containing precursor being (N,N'-diisopropyl-2,4-pentanediketiminate)(pyrrolecarbaldnbutyliminate) palladium (II);

the metalloid-containing precursor being (N,N'-diisopropyl-2,4-pentanediketiminate)(pyrrolecarbaldsecbutyliminate) palladium (II);

the metalloid-containing precursor being (N,N'-diisopropyl-2,4-pentanediketiminate)(pyrrolecarbaldisobutyliminate) palladium (II);

the metalloid-containing precursor being (N,N'-diisopropyl-2,4-pentanediketiminate)(pyrrolecarbaldtertbutyliminate) palladium (II);

the metalloid-containing precursor being (N,N'-diisopropyl-2,4-pentanediketiminate)(pyrrolecarbaldtrimethylsilyliminate)palladium (II);

the metalloid-containing precursor being (N,N'-dipropyl-2,4-pentanediketiminate)(pyrrolecarbaldiminate) palladium(II);

the metalloid-containing precursor being (N,N'-dipropyl-2,4-pentanediketiminate)(pyrrolecarbaldmethyliminate) palladium (II);

the metalloid-containing precursor being (N,N'-dipropyl-2,4-pentanediketiminate)(pyrrolecarbaldethyliminate) palladium (II);

the metalloid-containing precursor being (N,N'-dipropyl-2,4-pentanediketiminate)(pyrrolecarbaldisopropyliminate) palladium(II);

the metalloid-containing precursor being (N,N'-dipropyl-2,4-pentanediketiminate)(pyrrolecarbaldpropyliminate) palladium (II);

the metalloid-containing precursor being (N,N'-dipropyl-2,4-pentanediketiminate)(pyrrolecarbaldnbutyliminate) palladium (II);

the metalloid-containing precursor being (N,N'-dipropyl-2,4-pentanediketiminate)(pyrrolecarbaldsecbutyliminate) palladium (II);

the metalloid-containing precursor being (N,N'-dipropyl-2,4-pentanediketiminate)(pyrrolecarbaldisobutyliminate) palladium (II);

the metalloid-containing precursor being (N,N'-dipropyl-2,4-pentanediketiminate)(pyrrolecarbaldtertbutyliminate) palladium (II);

the metalloid-containing precursor being (N,N'-dipropyl-2,4-pentanediketiminate)(pyrrolecarbaldtrimethylsilyliminate)palladium (II);

the metalloid-containing precursor being (N,N'-di-tert-butyl-2,4-pentanediketiminate)(pyrrolecarbaldiminate) palladium(II);

the metalloid-containing precursor being (N,N'-di-tert-butyl-2,4-pentanediketiminate)(pyrrolecarbaldmethyliminate) palladium (II);

the metalloid-containing precursor being (N,N'-di-tert-butyl-2,4-pentanediketiminate)(pyrrolecarbaldethyliminate) palladium (II);

the metalloid-containing precursor being (N,N'-di-tert-butyl-2,4-pentanediketiminate)(pyrrolecarbaldisopropyliminate) palladium(II);

the metalloid-containing precursor being (N,N'-di-tert-butyl-2,4-pentanediketiminate)(pyrrolecarbaldpropyliminate) palladium (II);

the metalloid-containing precursor being (N,N'-di-tert-butyl-2,4-pentanediketiminate)(pyrrolecarbaldnbutyliminate) palladium (II);

the metalloid-containing precursor being (N,N'-di-tert-butyl-2,4-pentanediketiminate)(pyrrolecarbaldsecbutyliminate) palladium (II);

the metalloid-containing precursor being (N,N'-di-tert-butyl-2,4-pentanediketiminate)(pyrrolecarbaldisobutyliminate) palladium (II);

the metalloid-containing precursor being (N,N'-di-tert-butyl-2,4-pentanediketiminate)(pyrrolecarbaldtertbutyliminate) palladium (II);

the metalloid-containing precursor being (N,N'-di-tert-butyl-2,4-pentanediketiminate)(pyrrolecarbaldtrimethylsilyliminate)palladium (II);

the metalloid-containing precursor being (N,N'-diisopropylformamidinate)(pyrrolecarbaldiminate) palladium (II);

the metalloid-containing precursor being (N,N'-diisopropylformamidinate)(pyrrolecarbaldmethyliminate) palladium (II);

the metalloid-containing precursor being (N,N'-diisopropylformamidinate)(pyrrolecarbaldethyliminate) palladium (II);

the metalloid-containing precursor being (N,N'-diisopropylformamidinate)(pyrrolecarbaldisopropyliminate) palladium(II);

the metalloid-containing precursor being (N,N'-diisopropylformamidinate)(pyrrolecarbaldpropyliminate) palladium (II);

the metalloid-containing precursor being (N,N'-diisopropylformamidinate)(pyrrolecarbaldnbutyliminate) palladium (II);

the metalloid-containing precursor being (N,N'-diisopropylformamidinate)(pyrrolecarbaldsecbutyliminate) palladium (II);

the metalloid-containing precursor being (N,N'-diisopropylformamidinate)(pyrrolecarbaldisobutyliminate) palladium (II);

the metalloid-containing precursor being (N,N'-diisopropylformamidinate)(pyrrolecarbaldtertbutyliminate) palladium (II);

the metalloid-containing precursor being (N,N'-diisopropylformamidinate)(pyrrolecarbaldtrimethylsilyliminate) palladium (II);

the metalloid-containing precursor being (N,N'-diisopropylacetamidinate)(pyrrolecarbaldiminate) palladium (II);

the metalloid-containing precursor being (N,N'-diisopropylacetamidinate)(pyrrolecarbaldmethyliminate) palladium (II);

the metalloid-containing precursor being (N,N'-diisopropylacetamidinate)(pyrrolecarbaldethyliminate) palladium (II);

the metalloid-containing precursor being (N,N'-diisopropylacetamidinate)(pyrrolecarbaldisopropyliminate) palladium(II);

the metalloid-containing precursor being (N,N'-diisopropylacetamidinate)(pyrrolecarbaldpropyliminate) palladium (II);

the metalloid-containing precursor being (N,N'-diisopropylacetamidinate)(pyrrolecarbaldnbutyliminate) palladium (II);

the metalloid-containing precursor being (N,N'-diisopropylacetamidinate)(pyrrolecarbaldsecbutyliminate) palladium (II);

the metalloid-containing precursor being (N,N'-diisopropylacetamidinate)(pyrrolecarbaldisobutyliminate) palladium (II);

the metalloid-containing precursor being (N,N'-diisopropylacetamidinate)(pyrrolecarbaldtertbutyliminate) palladium (II);

the metalloid-containing precursor being (N,N'-diisopropylacetamidinate)(pyrrolecarbaldtrimethylsilyliminate) palladium (II);

the metalloid-containing precursor being (N,N'-diisopropyl-N,N'-dimethylguanidinate)(pyrrolecarbaldiminate) palladium(II);

the metalloid-containing precursor being (N,N'-diisopropyl-N,N'-dimethylguanidinate)(pyrrolecarbaldmethyliminate) palladium (II);

the metalloid-containing precursor being (N,N'-diisopropyl-N,N'-dimethylguanidinate)(pyrrolecarbaldethyliminate) palladium (II);

the metalloid-containing precursor being (N,N'-diisopropyl-N,N'-dimethylguanidinate)(pyrrolecarbaldisopropyliminate) palladium(II);

the metalloid-containing precursor being (N,N'-diisopropyl-N,N'-dimethylguanidinate)(pyrrolecarbaldpropyliminate) palladium (II);

the metalloid-containing precursor being (N,N'-diisopropyl-N,N'-dimethylguanidinate)(pyrrolecarbaldnbutyliminate) palladium (II);

the metalloid-containing precursor being (N,N'-diisopropyl-N,N'-dimethylguanidinate)(pyrrolecarbaldsecbutyliminate) palladium (II);

the metalloid-containing precursor being (N,N'-diisopropyl-N,N'-dimethylguanidinate)(pyrrolecarbaldisobutyliminate) palladium (II);

the metalloid-containing precursor being (N,N'-diisopropyl-N,N'-dimethylguanidinate)(pyrrolecarbaldtertbutyliminate) palladium (II);

the metalloid-containing precursor being (N,N'-diisopropyl-N,N'-dimethylguanidinate)(pyrrolecarbaldtrimethylsilyliminate) palladium (II);

the metalloid-containing precursor being (N,N'-2,4-pentanediketiminate)(pyrrolecarbaldiminate) platinum(II);

the metalloid-containing precursor being (N,N'-2,4-pentanediketiminate)(pyrrolecarbaldmethyliminate) platinum (II);

the metalloid-containing precursor being (N,N'-2,4-pentanediketiminate)(pyrrolecarbaldethyliminate) platinum (II);

the metalloid-containing precursor being (N,N'-2,4-pentanediketiminate)(pyrrolecarbaldisopropyliminate) platinum (II);

the metalloid-containing precursor being (N,N'-2,4-pentanediketiminate)(pyrrolecarbaldpropyliminate) platinum (II);

the metalloid-containing precursor being (N,N'-2,4-pentanediketiminate)(pyrrolecarbaldnbutyliminate) platinum (II);

the metalloid-containing precursor being (N,N'-2,4-pentanediketiminate)(pyrrolecarbaldsecbutyliminate) platinum (II);

the metalloid-containing precursor being (N,N'-2,4-pentanediketiminate)(pyrrolecarbaldisobutyliminate) platinum (II);

the metalloid-containing precursor being (N,N'-2,4-pentanediketiminate)(pyrrolecarbaldtertbutyliminate) platinum (II);

the metalloid-containing precursor being (N,N'-2,4-pentanediketiminate)(pyrrolecarbaldtrimethylsilyliminate) platinum (II);

the metalloid-containing precursor being (N,N'-dimethyl-2,4-pentanediketiminate)(pyrrolecarbaldiminate) platinum (II);

the metalloid-containing precursor being (N,N'-dimethyl-2,4-pentanediketiminate)(pyrrolecarbaldmethyliminate) platinum (II);

the metalloid-containing precursor being (N,N'-dimethyl-2,4-pentanediketiminate)(pyrrolecarbaldethyliminate) platinum (II);

the metalloid-containing precursor being (N,N'-dimethyl-2,4-pentanediketiminate)(pyrrolecarbaldisopropyliminate) platinum (II);

the metalloid-containing precursor being (N,N'-dimethyl-2,4-pentanediketiminate)(pyrrolecarbaldpropyliminate) platinum (II);

the metalloid-containing precursor being (N,N'-dimethyl-2,4-pentanediketiminate)(pyrrolecarbaldnbutyliminate) platinum (II);

the metalloid-containing precursor being (N,N'-dimethyl-2,4-pentanediketiminate)(pyrrolecarbaldsecbutyliminate) platinum (II);

the metalloid-containing precursor being (N,N'-dimethyl-2,4-pentanediketiminate)(pyrrolecarbaldisobutyliminate) platinum (II);

the metalloid-containing precursor being (N,N'-dimethyl-2,4-pentanediketiminate)(pyrrolecarbaldtertbutyliminate) platinum (II);

the metalloid-containing precursor being (N,N'-dimethyl-2,4-pentanediketiminate)(pyrrolecarbaldtrimethylsilyliminate) platinum (II);

the metalloid-containing precursor being (N,N'-diethyl-2,4-pentanediketiminate)(pyrrolecarbaldiminate) platinum (II);

the metalloid-containing precursor being (N,N'-diethyl-2,4-pentanediketiminate)(pyrrolecarbaldmethyliminate) platinum (II);

the metalloid-containing precursor being (N,N'-diethyl-2,4-pentanediketiminate)(pyrrolecarbaldethyliminate) platinum (II);

the metalloid-containing precursor being (N,N'-diethyl-2,4-pentanediketiminate)(pyrrolecarbaldisopropyliminate) platinum (II);

the metalloid-containing precursor being (N,N'-diethyl-2,4-pentanediketiminate)(pyrrolecarbaldpropyliminate) platinum (II);

the metalloid-containing precursor being (N,N'-diethyl-2,4-pentanediketiminate)(pyrrolecarbaldnbutyliminate) platinum (II);

the metalloid-containing precursor being (N,N'-diethyl-2,4-pentanediketiminate)(pyrrolecarbaldsecbutyliminate) platinum (II);

the metalloid-containing precursor being (N,N'-diethyl-2,4-pentanediketiminate)(pyrrolecarbaldisobutyliminate) platinum (II);

the metalloid-containing precursor being (N,N'-diethyl-2,4-pentanediketiminate)(pyrrolecarbaldtertbutyliminate) platinum (II);

the metalloid-containing precursor being (N,N'-diethyl-2,4-pentanediketiminate)(pyrrolecarbaldtrimethylsilyliminate) platinum (II);

the metalloid-containing precursor being (N,N'-diisopropyl-2,4-pentanediketiminate)(pyrrolecarbaldiminate) platinum (II);

the metalloid-containing precursor being (N,N'-diisopropyl-2,4-pentanediketiminate)(pyrrolecarbaldmethyliminate) platinum (II);

the metalloid-containing precursor being (N,N'-diisopropyl-2,4-pentanediketiminate)(pyrrolecarbaldethyliminate) platinum (II);

the metalloid-containing precursor being (N,N'-diisopropyl-2,4-pentanediketiminate)(pyrrolecarbaldisopropyliminate) platinum (II);

the metalloid-containing precursor being (N,N'-diisopropyl-2,4-pentanediketiminate)(pyrrolecarbaldpropyliminate) platinum (II);

the metalloid-containing precursor being (N,N'-diisopropyl-2,4-pentanediketiminate)(pyrrolecarbaldnbutyliminate) platinum (II);

the metalloid-containing precursor being (N,N'-diisopropyl-2,4-pentanediketiminate)(pyrrolecarbaldsecbutyliminate) platinum (II);

the metalloid-containing precursor being (N,N'-diisopropyl-2,4-pentanediketiminate)(pyrrolecarbaldisobutyliminate) platinum (II);

the metalloid-containing precursor being (N,N'-diisopropyl-2,4-pentanediketiminate)(pyrrolecarbaldtertbutyliminate) platinum (II);

the metalloid-containing precursor being (N,N'-diisopropyl-2,4-pentanediketiminate)(pyrrolecarbaldtrimethylsilyliminate) platinum (II);

the metalloid-containing precursor being (N,N'-dipropyl-2,4-pentanediketiminate)(pyrrolecarbaldiminate) platinum (II);

the metalloid-containing precursor being (N,N'-dipropyl-2,4-pentanediketiminate)(pyrrolecarbaldmethyliminate) platinum (II);

the metalloid-containing precursor being (N,N'-dipropyl-2,4-pentanediketiminate)(pyrrolecarbaldethyliminate) platinum (II);

the metalloid-containing precursor being (N,N'-dipropyl-2,4-pentanediketiminate)(pyrrolecarbaldisopropyliminate) platinum (II);

the metalloid-containing precursor being (N,N'-dipropyl-2,4-pentanediketiminate)(pyrrolecarbaldpropyliminate) platinum (II);

the metalloid-containing precursor being (N,N'-dipropyl-2,4-pentanediketiminate)(pyrrolecarbaldnbutyliminate) platinum (II);

the metalloid-containing precursor being (N,N'-dipropyl-2,4-pentanediketiminate)(pyrrolecarbaldsecbutyliminate) platinum (II);

the metalloid-containing precursor being (N,N'-dipropyl-2,4-pentanediketiminate)(pyrrolecarbaldisobutyliminate) platinum (II);

the metalloid-containing precursor being (N,N'-dipropyl-2,4-pentanediketiminate)(pyrrolecarbaldtertbutyliminate) platinum (II);

the metalloid-containing precursor being (N,N'-dipropyl-2,4-pentanediketiminate)(pyrrolecarbaldtrimethylsilyliminate) platinum (II);

the metalloid-containing precursor being (N,N'-di-tert-butyl-2,4-pentanediketiminate)(pyrrolecarbaldiminate) platinum (II);

the metalloid-containing precursor being (N,N'-di-tert-butyl-2,4-pentanediketiminate)(pyrrolecarbaldmethyliminate) platinum (II);

the metalloid-containing precursor being (N,N'-di-tert-butyl-2,4-pentanediketiminate)(pyrrolecarbaldethyliminate) platinum (II);

the metalloid-containing precursor being (N,N'-di-tert-butyl-2,4-pentanediketiminate)(pyrrolecarbaldisopropyliminate) platinum (II);

the metalloid-containing precursor being (N,N'-di-tert-butyl-2,4-pentanediketiminate)(pyrrolecarbaldpropyliminate) platinum (II);

the metalloid-containing precursor being (N,N'-di-tert-butyl-2,4-pentanediketiminate)(pyrrolecarbaldnbutyliminate) platinum (II);

the metalloid-containing precursor being (N,N'-di-tert-butyl-2,4-pentanediketiminate)(pyrrolecarbaldsecbutyliminate) platinum (II);

the metalloid-containing precursor being (N,N'-di-tert-butyl-2,4-pentanediketiminate)(pyrrolecarbaldisobutyliminate) platinum (II);

the metalloid-containing precursor being (N,N'-di-tert-butyl-2,4-pentanediketiminate)(pyrrolecarbaldtertbutyliminate) platinum (II);

the metalloid-containing precursor being (N,N'-di-tert-butyl-2,4-pentanediketiminate)(pyrrolecarbaldtrimethylsilyliminate) platinum (II);

the metalloid-containing precursor being (N,N'-diisopropylformamidinate)(pyrrolecarbaldiminate) platinum (II);

the metalloid-containing precursor being (N,N'-diisopropylformamidinate)(pyrrolecarbaldmethyliminate) platinum (II);

the metalloid-containing precursor being (N,N'-diisopropylformamidinate)(pyrrolecarbaldethyliminate) platinum (II);

the metalloid-containing precursor being (N,N'-diisopropylformamidinate)(pyrrolecarbaldisopropyliminate) platinum (II);

the metalloid-containing precursor being (N,N'-diisopropylformamidinate)(pyrrolecarbaldpropyliminate) platinum (II);

the metalloid-containing precursor being (N,N'-diisopropylformamidinate)(pyrrolecarbaldnbutyliminate) platinum (II);

the metalloid-containing precursor being (N,N'-diisopropylformamidinate)(pyrrolecarbaldsecbutyliminate) platinum (II);

the metalloid-containing precursor being (N,N'-diisopropylformamidinate)(pyrrolecarbaldisobutyliminate) platinum (II);

the metalloid-containing precursor being (N,N'-diisopropylformamidinate)(pyrrolecarbaldtertbutyliminate) platinum (II);

the metalloid-containing precursor being (N,N'-diisopropylformamidinate)(pyrrolecarbaldtrimethylsilyliminate) platinum (II);

the metalloid-containing precursor being (N,N'-diisopropylacetamidinate)(pyrrolecarbaldiminate) platinum (II);

the metalloid-containing precursor being (N,N'-diisopropylacetamidinate)(pyrrolecarbaldmethyliminate) platinum (II);

the metalloid-containing precursor being (N,N'-diisopropylacetamidinate)(pyrrolecarbaldethyliminate) platinum (II);

the metalloid-containing precursor being (N,N'-diisopropylacetamidinate)(pyrrolecarbaldisopropyliminate) platinum (II);

the metalloid-containing precursor being (N,N'-diisopropylacetamidinate)(pyrrolecarbaldpropyliminate) platinum (II);

the metalloid-containing precursor being (N,N'-diisopropylacetamidinate)(pyrrolecarbaldnbutyliminate) platinum (II);

the metalloid-containing precursor being (N,N'-diisopropylacetamidinate)(pyrrolecarbaldsecbutyliminate) platinum (II);

the metalloid-containing precursor being (N,N'-diisopropylacetamidinate)(pyrrolecarbaldisobutyliminate) platinum (II);

the metalloid-containing precursor being (N,N'-diisopropylacetamidinate)(pyrrolecarbaldtertbutyliminate) platinum (II);

the metalloid-containing precursor being (N,N'-diisopropylacetamidinate)(pyrrolecarbaldtrimethylsilyliminate) platinum (II);

the metalloid-containing precursor being (N,N'-diisopropyl-N,N'-dimethylguanidinate)(pyrrolecarbaldiminate) platinum (II);

the metalloid-containing precursor being (N,N'-diisopropyl-N,N'-dimethylguanidinate)(pyrrolecarbaldmethyliminate) platinum (II);

the metalloid-containing precursor being (N,N'-diisopropyl-N,N'-dimethylguanidinate)(pyrrolecarbaldethyliminate) platinum (II);

the metalloid-containing precursor being (N,N'-diisopropyl-N,N'-dimethylguanidinate)(pyrrolecarbaldisopropyliminate) platinum (II);

the metalloid-containing precursor being (N,N'-diisopropyl-N,N'-dimethylguanidinate)(pyrrolecarbaldpropyliminate) platinum (II);

the metalloid-containing precursor being (N,N'-diisopropyl-N,N'-dimethylguanidinate)(pyrrolecarbaldnbutyliminate) platinum (II);

the metalloid-containing precursor being (N,N'-diisopropyl-N,N'-dimethylguanidinate)(pyrrolecarbaldsecbutyliminate) platinum (II);

the metalloid-containing precursor being (N,N'-diisopropyl-N,N'-dimethylguanidinate)(pyrrolecarbaldisobutyliminate) platinum (II);

the metalloid-containing precursor being (N,N'-diisopropyl-N,N'-dimethylguanidinate)(pyrrolecarbaldtertbutyliminate) platinum (II);

the metalloid-containing precursor being (N,N'-diisopropyl-N,N'-dimethylguanidinate)(pyrrolecarbaldtrimethylsilyliminate) platinum (II);

the metalloid-containing precursor being (N,N'-2,4-pentanediketiminate)(pyrrolecarbaldiminate) ruthenium (II);

the metalloid-containing precursor being (N,N'-2,4-pentanediketiminate)(pyrrolecarbaldmethyliminate) ruthenium (II);

the metalloid-containing precursor being (N,N'-2,4-pentanediketiminate)(pyrrolecarbaldethyliminate) ruthenium (II);

the metalloid-containing precursor being (N,N'-2,4-pentanediketiminate)(pyrrolecarbaldisopropyliminate) ruthenium (II);

the metalloid-containing precursor being (N,N'-2,4-pentanediketiminate)(pyrrolecarbaldpropyliminate) ruthenium (II);

the metalloid-containing precursor being (N,N'-2,4-pentanediketiminate)(pyrrolecarbaldnbutyliminate) ruthenium (II);

the metalloid-containing precursor being (N,N'-2,4-pentanediketiminate)(pyrrolecarbaldsecbutyliminate) ruthenium (II);

the metalloid-containing precursor being (N,N'-2,4-pentanediketiminate)(pyrrolecarbaldisobutyliminate) ruthenium (II);

the metalloid-containing precursor being (N,N'-2,4-pentanediketiminate)(pyrrolecarbaldtertbutyliminate) ruthenium (II);

the metalloid-containing precursor being (N,N'-2,4-pentanediketiminate)(pyrrolecarbaldtrimethylsilyliminate) ruthenium (II);

the metalloid-containing precursor being (N,N'-dimethyl-2,4-pentanediketiminate)(pyrrolecarbaldiminate) ruthenium (II);

the metalloid-containing precursor being (N,N'-dimethyl-2,4-pentanediketiminate)(pyrrolecarbaldmethyliminate) ruthenium (II);

the metalloid-containing precursor being (N,N'-dimethyl-2,4-pentanediketiminate)(pyrrolecarbaldethyliminate) ruthenium (II);

the metalloid-containing precursor being (N,N'-dimethyl-2,4-pentanediketiminate)(pyrrolecarbaldisopropyliminate) ruthenium (II);

the metalloid-containing precursor being (N,N'-dimethyl-2,4-pentanediketiminate)(pyrrolecarbaldpropyliminate) ruthenium (II);

the metalloid-containing precursor being (N,N'-dimethyl-2,4-pentanediketiminate)(pyrrolecarbaldnbutyliminate) ruthenium (II);

the metalloid-containing precursor being (N,N'-dimethyl-2,4-pentanediketiminate)(pyrrolecarbaldsecbutyliminate) ruthenium (II);

the metalloid-containing precursor being (N,N'-dimethyl-2,4-pentanediketiminate)(pyrrolecarbaldisobutyliminate) ruthenium (II);

the metalloid-containing precursor being (N,N'-dimethyl-2,4-pentanediketiminate)(pyrrolecarbaldtertbutyliminate) ruthenium (II);

the metalloid-containing precursor being (N,N'-dimethyl-2,4-pentanediketiminate)(pyrrolecarbaldtrimethylsilyliminate) ruthenium (II);

the metalloid-containing precursor being (N,N'-diethyl-2,4-pentanediketiminate)(pyrrolecarbaldiminate) ruthenium (II);

the metalloid-containing precursor being (N,N'-diethyl-2,4-pentanediketiminate)(pyrrolecarbaldmethyliminate) ruthenium (II);

the metalloid-containing precursor being (N,N'-diethyl-2,4-pentanediketiminate)(pyrrolecarbaldethyliminate) ruthenium (II);

the metalloid-containing precursor being (N,N'-diethyl-2,4-pentanediketiminate)(pyrrolecarbaldisopropyliminate) ruthenium (II);

the metalloid-containing precursor being (N,N'-diethyl-2,4-pentanediketiminate)(pyrrolecarbaldpropyliminate) ruthenium (II);

the metalloid-containing precursor being (N,N'-diethyl-2,4-pentanediketiminate)(pyrrolecarbaldnbutyliminate) ruthenium (II);

the metalloid-containing precursor being (N,N'-diethyl-2,4-pentanediketiminate)(pyrrolecarbaldsecbutyliminate) ruthenium (II);

the metalloid-containing precursor being (N,N'-diethyl-2,4-pentanediketiminate)(pyrrolecarbaldisobutyliminate) ruthenium (II);

the metalloid-containing precursor being (N,N'-diethyl-2,4-pentanediketiminate)(pyrrolecarbaldtertbutyliminate) ruthenium (II);

the metalloid-containing precursor being (N,N'-diethyl-2,4-pentanediketiminate)(pyrrolecarbaldtrimethylsilyliminate) ruthenium (II);

the metalloid-containing precursor being (N,N'-diisopropyl-2,4-pentanediketiminate)(pyrrolecarbaldiminate) ruthenium (II);

the metalloid-containing precursor being (N,N'-diisopropyl-2,4-pentanediketiminate)(pyrrolecarbaldmethyliminate) ruthenium (II);

the metalloid-containing precursor being (N,N'-diisopropyl-2,4-pentanediketiminate)(pyrrolecarbaldethyliminate) ruthenium (II);

the metalloid-containing precursor being (N,N'-diisopropyl-2,4-pentanediketiminate)(pyrrolecarbaldisopropyliminate) ruthenium (II);

the metalloid-containing precursor being (N,N'-diisopropyl-2,4-pentanediketiminate)(pyrrolecarbaldpropyliminate) ruthenium (II);

the metalloid-containing precursor being (N,N'-diisopropyl-2,4-pentanediketiminate)(pyrrolecarbaldnbutyliminate) ruthenium (II);

the metalloid-containing precursor being (N,N'-diisopropyl-2,4-pentanediketiminate)(pyrrolecarbaldsecbutyliminate) ruthenium (II);

the metalloid-containing precursor being (N,N'-diisopropyl-2,4-pentanediketiminate)(pyrrolecarbaldisobutyliminate) ruthenium (II);

the metalloid-containing precursor being (N,N'-diisopropyl-2,4-pentanediketiminate)(pyrrolecarbaldtertbutyliminate) ruthenium (II);

the metalloid-containing precursor being (N,N'-diisopropyl-2,4-pentanediketiminate)(pyrrolecarbaldtrimethylsilyliminate) ruthenium (II);

the metalloid-containing precursor being (N,N'-dipropyl-2,4-pentanediketiminate)(pyrrolecarbaldiminate) ruthenium (II);

the metalloid-containing precursor being (N,N'-dipropyl-2,4-pentanediketiminate)(pyrrolecarbaldmethyliminate) ruthenium (II);

the metalloid-containing precursor being (N,N'-dipropyl-2,4-pentanediketiminate)(pyrrolecarbaldethyliminate) ruthenium (II);

the metalloid-containing precursor being (N,N'-dipropyl-2,4-pentanediketiminate)(pyrrolecarbaldisopropyliminate) ruthenium (II);

the metalloid-containing precursor being (N,N'-dipropyl-2,4-pentanediketiminate)(pyrrolecarbaldpropyliminate) ruthenium (II);

the metalloid-containing precursor being (N,N'-dipropyl-2,4-pentanediketiminate)(pyrrolecarbaldnbutyliminate) ruthenium (II);

the metalloid-containing precursor being (N,N'-dipropyl-2,4-pentanediketiminate)(pyrrolecarbaldsecbutyliminate) ruthenium (II);

the metalloid-containing precursor being (N,N'-dipropyl-2,4-pentanediketiminate)(pyrrolecarbaldisobutyliminate) ruthenium (II);

the metalloid-containing precursor being (N,N'-dipropyl-2,4-pentanediketiminate)(pyrrolecarbaldtertbutyliminate) ruthenium (II);

the metalloid-containing precursor being (N,N'-dipropyl-2,4-pentanediketiminate)(pyrrolecarbaldtrimethylsilyliminate) ruthenium (II);

the metalloid-containing precursor being (N,N'-di-tert-butyl-2,4-pentanediketiminate)(pyrrolecarbaldiminate) ruthenium (II);

the metalloid-containing precursor being (N,N'-di-tert-butyl-2,4-pentanediketiminate)(pyrrolecarbaldmethyliminate) ruthenium (II);

the metalloid-containing precursor being (N,N'-di-tert-butyl-2,4-pentanediketiminate)(pyrrolecarbaldethyliminate) ruthenium (II);

the metalloid-containing precursor being (N,N'-di-tert-butyl-2,4-pentanediketiminate)(pyrrolecarbaldisopropyliminate) ruthenium (II);

the metalloid-containing precursor being (N,N'-di-tert-butyl-2,4-pentanediketiminate)(pyrrolecarbaldpropyliminate) ruthenium (II);

the metalloid-containing precursor being (N,N'-di-tert-butyl-2,4-pentanediketiminate)(pyrrolecarbaldnbutyliminate) ruthenium (II);

the metalloid-containing precursor being (N,N'-di-tert-butyl-2,4-pentanediketiminate)(pyrrolecarbaldsecbutyliminate) ruthenium (II);

the metalloid-containing precursor being (N,N'-di-tert-butyl-2,4-pentanediketiminate)(pyrrolecarbaldisobutyliminate) ruthenium (II);

the metalloid-containing precursor being (N,N'-di-tert-butyl-2,4-pentanediketiminate)(pyrrolecarbaldtertbutyliminate) ruthenium (II);

the metalloid-containing precursor being (N,N'-di-tert-butyl-2,4-pentanediketiminate)(pyrrolecarbaldtrimethylsilyliminate) ruthenium (II);

the metalloid-containing precursor being (N,N'-diisopropylformamidinate)(pyrrolecarbaldiminate) ruthenium (II);

the metalloid-containing precursor being (N,N'-diisopropylformamidinate)(pyrrolecarbaldmethyliminate) ruthenium (II);

the metalloid-containing precursor being (N,N'-diisopropylformamidinate)(pyrrolecarbaldethyliminate) ruthenium (II);

the metalloid-containing precursor being (N,N'-diisopropylformamidinate)(pyrrolecarbaldisopropyliminate) ruthenium (II);

the metalloid-containing precursor being (N,N'-diisopropylformamidinate)(pyrrolecarbaldpropyliminate) ruthenium (II);

the metalloid-containing precursor being (N,N'-diisopropylformamidinate)(pyrrolecarbaldnbutyliminate) ruthenium (II);

the metalloid-containing precursor being (N,N'-diisopropylformamidinate)(pyrrolecarbaldsecbutyliminate) ruthenium (II);

the metalloid-containing precursor being (N,N'-diisopropylformamidinate)(pyrrolecarbaldisobutyliminate) ruthenium (II);

the metalloid-containing precursor being (N,N'-diisopropylformamidinate)(pyrrolecarbaldtertbutyliminate) ruthenium (II);

the metalloid-containing precursor being (N,N'-diisopropylformamidinate)(pyrrolecarbaldtrimethylsilyliminate) ruthenium (II);

the metalloid-containing precursor being (N,N'-diisopropylacetamidinate)(pyrrolecarbaldiminate) ruthenium (II);

the metalloid-containing precursor being (N,N'-diisopropylacetamidinate)(pyrrolecarbaldmethyliminate) ruthenium (II);

the metalloid-containing precursor being (N,N'-diisopropylacetamidinate)(pyrrolecarbaldethyliminate) ruthenium (II);

the metalloid-containing precursor being (N,N'-diisopropylacetamidinate)(pyrrolecarbaldisopropyliminate) ruthenium (II);

the metalloid-containing precursor being (N,N'-diisopropylacetamidinate)(pyrrolecarbaldpropyliminate) ruthenium (II);

the metalloid-containing precursor being (N,N'-diisopropylacetamidinate)(pyrrolecarbaldnbutyliminate) ruthenium (II);

the metalloid-containing precursor being (N,N'-diisopropylacetamidinate)(pyrrolecarbaldsecbutyliminate) ruthenium (II);

the metalloid-containing precursor being (N,N'-diisopropylacetamidinate)(pyrrolecarbaldisobutyliminate) ruthenium (II);

the metalloid-containing precursor being (N,N'-diisopropylacetamidinate)(pyrrolecarbaldtertbutyliminate) ruthenium (II);

the metalloid-containing precursor being (N,N'-diisopropylacetamidinate)(pyrrolecarbaldtrimethylsilyliminate) ruthenium (II);

the metalloid-containing precursor being (N,N'-diisopropyl-N,N'-dimethylguanidinate)(pyrrolecarbaldiminate) ruthenium (II);

the metalloid-containing precursor being (N,N'-diisopropyl-N,N'-dimethylguanidinate)(pyrrolecarbaldmethyliminate) ruthenium (II);

the metalloid-containing precursor being (N,N'-diisopropyl-N,N'-dimethylguanidinate)(pyrrolecarbaldethyliminate) ruthenium (II);

the metalloid-containing precursor being (N,N'-diisopropyl-N,N'-dimethylguanidinate)(pyrrolecarbaldisopropyliminate) ruthenium (II);

the metalloid-containing precursor being (N,N'-diisopropyl-N,N'-dimethylguanidinate)(pyrrolecarbaldpropyliminate) ruthenium (II);

the metalloid-containing precursor being (N,N'-diisopropyl-N,N'-dimethylguanidinate)(pyrrolecarbaldnbutyliminate) ruthenium (II);

the metalloid-containing precursor being (N,N'-diisopropyl-N,N'-dimethylguanidinate)(pyrrolecarbaldsecbutyliminate) ruthenium (II);

the metalloid-containing precursor being (N,N'-diisopropyl-N,N'-dimethylguanidinate)(pyrrolecarbaldisobutyliminate) ruthenium (II);

the metalloid-containing precursor being (N,N'-diisopropyl-N,N'-dimethylguanidinate)(pyrrolecarbaldtertbutyliminate) ruthenium (II); and the metalloid-containing precursor being (N,N'-diisopropyl-N,N'-dimethylguanidinate)(pyrrolecarbaldtrimethylsilyliminate) ruthenium (II).

Also disclosed are metalloid-containing films deposited by any of the processes disclosed above.

Notation and Nomenclature

Certain abbreviations, symbols, and terms are used throughout the following description and claims, and include: the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

The standard abbreviations of the elements from the periodic table of elements are used herein. It should be understood that elements may be referred to by these abbreviations (e.g., Ni refers to nickel, Co refers to cobalt, etc.).

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula $MR^1_x(NR^2R^3)_{(4-x)}$, where x is 2 or 3, the two or three $R^1$ groups may, but need not be identical to each other or to $R^2$ or to $R^3$. Further, it should be understood that unless specifically stated otherwise, values of R groups are independent of each other when used in different formulas.

DETAILED DESCRIPTION OF PREFERRED EMBODIMENTS

Disclosed are metalloid-containing precursors having one of the following formulae:

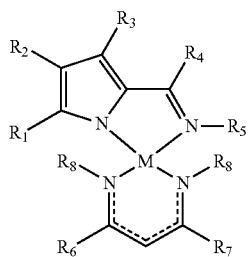

(1)

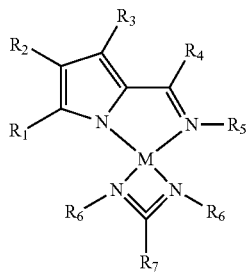

(2)

Wherein:
M is an element selected from the group consisting of Pd, Pt, and Ru; and
each of $R_1$, $R_2$, $R_3$, $R_4$, $R_5$, $R_6$, $R_7$ and $R_8$ is independently selected from H; a C1-C4 linear, branched, or cyclic alkyl group; a C1-C4 linear, branched, or cyclic alkylsilyl group (mono, bis, or tris alkyl); a C1-C4 linear, branched, or cyclic alkylamino group; or a C1-C4 linear, branched, or cyclic fluoroalkyl group.

Exemplary metalloid-containing precursors include:
(N,N'-2,4-pentanediketiminate)(pyrrolecarbaldiminate) palladium(II);
(N,N'-2,4-pentanediketiminate)(pyrrolecarbaldmethyliminate) palladium (II);
(N,N'-2,4-pentanediketiminate)(pyrrolecarbaldethyliminate) palladium (II);
(N,N'-2,4-pentanediketiminate)(pyrrolecarbaldisopropyliminate) palladium(II);
(N,N'-2,4-pentanediketiminate)(pyrrolecarbaldpropyliminate) palladium (II);
(N,N'-2,4-pentanediketiminate)(pyrrolecarbaldnbutyliminate) palladium (II);
(N,N'-2,4-pentanediketiminate)(pyrrolecarbaldsecbutyliminate) palladium (II);
(N,N'-2,4-pentanediketiminate)(pyrrolecarbaldisobutyliminate) palladium (II);
(N,N'-2,4-pentanediketiminate)(pyrrolecarbaldtertbutyliminate) palladium (II);
(N,N'-2,4-pentanediketiminate)(pyrrolecarbaldtrimethylsilyliminate) palladium (II);
(N,N'-dimethyl-2,4-pentanediketiminate)(pyrrolecarbaldiminate) palladium(II);
(N,N'-dimethyl-2,4-pentanediketiminate)(pyrrolecarbaldmethyliminate) palladium (II);
(N,N'-dimethyl-2,4-pentanediketiminate)(pyrrolecarbaldethyliminate) palladium (II);
(N,N'-dimethyl-2,4-pentanediketiminate)(pyrrolecarbaldisopropyliminate) palladium(II);
(N,N'-dimethyl-2,4-pentanediketiminate)(pyrrolecarbaldpropyliminate) palladium (II);
(N,N'-dimethyl-2,4-pentanediketiminate)(pyrrolecarbaldnbutyliminate) palladium (II);
(N,N'-dimethyl-2,4-pentanediketiminate)(pyrrolecarbaldsecbutyliminate) palladium (II);
(N,N'-dimethyl-2,4-pentanediketiminate)(pyrrolecarbaldisobutyliminate) palladium (II);
(N,N'-dimethyl-2,4-pentanediketiminate)(pyrrolecarbaldtertbutyliminate) palladium (II);
(N,N'-dimethyl-2,4-pentanediketiminate)(pyrrolecarbaldtrimethylsilyliminate) palladium (II);
(N,N'-diethyl-2,4-pentanediketiminate)(pyrrolecarbaldiminate) palladium(II);
(N,N'-diethyl-2,4-pentanediketiminate)(pyrrolecarbaldmethyliminate) palladium (II);
(N,N'-diethyl-2,4-pentanediketiminate)(pyrrolecarbaldethyliminate) palladium (II);
(N,N'-diethyl-2,4-pentanediketiminate)(pyrrolecarbaldisopropyliminate) palladium(II);
(N,N'-diethyl-2,4-pentanediketiminate)(pyrrolecarbaldpropyliminate) palladium (II);
(N,N'-diethyl-2,4-pentanediketiminate)(pyrrolecarbaldnbutyliminate) palladium (II);
(N,N'-diethyl-2,4-pentanediketiminate)(pyrrolecarbaldsecbutyliminate) palladium (II);
(N,N'-diethyl-2,4-pentanediketiminate)(pyrrolecarbaldisobutyliminate) palladium (II);
(N,N'-diethyl-2,4-pentanediketiminate)(pyrrolecarbaldtertbutyliminate) palladium (II);
(N,N'-diethyl-2,4-pentanediketiminate)(pyrrolecarbaldtrimethylsilyliminate) palladium (II);
(N,N'-diisopropyl-2,4-pentanediketiminate)(pyrrolecarbaldiminate) palladium(II);
(N,N'-diisopropyl-2,4-pentanediketiminate)(pyrrolecarbaldmethyliminate) palladium (II);
(N,N'-diisopropyl-2,4-pentanediketiminate)(pyrrolecarbaldethyliminate) palladium (II);
(N,N'-diisopropyl-2,4-pentanediketiminate)(pyrrolecarbaldisopropyliminate) palladium(II);
(N,N'-diisopropyl-2,4-pentanediketiminate)(pyrrolecarbaldpropyliminate) palladium (II);
(N,N'-diisopropyl-2,4-pentanediketiminate)(pyrrolecarbaldnbutyliminate) palladium (II);
(N,N'-diisopropyl-2,4-pentanediketiminate)(pyrrolecarbaldsecbutyliminate) palladium (II);
(N,N'-diisopropyl-2,4-pentanediketiminate)(pyrrolecarbaldisobutyliminate) palladium (II);
(N,N'-diisopropyl-2,4-pentanediketiminate)(pyrrolecarbaldtertbutyliminate) palladium (II);
(N,N'-diisopropyl-2,4-pentanediketiminate)(pyrrolecarbaldtrimethylsilyliminate)palladium (II);
(N,N'-dipropyl-2,4-pentanediketiminate)(pyrrolecarbaldiminate) palladium(II);
(N,N'-dipropyl-2,4-pentanediketiminate)(pyrrolecarbaldmethyliminate) palladium (II);
(N,N'-dipropyl-2,4-pentanediketiminate)(pyrrolecarbaldethyliminate) palladium (II);
(N,N'-dipropyl-2,4-pentanediketiminate)(pyrrolecarbaldisopropyliminate) palladium(II);
(N,N'-dipropyl-2,4-pentanediketiminate)(pyrrolecarbaldpropyliminate) palladium (II);
(N,N'-dipropyl-2,4-pentanediketiminate)(pyrrolecarbaldnbutyliminate) palladium (II);
(N,N'-dipropyl-2,4-pentanediketiminate)(pyrrolecarbaldsecbutyliminate) palladium (II);
(N,N'-dipropyl-2,4-pentanediketiminate)(pyrrolecarbaldisobutyliminate) palladium (II);
(N,N'-dipropyl-2,4-pentanediketiminate)(pyrrolecarbaldtertbutyliminate) palladium (II);

(N,N'-dipropyl-2,4-pentanediketiminate)(pyrrolecarbaldtrimethylsilyliminate)palladium (II);
(N,N'-di-tert-butyl-2,4-pentanediketiminate)(pyrrolecarbaldiminate) palladium(II);
(N,N'-di-tert-butyl-2,4-pentanediketiminate)(pyrrolecarbaldmethyliminate) palladium (II);
(N,N'-di-tert-butyl-2,4-pentanediketiminate)(pyrrolecarbaldethyliminate) palladium (II);
(N,N'-di-tert-butyl-2,4-pentanediketiminate)(pyrrolecarbaldisopropyliminate) palladium(II);
(N,N'-di-tert-butyl-2,4-pentanediketiminate)(pyrrolecarbaldpropyliminate) palladium (II);
(N,N'-di-tert-butyl-2,4-pentanediketiminate)(pyrrolecarbaldnbutyliminate) palladium (II);
(N,N'-di-tert-butyl-2,4-pentanediketiminate)(pyrrolecarbaldsecbutyliminate) palladium (II);
(N,N'-di-tert-butyl-2,4-pentanediketiminate)(pyrrolecarbaldisobutyliminate) palladium (II);
(N,N'-di-tert-butyl-2,4-pentanediketiminate)(pyrrolecarbaldtertbutyliminate) palladium (II);
(N,N'-di-tert-butyl-2,4-pentanediketiminate)(pyrrolecarbaldtrimethylsilyliminate)palladium (II);
(N,N'-diisopropylformamidinate)(pyrrolecarbaldiminate) palladium(II);
(N,N'-diisopropylformamidinate)(pyrrolecarbaldmethyliminate) palladium (II);
(N,N'-diisopropylformamidinate)(pyrrolecarbaldethyliminate) palladium (II);
(N,N'-diisopropylformamidinate)(pyrrolecarbaldisopropyliminate) palladium(II);
(N,N'-diisopropylformamidinate)(pyrrolecarbaldpropyliminate) palladium (II);
(N,N'-diisopropylformamidinate)(pyrrolecarbaldnbutyliminate) palladium (II);
(N,N'-diisopropylformamidinate)(pyrrolecarbaldsecbutyliminate) palladium (II);
(N,N'-diisopropylformamidinate)(pyrrolecarbaldisobutyliminate) palladium (II);
(N,N'-diisopropylformamidinate)(pyrrolecarbaldtertbutyliminate) palladium (II);
(N,N'-diisopropylformamidinate)(pyrrolecarbaldtrimethylsilyliminate) palladium (II);
(N,N'-diisopropylacetamidinate)(pyrrolecarbaldiminate) palladium(II);
(N,N'-diisopropylacetamidinate)(pyrrolecarbaldmethyliminate) palladium (II);
(N,N'-diisopropylacetamidinate)(pyrrolecarbaldethyliminate) palladium (II);
(N,N'-diisopropylacetamidinate)(pyrrolecarbaldisopropyliminate) palladium(II);
(N,N'-diisopropylacetamidinate)(pyrrolecarbaldpropyliminate) palladium (II);
(N,N'-diisopropylacetamidinate)(pyrrolecarbaldnbutyliminate) palladium (II);
(N,N'-diisopropylacetamidinate)(pyrrolecarbaldsecbutyliminate) palladium (II);
(N,N'-diisopropylacetamidinate)(pyrrolecarbaldisobutyliminate) palladium (II);
(N,N'-diisopropylacetamidinate)(pyrrolecarbaldtertbutyliminate) palladium (II);
(N,N'-diisopropylacetamidinate)(pyrrolecarbaldtrimethylsilyliminate) palladium (II);
(N,N'-diisopropyl-N,N'-dimethylguanidinate)(pyrrolecarbaldiminate) palladium(II);
(N,N'-diisopropyl-N,N'-dimethylguanidinate)(pyrrolecarbaldmethyliminate) palladium (II);
(N,N'-diisopropyl-N,N'-dimethylguanidinate)(pyrrolecarbaldethyliminate) palladium (II);
(N,N'-diisopropyl-N,N'-dimethylguanidinate)(pyrrolecarbaldisopropyliminate) palladium(II);
(N,N'-diisopropyl-N,N'-dimethylguanidinate)(pyrrolecarbaldpropyliminate) palladium (II);
(N,N'-diisopropyl-N,N'-dimethylguanidinate)(pyrrolecarbaldnbutyliminate) palladium (II);
(N,N'-diisopropyl-N,N'-dimethylguanidinate)(pyrrolecarbaldsecbutyliminate) palladium (II);
(N,N'-diisopropyl-N,N'-dimethylguanidinate)(pyrrolecarbaldisobutyliminate) palladium (II);
(N,N'-diisopropyl-N,N'-dimethylguanidinate)(pyrrolecarbaldtertbutyliminate) palladium (II);
(N,N'-diisopropyl-N,N'-dimethylguanidinate)(pyrrolecarbaldtrimethylsilyliminate) palladium (II);
(N,N'-2,4-pentanediketiminate)(pyrrolecarbaldiminate) platinum(II);
(N,N'-2,4-pentanediketiminate)(pyrrolecarbaldmethyliminate) platinum (II);
(N,N'-2,4-pentanediketiminate)(pyrrolecarbaldethyliminate) platinum (II);
(N,N'-2,4-pentanediketiminate)(pyrrolecarbaldisopropyliminate) platinum (II);
(N,N'-2,4-pentanediketiminate)(pyrrolecarbaldpropyliminate) platinum (II);
(N,N'-2,4-pentanediketiminate)(pyrrolecarbaldnbutyliminate) platinum (II);
(N,N'-2,4-pentanediketiminate)(pyrrolecarbaldsecbutyliminate) platinum (II);
(N,N'-2,4-pentanediketiminate)(pyrrolecarbaldisobutyliminate) platinum (II);
(N,N'-2,4-pentanediketiminate)(pyrrolecarbaldtertbutyliminate) platinum (II);
(N,N'-2,4-pentanediketiminate)(pyrrolecarbaldtrimethylsilyliminate) platinum (II);
(N,N'-dimethyl-2,4-pentanediketiminate)(pyrrolecarbaldiminate) platinum (II);
(N,N'-dimethyl-2,4-pentanediketiminate)(pyrrolecarbaldmethyliminate) platinum (II);
(N,N'-dimethyl-2,4-pentanediketiminate)(pyrrolecarbaldethyliminate) platinum (II);
(N,N'-dimethyl-2,4-pentanediketiminate)(pyrrolecarbaldisopropyliminate) platinum (II);
(N,N'-dimethyl-2,4-pentanediketiminate)(pyrrolecarbaldpropyliminate) platinum (II);
(N,N'-dimethyl-2,4-pentanediketiminate)(pyrrolecarbaldnbutyliminate) platinum (II);
(N,N'-dimethyl-2,4-pentanediketiminate)(pyrrolecarbaldsecbutyliminate) platinum (II);
(N,N'-dimethyl-2,4-pentanediketiminate)(pyrrolecarbaldisobutyliminate) platinum (II);
(N,N'-dimethyl-2,4-pentanediketiminate)(pyrrolecarbaldtertbutyliminate) platinum (II);
(N,N'-dimethyl-2,4-pentanediketiminate)(pyrrolecarbaldtrimethylsilyliminate) platinum (II);
(N,N'-diethyl-2,4-pentanediketiminate)(pyrrolecarbaldiminate) platinum (II);
(N,N'-diethyl-2,4-pentanediketiminate)(pyrrolecarbaldmethyliminate) platinum (II);
(N,N'-diethyl-2,4-pentanediketiminate)(pyrrolecarbaldethyliminate) platinum (II);
(N,N'-diethyl-2,4-pentanediketiminate)(pyrrolecarbaldisopropyliminate) platinum (II);
(N,N'-diethyl-2,4-pentanediketiminate)(pyrrolecarbaldpropyliminate) platinum (II);

(N,N'-diethyl-2,4-pentanediketiminate)(pyrrolecarbaldnbutyliminate) platinum (II);
(N,N'-diethyl-2,4-pentanediketiminate)(pyrrolecarbaldsecbutyliminate) platinum (II);
(N,N'-diethyl-2,4-pentanediketiminate)(pyrrolecarbaldisobutyliminate) platinum (II);
(N,N'-diethyl-2,4-pentanediketiminate)(pyrrolecarbaldtertbutyliminate) platinum (II);
(N,N'-diethyl-2,4-pentanediketiminate)(pyrrolecarbaldtrimethylsilyliminate) platinum (II);
(N,N'-diisopropyl-2,4-pentanediketiminate)(pyrrolecarbaldiminate) platinum (II);
(N,N'-diisopropyl-2,4-pentanediketiminate)(pyrrolecarbaldmethyliminate) platinum (II);
(N,N'-diisopropyl-2,4-pentanediketiminate)(pyrrolecarbaldethyliminate) platinum (II);
(N,N'-diisopropyl-2,4-pentanediketiminate)(pyrrolecarbaldisopropyliminate) platinum (II);
(N,N'-diisopropyl-2,4-pentanediketiminate)(pyrrolecarbaldpropyliminate) platinum (II);
(N,N'-diisopropyl-2,4-pentanediketiminate)(pyrrolecarbaldnbutyliminate) platinum (II);
(N,N'-diisopropyl-2,4-pentanediketiminate)(pyrrolecarbaldsecbutyliminate) platinum (II);
(N,N'-diisopropyl-2,4-pentanediketiminate)(pyrrolecarbaldisobutyliminate) platinum (II);
(N,N'-diisopropyl-2,4-pentanediketiminate)(pyrrolecarbaldtertbutyliminate) platinum (II);
(N,N'-diisopropyl-2,4-pentanediketiminate)(pyrrolecarbaldtrimethylsilyliminate) platinum (II);
(N,N'-dipropyl-2,4-pentanediketiminate)(pyrrolecarbaldiminate) platinum (II);
(N,N'-dipropyl-2,4-pentanediketiminate)(pyrrolecarbaldmethyliminate) platinum (II);
(N,N'-dipropyl-2,4-pentanediketiminate)(pyrrolecarbaldethyliminate) platinum (II);
(N,N'-dipropyl-2,4-pentanediketiminate)(pyrrolecarbaldisopropyliminate) platinum (II);
(N,N'-dipropyl-2,4-pentanediketiminate)(pyrrolecarbaldpropyliminate) platinum (II);
(N,N'-dipropyl-2,4-pentanediketiminate)(pyrrolecarbaldnbutyliminate) platinum (II);
(N,N'-dipropyl-2,4-pentanediketiminate)(pyrrolecarbaldsecbutyliminate) platinum (II);
(N,N'-dipropyl-2,4-pentanediketiminate)(pyrrolecarbaldisobutyliminate) platinum (II);
(N,N'-dipropyl-2,4-pentanediketiminate)(pyrrolecarbaldtertbutyliminate) platinum (II);
(N,N'-dipropyl-2,4-pentanediketiminate)(pyrrolecarbaldtrimethylsilyliminate) platinum (II);
(N,N'-di-tert-butyl-2,4-pentanediketiminate)(pyrrolecarbaldiminate) platinum (II);
(N,N'-di-tert-butyl-2,4-pentanediketiminate)(pyrrolecarbaldmethyliminate) platinum (II);
(N,N'-di-tert-butyl-2,4-pentanediketiminate)(pyrrolecarbaldethyliminate) platinum (II);
(N,N'-di-tert-butyl-2,4-pentanediketiminate)(pyrrolecarbaldisopropyliminate) platinum (II);
(N,N'-di-tert-butyl-2,4-pentanediketiminate)(pyrrolecarbaldpropyliminate) platinum (II);
(N,N'-di-tert-butyl-2,4-pentanediketiminate)(pyrrolecarbaldnbutyliminate) platinum (II);
(N,N'-di-tert-butyl-2,4-pentanediketiminate)(pyrrolecarbaldsecbutyliminate) platinum (II);
(N,N'-di-tert-butyl-2,4-pentanediketiminate)(pyrrolecarbaldisobutyliminate) platinum (II);
(N,N'-di-tert-butyl-2,4-pentanediketiminate)(pyrrolecarbaldtertbutyliminate) platinum (II);
(N,N'-di-tert-butyl-2,4-pentanediketiminate)(pyrrolecarbaldtrimethylsilyliminate) platinum (II);
(N,N'-diisopropylformamidinate)(pyrrolecarbaldiminate) platinum (II);
(N,N'-diisopropylformamidinate)(pyrrolecarbaldmethyliminate) platinum (II);
(N,N'-diisopropylformamidinate)(pyrrolecarbaldethyliminate) platinum (II);
(N,N'-diisopropylformamidinate)(pyrrolecarbaldisopropyliminate) platinum (II);
(N,N'-diisopropylformamidinate)(pyrrolecarbaldpropyliminate) platinum (II);
(N,N'-diisopropylformamidinate)(pyrrolecarbaldnbutyliminate) platinum (II);
(N,N'-diisopropylformamidinate)(pyrrolecarbaldsecbutyliminate) platinum (II);
(N,N'-diisopropylformamidinate)(pyrrolecarbaldisobutyliminate) platinum (II);
(N,N'-diisopropylformamidinate)(pyrrolecarbaldtertbutyliminate) platinum (II);
(N,N'-diisopropylformamidinate)(pyrrolecarbaldtrimethylsilyliminate) platinum (II);
(N,N'-diisopropylacetamidinate)(pyrrolecarbaldiminate) platinum (II);
(N,N'-diisopropylacetamidinate)(pyrrolecarbaldmethyliminate) platinum (II);
(N,N'-diisopropylacetamidinate)(pyrrolecarbaldethyliminate) platinum (II);
(N,N'-diisopropylacetamidinate)(pyrrolecarbaldisopropyliminate) platinum (II);
(N,N'-diisopropylacetamidinate)(pyrrolecarbaldpropyliminate) platinum (II);
(N,N'-diisopropylacetamidinate)(pyrrolecarbaldnbutyliminate) platinum (II);
(N,N'-diisopropylacetamidinate)(pyrrolecarbaldsecbutyliminate) platinum (II);
(N,N'-diisopropylacetamidinate)(pyrrolecarbaldisobutyliminate) platinum (II);
(N,N'-diisopropylacetamidinate)(pyrrolecarbaldtertbutyliminate) platinum (II);
(N,N'-diisopropylacetamidinate)(pyrrolecarbaldtrimethylsilyliminate) platinum (II);
(N,N'-diisopropyl-N,N'-dimethylguanidinate)(pyrrolecarbaldiminate) platinum (II);
(N,N'-diisopropyl-N,N'-dimethylguanidinate)(pyrrolecarbaldmethyliminate) platinum (II);
(N,N'-diisopropyl-N,N'-dimethylguanidinate)(pyrrolecarbaldethyliminate) platinum (II);
(N,N'-diisopropyl-N,N'-dimethylguanidinate)(pyrrolecarbaldisopropyliminate) platinum (II);
(N,N'-diisopropyl-N,N'-dimethylguanidinate)(pyrrolecarbaldpropyliminate) platinum (II);
(N,N'-diisopropyl-N,N'-dimethylguanidinate)(pyrrolecarbaldnbutyliminate) platinum (II);
(N,N'-diisopropyl-N,N'-dimethylguanidinate)(pyrrolecarbaldsecbutyliminate) platinum (II);
(N,N'-diisopropyl-N,N'-dimethylguanidinate)(pyrrolecarbaldisobutyliminate) platinum (II);
(N,N'-diisopropyl-N,N'-dimethylguanidinate)(pyrrolecarbaldtertbutyliminate) platinum (II);
(N,N'-diisopropyl-N,N'-dimethylguanidinate)(pyrrolecarbaldtrimethylsilyliminate) platinum (II);
(N,N'-2,4-pentanediketiminate)(pyrrolecarbaldiminate) ruthenium (II);

(N,N'-2,4-pentanediketiminate)(pyrrolecarbaldmethyliminate) ruthenium (II);
(N,N'-2,4-pentanediketiminate)(pyrrolecarbaldethyliminate) ruthenium (II);
(N,N'-2,4-pentanediketiminate)(pyrrolecarbaldisopropyliminate) ruthenium (II);
(N,N'-2,4-pentanediketiminate)(pyrrolecarbaldpropyliminate) ruthenium (II);
(N,N'-2,4-pentanediketiminate)(pyrrolecarbaldnbutyliminate) ruthenium (II);
(N,N'-2,4-pentanediketiminate)(pyrrolecarbaldsecbutyliminate) ruthenium (II);
(N,N'-2,4-pentanediketiminate)(pyrrolecarbaldisobutyliminate) ruthenium (II);
(N,N'-2,4-pentanediketiminate)(pyrrolecarbaldtertbutyliminate) ruthenium (II);
(N,N'-2,4-pentanediketiminate)(pyrrolecarbaldtrimethylsilyliminate) ruthenium (II);
(N,N'-dimethyl-2,4-pentanediketiminate)(pyrrolecarbaldiminate) ruthenium (II);
(N,N'-dimethyl-2,4-pentanediketiminate)(pyrrolecarbaldmethyliminate) ruthenium (II);
(N,N'-dimethyl-2,4-pentanediketiminate)(pyrrolecarbaldethyliminate) ruthenium (II);
(N,N'-dimethyl-2,4-pentanediketiminate)(pyrrolecarbaldisopropyliminate) ruthenium (II);
(N,N'-dimethyl-2,4-pentanediketiminate)(pyrrolecarbaldpropyliminate) ruthenium (II);
(N,N'-dimethyl-2,4-pentanediketiminate)(pyrrolecarbaldnbutyliminate) ruthenium (II);
(N,N'-dimethyl-2,4-pentanediketiminate)(pyrrolecarbaldsecbutyliminate) ruthenium (II);
(N,N'-dimethyl-2,4-pentanediketiminate)(pyrrolecarbaldisobutyliminate) ruthenium (II);
(N,N'-dimethyl-2,4-pentanediketiminate)(pyrrolecarbaldtertbutyliminate) ruthenium (II);
(N,N'-dimethyl-2,4-pentanediketiminate)(pyrrolecarbaldtrimethylsilyliminate) ruthenium (II);
(N,N'-diethyl-2,4-pentanediketiminate)(pyrrolecarbaldiminate) ruthenium (II);
(N,N'-diethyl-2,4-pentanediketiminate)(pyrrolecarbaldmethyliminate) ruthenium (II);
(N,N'-diethyl-2,4-pentanediketiminate)(pyrrolecarbaldethyliminate) ruthenium (II);
(N,N'-diethyl-2,4-pentanediketiminate)(pyrrolecarbaldisopropyliminate) ruthenium (II);
(N,N'-diethyl-2,4-pentanediketiminate)(pyrrolecarbaldpropyliminate) ruthenium (II);
(N,N'-diethyl-2,4-pentanediketiminate)(pyrrolecarbaldnbutyliminate) ruthenium (II);
(N,N'-diethyl-2,4-pentanediketiminate)(pyrrolecarbaldsecbutyliminate) ruthenium (II);
(N,N'-diethyl-2,4-pentanediketiminate)(pyrrolecarbaldisobutyliminate) ruthenium (II);
(N,N'-diethyl-2,4-pentanediketiminate)(pyrrolecarbaldtertbutyliminate) ruthenium (II);
(N,N'-diethyl-2,4-pentanediketiminate)(pyrrolecarbaldtrimethylsilyliminate) ruthenium (II);
(N,N'-diisopropyl-2,4-pentanediketiminate)(pyrrolecarbaldiminate) ruthenium (II);
(N,N'-diisopropyl-2,4-pentanediketiminate)(pyrrolecarbaldmethyliminate) ruthenium (II);
(N,N'-diisopropyl-2,4-pentanediketiminate)(pyrrolecarbaldethyliminate) ruthenium (II);
(N,N'-diisopropyl-2,4-pentanediketiminate)(pyrrolecarbaldisopropyliminate) ruthenium (II);
(N,N'-diisopropyl-2,4-pentanediketiminate)(pyrrolecarbaldpropyliminate) ruthenium (II);
(N,N'-diisopropyl-2,4-pentanediketiminate)(pyrrolecarbaldnbutyliminate) ruthenium (II);
(N,N'-diisopropyl-2,4-pentanediketiminate)(pyrrolecarbaldsecbutyliminate) ruthenium (II);
(N,N'-diisopropyl-2,4-pentanediketiminate)(pyrrolecarbaldisobutyliminate) ruthenium (II);
(N,N'-diisopropyl-2,4-pentanediketiminate)(pyrrolecarbaldtertbutyliminate) ruthenium (II);
(N,N'-diisopropyl-2,4-pentanediketiminate)(pyrrolecarbaldtrimethylsilyliminate) ruthenium (II);
(N,N'-dipropyl-2,4-pentanediketiminate)(pyrrolecarbaldiminate) ruthenium (II);
(N,N'-dipropyl-2,4-pentanediketiminate)(pyrrolecarbaldmethyliminate) ruthenium (II);
(N,N'-dipropyl-2,4-pentanediketiminate)(pyrrolecarbaldethyliminate) ruthenium (II);
(N,N'-dipropyl-2,4-pentanediketiminate)(pyrrolecarbaldisopropyliminate) ruthenium (II);
(N,N'-dipropyl-2,4-pentanediketiminate)(pyrrolecarbaldpropyliminate) ruthenium (II);
(N,N'-dipropyl-2,4-pentanediketiminate)(pyrrolecarbaldnbutyliminate) ruthenium (II);
(N,N'-dipropyl-2,4-pentanediketiminate)(pyrrolecarbaldsecbutyliminate) ruthenium (II);
(N,N'-dipropyl-2,4-pentanediketiminate)(pyrrolecarbaldisobutyliminate) ruthenium (II);
(N,N'-dipropyl-2,4-pentanediketiminate)(pyrrolecarbaldtertbutyliminate) ruthenium (II);
(N,N'-dipropyl-2,4-pentanediketiminate)(pyrrolecarbaldtrimethylsilyliminate) ruthenium (II);
(N,N'-di-tert-butyl-2,4-pentanediketiminate)(pyrrolecarbaldiminate) ruthenium (II);
(N,N'-di-tert-butyl-2,4-pentanediketiminate)(pyrrolecarbaldmethyliminate) ruthenium (II);
(N,N'-di-tert-butyl-2,4-pentanediketiminate)(pyrrolecarbaldethyliminate) ruthenium (II);
(N,N'-di-tert-butyl-2,4-pentanediketiminate)(pyrrolecarbaldisopropyliminate) ruthenium (II);
(N,N'-di-tert-butyl-2,4-pentanediketiminate)(pyrrolecarbaldpropyliminate) ruthenium (II);
(N,N'-di-tert-butyl-2,4-pentanediketiminate)(pyrrolecarbaldnbutyliminate) ruthenium (II);
(N,N'-di-tert-butyl-2,4-pentanediketiminate)(pyrrolecarbaldsecbutyliminate) ruthenium (II);
(N,N'-di-tert-butyl-2,4-pentanediketiminate)(pyrrolecarbaldisobutyliminate) ruthenium (II);
(N,N'-di-tert-butyl-2,4-pentanediketiminate)(pyrrolecarbaldtertbutyliminate) ruthenium (II);
(N,N'-di-tert-butyl-2,4-pentanediketiminate)(pyrrolecarbaldtrimethylsilyliminate) ruthenium (II);
(N,N'-diisopropylformamidinate)(pyrrolecarbaldiminate) ruthenium (II);
(N,N'-diisopropylformamidinate)(pyrrolecarbaldmethyliminate) ruthenium (II);
(N,N'-diisopropylformamidinate)(pyrrolecarbaldethyliminate) ruthenium (II);
(N,N'-diisopropylformamidinate)(pyrrolecarbaldisopropyliminate) ruthenium (II);
(N,N'-diisopropylformamidinate)(pyrrolecarbaldpropyliminate) ruthenium (II);
(N,N'-diisopropylformamidinate)(pyrrolecarbaldnbutyliminate) ruthenium (II);
(N,N'-diisopropylformamidinate)(pyrrolecarbaldsecbutyliminate) ruthenium (II);

(N,N'-diisopropylformamidinate)(pyrrolecarbaldisobutyl-iminate) ruthenium (II);
(N,N'-diisopropylformamidinate)(pyrrolecarbaldtertbutyl-iminate) ruthenium (II);
(N,N'-diisopropylformamidinate)(pyrrolecarbaldtrimethyl-silyliminate) ruthenium (II);
(N,N'-diisopropylacetamidinate)(pyrrolecarbaldiminate) ruthenium (II);
(N,N'-diisopropylacetamidinate)(pyrrolecarbaldmethylimi-nate) ruthenium (II);
(N,N'-diisopropylacetamidinate)(pyrrolecarbaldethylimi-nate) ruthenium (II);
(N,N'-diisopropylacetamidinate)(pyrrolecarbaldisopropy-liminate) ruthenium (II);
(N,N'-diisopropylacetamidinate)(pyrrolecarbaldpropylimi-nate) ruthenium (II);
(N,N'-diisopropylacetamidinate)(pyrrolecarbaldnbutylimi-nate) ruthenium (II);
(N,N'-diisopropylacetamidinate)(pyrrolecarbaldsecbutyl-iminate) ruthenium (II);
(N,N'-diisopropylacetamidinate)(pyrrolecarbaldisobutylimi-nate) ruthenium (II);
(N,N'-diisopropylacetamidinate)(pyrrolecarbaldtertbutyl-iminate) ruthenium (II);
(N,N'-diisopropylacetamidinate)(pyrrolecarbaldtrimethylsi-lyliminate) ruthenium (II);
(N,N'-diisopropyl-N,N'-dimethylguanidinate)(pyrrolecar-baldiminate) ruthenium (II);
(N,N'-diisopropyl-N,N'-dimethylguanidinate)(pyrrolecar-baldmethyliminate) ruthenium (II);
(N,N'-diisopropyl-N,N'-dimethylguanidinate)(pyrrolecar-baldethyliminate) ruthenium (II);
(N,N'-diisopropyl-N,N'-dimethylguanidinate)(pyrrolecar-baldisopropyliminate) ruthenium (II);
(N,N'-diisopropyl-N,N'-dimethylguanidinate)(pyrrolecar-baldpropyliminate) ruthenium (II);
(N,N'-diisopropyl-N,N'-dimethylguanidinate)(pyrrolecar-baldnbutyliminate) ruthenium (II);
(N,N'-diisopropyl-N,N'-dimethylguanidinate)(pyrrolecar-baldsecbutyliminate) ruthenium (II);
(N,N'-diisopropyl-N,N'-dimethylguanidinate)(pyrrolecar-baldisobutyliminate) ruthenium (II);
(N,N'-diisopropyl-N,N'-dimethylguanidinate)(pyrrolecar-baldtertbutyliminate) ruthenium (II); and
(N,N'-diisopropyl-N,N'-dimethylguanidinate)(pyrrolecar-baldtrimethylsilyliminate) ruthenium (II).

Preferably, the precursor is (N,N'-diisopropylacetamidi-nate)(pyrrolecarbaldisopropyliminate) palladium(II); (N,N'-diisopropylacetamidinate)(pyrrolecarbaldisopropyliminate) platinum (II); or (N,N'-diisopropylacetamidinate)(pyrrole-carbaldisopropyliminate) ruthenium(II). Applicants believe that $R_1$-$R_4$ being hydrogen, $R_5$ and $R_6$ being isopropyl, and $R_7$ being methyl in Formula 2 will provide compounds having the lowest melting points without significant decrease in volatility.

The disclosed precursors may be synthesized in one step according to the reaction scheme 1 by reacting simultaneously a bis halide or bis acetylacetonate with one equivalent of deprotonated pyrrolylcarbaldimine ligand and one equivalent of deprotonated diketiminato or amidinate ligand.

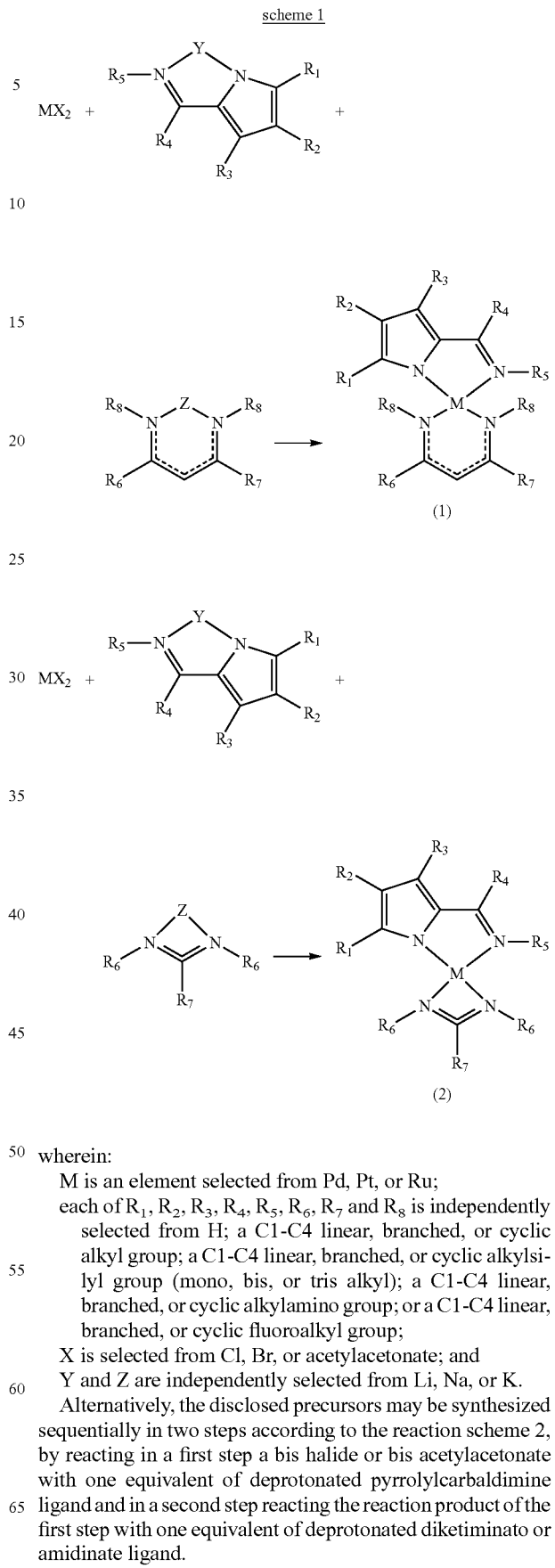

wherein:
M is an element selected from Pd, Pt, or Ru;
each of $R_1$, $R_2$, $R_3$, $R_4$, $R_5$, $R_6$, $R_7$ and $R_8$ is independently selected from H; a C1-C4 linear, branched, or cyclic alkyl group; a C1-C4 linear, branched, or cyclic alkylsilyl group (mono, bis, or tris alkyl); a C1-C4 linear, branched, or cyclic alkylamino group; or a C1-C4 linear, branched, or cyclic fluoroalkyl group;
X is selected from Cl, Br, or acetylacetonate; and
Y and Z are independently selected from Li, Na, or K.

Alternatively, the disclosed precursors may be synthesized sequentially in two steps according to the reaction scheme 2, by reacting in a first step a bis halide or bis acetylacetonate with one equivalent of deprotonated pyrrolylcarbaldimine ligand and in a second step reacting the reaction product of the first step with one equivalent of deprotonated diketiminato or amidinate ligand.

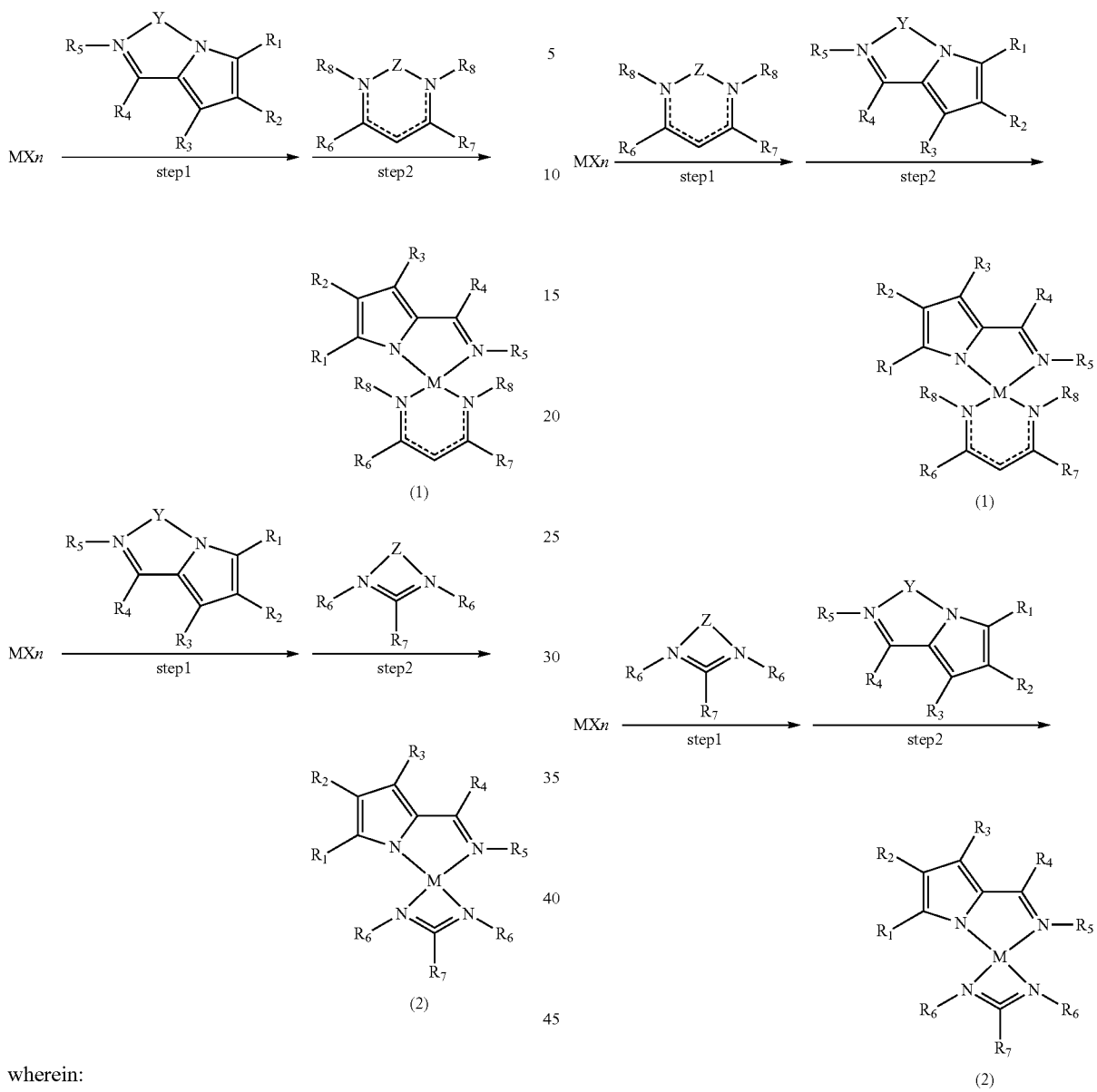

wherein:

M is an element selected from Pd, Pt, or Ru;

each of $R_1$, $R_2$, $R_3$, $R_4$, $R_5$, $R_6$, $R_7$ and $R_8$ is independently selected from H; a C1-C4 linear, branched, or cyclic alkyl group; a C1-C4 linear, branched, or cyclic alkylsilyl group (mono, bis, or tris alkyl); a C1-C4 linear, branched, or cyclic alkylamino group; or a C1-C4 linear, branched, or cyclic fluoroalkyl group;

X is selected from Cl, Br, or acetylacetonate;

n is 1, 2, or 3; and

Y and Z are selected from Li, Na, or K.

In another alternative, the disclosed precursors may be synthesized sequentially in two steps according to the reaction scheme 3, by reacting in a first step a bis halide or bis acetylacetonate with one equivalent of deprotonated diketiminato or amidinate ligand and in a second step reacting the reaction product of the first step with one equivalent of deprotonated pyrrolylcarbaldimine ligand.

wherein:

M is an element selected from Pd, Pt, or Ru;

each of $R_1$, $R_2$, $R_3$, $R_4$, $R_5$, $R_6$, $R_7$ and $R_8$ is independently selected from H; a C1-C4 linear, branched, or cyclic alkyl group; a C1-C4 linear, branched, or cyclic alkylsilyl group (mono, bis, or tris alkyl); a C1-C4 linear, branched, or cyclic alkylamino group; or a C1-C4 linear, branched, or cyclic fluoroalkyl group;

X is selected from Cl, Br, or acetylacetonate;

n is 1, 2, or 3; and

Y and Z are independently selected from Li, Na, or K.

In another alternative, the disclosed precursors may be synthesized according to the reaction scheme 4 by reacting a bis pyrrolylcarbaldimine with one equivalent of deprotonated or not deprotonated diketiminato or amidinate ligand.

scheme 4

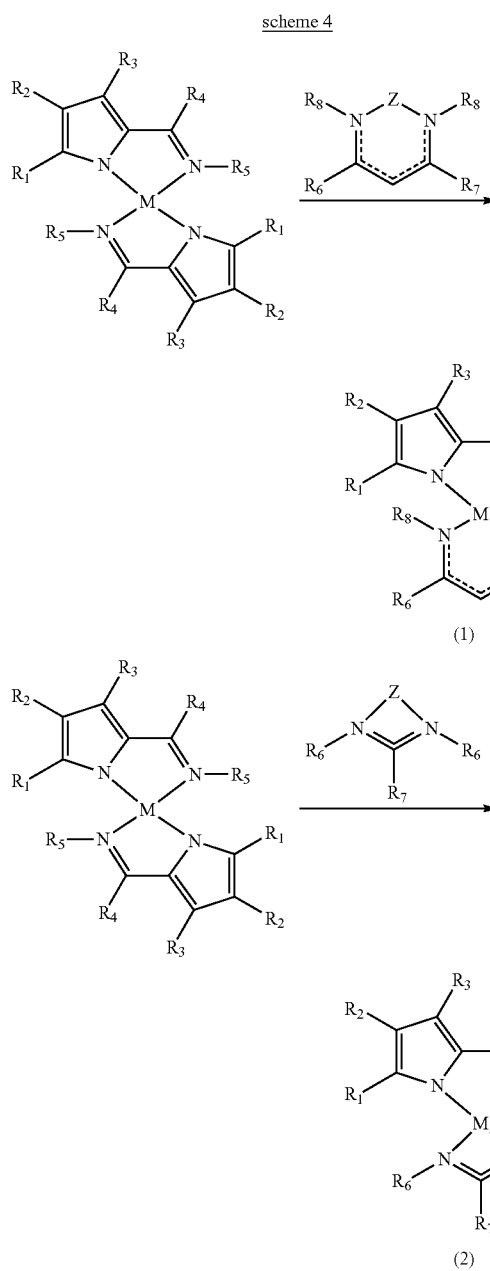

(1)

(2)

wherein:
M is an element selected from Pd, Pt, or Ru;
each of $R_1$, $R_2$, $R_3$, $R_4$, $R_5$, $R_6$, $R_7$ and $R_8$ are independently selected from H; a C1-C4 linear, branched, or cyclic alkyl group; a C1-C4 linear, branched, or cyclic alkylsilyl group (mono, bis, or tris alkyl); a C1-C4 linear, branched, or cyclic alkylamino group; or a C1-C4 linear, branched, or cyclic fluoroalkyl group;
X is selected from Cl, Br, or acetylacetonate; and
Y and Z are independently selected from H, Li, Na, or K.

In another alternative, the disclosed precursors may be synthesized according to the reaction scheme 5 by reacting a bis diketiminato or amidinato with one equivalent of deprotonated or not deprotonated pyrrolylcarbaldimine ligand.

scheme 5

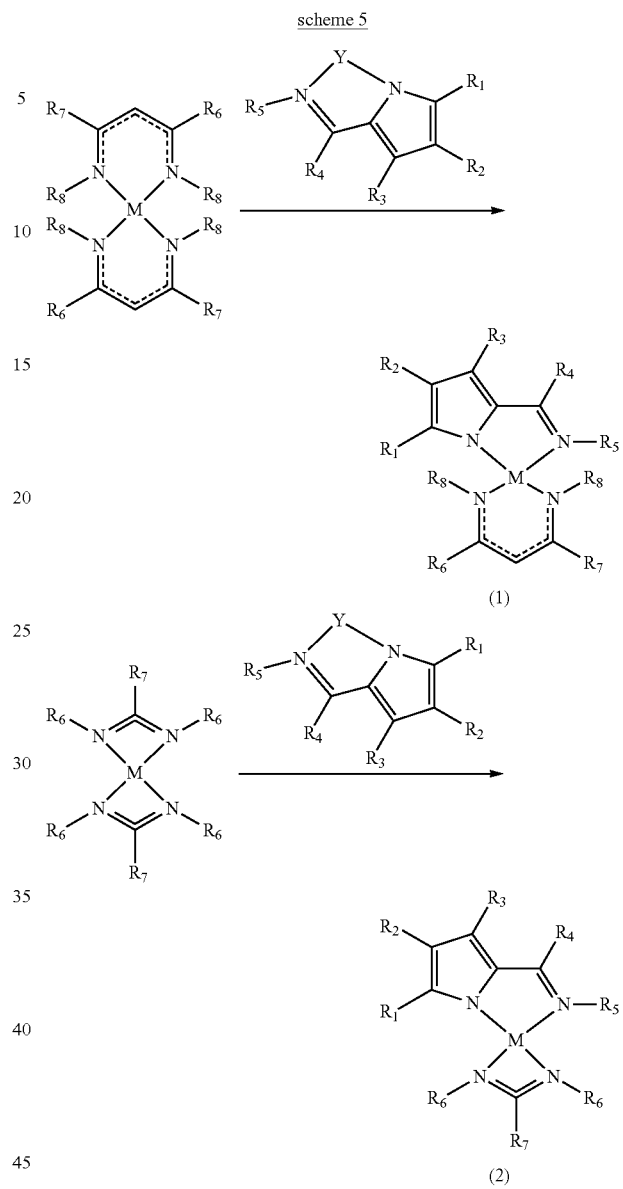

(1)

(2)

wherein:
M is an element selected from Pd, Pt, or Ru;
each of $R_1$, $R_2$, $R_3$, $R_4$, $R_5$, $R_6$, $R_7$ and $R_8$ are independently selected from H; a C1-C4 linear, branched, or cyclic alkyl group; a C1-C4 linear, branched, or cyclic alkylsilyl group (mono, bis, or tris alkyl); a C1-C4 linear, branched, or cyclic alkylamino group; or a C1-C4 linear, branched, or cyclic fluoroalkyl group;
X is selected from Cl, Br, or acetylacetonate; and
Y is selected from H, Li, Na, or K.

The synthesis may be performed in a polar solvent selected without limitation from THF, acetonitrile, dimethylsulfoxide, or diethylether.

The synthesis may be performed at a temperature ranging from approximately 100° C. to approximately 150° C.

A coordinating species may be introduced during the first step in reaction schemes 2 and 3 in order to stabilize the reaction intermediate. The coordinating species may be selected without limitation from trialkylamine (triethylamine), $N_1,N_1,N_2,N_2$-tetramethylethane-1,2-diamine, pyridine, or ether.

The synthesis may include the steps of removing the solvent, adding a non polar solvent (pentane or hexane for instance) to form a solution, filtering the solution, and removing the solvent to form the disclosed precursor having the formula (1) or (2).

The synthesis may include the step of purifying the precursor having the formula (1) or (2) by recrystallisation, distillation, or sublimation.

At least part of the disclosed precursors may be deposited to form a thin film using any deposition methods known to those of skill in the art. Examples of suitable deposition methods include without limitation, conventional CVD, plasma enhanced CVD (PECVD), atomic layer deposition (ALD), plasma enhanced ALD (PEALD), pulsed chemical vapor deposition (P-CVD), and focused ion beam nanopatterning (FIB). In one alternative, a CVD deposition is preferred, particularly when fast growth, conformality, process-orientation and one direction films are required. In another alternative, an ALD deposition process is preferred, particularly when superior conformality of films deposited on challenging surfaces (e.g., trenchs, holes, vias) is required. In another alternative, FIB is preferred, particularly when forming low resistance ohmic platinum contacts on bismuth, silver, or gallium nitride nanowires or carbon nanotubes.

The disclosed precursor is introduced into a reactor in vapor form. The vapor form of the precursor may be produced by vaporizing a liquid precursor solution through a conventional vaporization step such as direct vaporization, distillation, or by bubbling an inert gas (e.g. $N_2$, He, Ar, etc.) into the precursor solution and providing the inert gas plus precursor mixture as a precursor vapor solution to the reactor. Bubbling with an inert gas may also remove any dissolved oxygen present in the precursor solution.

If necessary, the container may be heated to a temperature that permits the disclosed precursor to be in its liquid phase and to have a sufficient vapor pressure. The container may be maintained at temperatures in the range of, for example, 0° C. to 150° C. Those skilled in the art recognize that the temperature and pressure of the container may be adjusted in a known manner to control the amount of precursor vaporized.

The reactor contains one or more substrates onto which the thin films will be deposited. The one or more substrates may be any suitable substrate used in semiconductor, photovoltaic, flat panel, or LCD-TFT device manufacturing. Examples of suitable substrates include without limitation, silicon, silica, silicon nitride, carbon-doped silica, hydrogenated silicon carbide, bismuth, tantalum, tantalum nitride, hafnium boride, silicon oxy nitride, titanium nitride, tungsten, tungsten nitride, gallium nitride, or combinations thereof. The silicon substrates may optionally be cleaned with a HF rinse prior to deposition. Additionally, substrates comprising tungsten or noble metals (e.g. platinum, palladium, rhodium, ruthenium, silver, or gold) may be used. Substrates may contain one or more additional layers of materials, which may be present from a previous manufacturing step. Dielectric and conductive layers are examples of these.

The temperature and the pressure within the reactor and the temperature of the substrate are held at conditions suitable for vapor deposition of at least part of the disclosed precursor onto the substrate. The reactor or deposition chamber may be a heated vessel which has at least one or more substrates disposed within. The reactor has an outlet, which may be connected to a vacuum pump to allow by products to be removed from the chamber, or to allow the pressure within the reactor to be modified or regulated. The temperature in the chamber is normally maintained at a suitable temperature for the type of deposition process which is to be performed. In some cases, the chamber may be maintained at a lower temperature, for instance when the substrates themselves are heated directly, or where another energy source (e.g. plasma or radio frequency source, microwave sources, UV light, or focused ion beam) is provided to aid in the deposition. Examples of reactors include, without limitation, a cold-wall type reactor, a hot-wall type reactor, a single-wafer reactor, a multi-wafer reactor, or other types of deposition systems under conditions suitable to cause the precursors to react and form the layers. Any of these reactors may be used for both ALD and CVD processes and therefore qualify as an ALD reactor or a CVD reactor.

In one alternative, the deposition chamber is maintained at a temperature greater than about 100° C. For example, the temperature is maintained between about 100° C. and about 500° C., preferably, between about 150° C. and about 350° C. In another alternative, the deposition chamber may be maintained at a temperature ranging from approximately 20° C. to approximately 100° C. The pressure in the deposition chamber is maintained at a pressure between about 1 Pa and about $10^5$ Pa, and preferably between about 25 Pa, and about $10^3$ Pa.

Depending on the particular process parameters, deposition may take place for a varying length of time. Generally, deposition may be allowed to continue as long as desired to produce a film with the necessary properties. Typical film thicknesses may vary from a few angstroms to several hundreds of microns, depending on the specific deposition process.

In some embodiments, a reducing gas may also be introduced into the reaction chamber. The reducing gas may be one of hydrogen, ammonia, silane, disilane, trisilane, the plasma excited radicals thereof, and mixtures thereof. Exemplary plasma excited radicals include hydrogen radicals. The plasma excited radicals may be generated by a plasma located within the reactor, with the wafer located between two electrodes, or remote from the reactor. When the mode of deposition is chemical vapor deposition, the disclosed precursor and the reducing gas may be introduced to the reaction chamber substantially simultaneously. When the mode of deposition is atomic layer deposition, the disclosed precursor and the reducing gas may be introduced sequentially, and in some cases, there may be an inert gas purge introduced between the precursor and reducing gas.

One or more precursors may also be introduced into the reaction chamber and deposited on the substrate. The additional precursors may serve as a component of the film to be deposited or as a doping agent (i.e., a small amount). The additional precursors each may independently comprise an element selected from such as barium, calcium, copper, silicon, praseodymium, manganese, strontium, titanium, tantalum, bismuth, zirconium, hafnium, lead, niobium, magnesium, aluminum, lanthanum, or mixtures of these. By providing the disclosed precursor along with additional precursors, a multi-element film may be formed on the substrate, for instance, PtSi, NiSiPt, NiSiPd, SrRuO, CaRuO, or BaRuO.

The disclosed precursors and any optional reactants or precursors may be introduced sequentially (as in ALD) or simultaneously (as in CVD) into the reaction chamber. The reaction chamber may be purged with an inert gas between the introduction of the precursor and the introduction of the reactant. Alternatively, the reactant and the precursor may be mixed together to form a reactant/precursor mixture, and then introduced to the reactor in mixture form. In another alternative, either the disclosed precursors or any optional reactants or precursors may be introduced into the reaction chamber, while a second component (either the disclosed precursor or any optional reactants or precursors) is pulsed into the reaction chamber (pulsed CVD).

The disclosed precursor vapor solution and the reaction gas may be pulsed sequentially or simultaneously (e.g. pulsed CVD) into the reactor. Each pulse of precursor may last for a time period ranging from about 0.01 seconds to about 10 seconds, alternatively from about 0.3 seconds to about 3 seconds, alternatively from about 0.5 seconds to about 2 seconds. In another embodiment, the reaction gas may also be pulsed into the reactor. In such embodiments, the pulse of each gas may last for a time period ranging from about 0.01 seconds to about 10 seconds, alternatively from about 0.3 seconds to about 3 seconds, alternatively from about 0.5 seconds to about 2 seconds.

In one non-limiting exemplary atomic layer deposition type process, the vapor phase of the disclosed precursor is introduced into the reaction chamber, where it is contacted with a suitable substrate. Excess precursor may then be removed from the reaction chamber by purging and/or evacuating the reaction chamber. An oxygen source, such as oxygen, ozone, plasma excited radicals thereof, or combinations thereof, is introduced into the reaction chamber where it reacts with the absorbed precursor in a self-limiting manner. Any excess oxygen source is removed from the reaction chamber by purging and/or evacuating the reaction chamber. If the desired film is an oxide film, this two-step process may provide the desired film thickness or may be repeated until a film having the necessary thickness has been obtained.

Alternatively, if the desired film contains two elements, the vapor phase of the disclosed precursor may be introduced into the reaction chamber, where it is contacted with a suitable substrate. Excess precursor may then be removed from the reaction chamber by purging and/or evacuating the reaction chamber. The vapor phase of a second precursor, such as a strontium-containing precursor or a barium-containing precursor, is introduced into the reaction chamber where it reacts with the absorbed precursor in a self-limiting manner. Any excess second precursor is removed from the reaction chamber by purging and/or evacuating the reaction chamber. This two-step process may provide the desired film thickness or may be repeated until a film having the necessary thickness has been obtained.

By varying the number of pulses, films having a desired stoichiometric ratio may be obtained. For example, if the SrRuO film contains less than the desired amount of ruthenium, the exemplary process described above may be altered to include an additional introduction (e.g., a second pulse) of the disclosed precursor. One of ordinary skill in the art will recognize that the number of pulses required to obtain the desired film may not be identical to the stoichiometric ratio of the resulting film.

The metalloid-containing films resulting from the processes discussed above may include Pd, NiSiPd, Pt, PtSi, NiSiPt, Ru, RuO, SrRuO, BaRuO, or CaRuO. One of ordinary skill in the art will recognize that by judicial selection of the appropriate disclosed precursor, reactants, and precursors, the desired film composition may be obtained.

In another alternative, the disclosed metalloid-containing precursors may be used as doping or implantation agents, particularly the palladium-containing and platinum-containing precursors. The disclosed metalloid-containing precursors may be deposited on top of the film to be doped. The metalloid then diffuses into the film during an annealing step. See, e.g., US2008/0241575 to Lavoie et al., the doping method of which is incorporated herein by reference in its entirety. Alternatively, high energy ion implantation using a variable energy radio frequency quadrupole implanter may be used to dope the metalloid of the metalloid-containing precursor into a film. See, e.g., Kensuke et al., JVSTA 16(2) March/April 1998, the implantation method of which is incorporated herein by reference in its entirety. In another alternative, plasma doping, pulsed plasma doping or plasma immersion ion implantation may be performed using the disclosed metalloid-containing precursors. See, e.g., Felch et al., Plasma doping for the fabrication of ultra-shallow junctions Surface Coatings Technology, 156 (1-3) 2002, pp. 229-236, the doping method of which is incorporated herein by reference in its entirety.

While embodiments of this invention have been shown and described, modifications thereof can be made by one skilled in the art without departing from the spirit or teaching of this invention. The embodiments described herein are exemplary only and not limiting. Many variations and modifications of the composition and method are possible and within the scope of the invention. Accordingly the scope of protection is not limited to the embodiments described herein, but is only limited by the claims which follow, the scope of which shall include all equivalents of the subject matter of the claims.

What is claimed is:

1. A precursor having one of the following formulas:

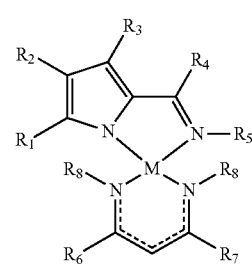

(1)

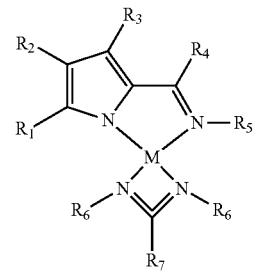

(2)

wherein:
M is an element selected from the group consisting of Pd, Pt, and Ru; and
each of $R_1$, $R_2$, $R_3$, $R_4$, $R_5$, $R_6$, $R_7$ and $R_8$ is independently selected from H; a C1-C4 linear, branched, or cyclic alkyl group; a C1-C4 linear, branched, or cyclic alkylsilyl group (mono, bis, or tris alkyl); a C1-C4 linear, branched, or cyclic alkylamino group; or
a C1-C4 linear, branched, or cyclic fluoroalkyl group.

2. The precursor of claim 1, selected from the group consisting of:
(N,N'-2,4-pentanediketiminate)(pyrrolecarbaldiminate) palladium(II);
(N,N'-2,4-pentanediketiminate)(pyrrolecarbaldmethyliminate) palladium (II);

(N,N'-2,4-pentanediketiminate)(pyrrolecarbaldethyliminate) palladium (II);
(N,N'-2,4-pentanediketiminate)(pyrrolecarbaldisopropyliminate) palladium(II);
(N,N'-2,4-pentanediketiminate)(pyrrolecarbaldpropyliminate) palladium (II);
(N,N'-2,4-pentanediketiminate)(pyrrolecarbaldnbutyliminate) palladium (II);
(N,N'-2,4-pentanediketiminate)(pyrrolecarbaldsecbutyliminate) palladium (II);
(N,N'-2,4-pentanediketiminate)(pyrrolecarbaldisobutyliminate) palladium (II);
(N,N'-2,4-pentanediketiminate)(pyrrolecarbaldtertbutyliminate) palladium (II);
(N,N'-2,4-pentanediketiminate)(pyrrolecarbaldtrimethylsilyliminate) palladium (II);
(N,N'-dimethyl-2,4-pentanediketiminate)(pyrrolecarbaldiminate) palladium(II);
(N,N'-dimethyl-2,4-pentanediketiminate)(pyrrolecarbaldmethyliminate) palladium (II);
(N,N'-dimethyl-2,4-pentanediketiminate)(pyrrolecarbaldethyliminate) palladium (II);
(N,N'-dimethyl-2,4-pentanediketiminate)(pyrrolecarbaldisopropyliminate) palladium(II);
(N,N'-dimethyl-2,4-pentanediketiminate)(pyrrolecarbaldpropyliminate) palladium (II);
(N,N'-dimethyl-2,4-pentanediketiminate)(pyrrolecarbaldnbutyliminate) palladium (II);
(N,N'-dimethyl-2,4-pentanediketiminate)(pyrrolecarbaldsecbutyliminate) palladium (II);
(N,N'-dimethyl-2,4-pentanediketiminate)(pyrrolecarbaldisobutyliminate) palladium (II);
(N,N'-dimethyl-2,4-pentanediketiminate)(pyrrolecarbaldtertbutyliminate) palladium (II);
(N,N'-dimethyl-2,4-pentanediketiminate)(pyrrolecarbaldtrimethylsilyliminate) palladium (II);
(N,N'-diethyl-2,4-pentanediketiminate)(pyrrolecarbaldiminate) palladium(II);
(N,N'-diethyl-2,4-pentanediketiminate)(pyrrolecarbaldmethyliminate) palladium (II);
(N,N'-diethyl-2,4-pentanediketiminate)(pyrrolecarbaldethyliminate) palladium (II);
(N,N'-diethyl-2,4-pentanediketiminate)(pyrrolecarbaldisopropyliminate) palladium(II);
(N,N'-diethyl-2,4-pentanediketiminate)(pyrrolecarbaldpropyliminate) palladium (II);
(N,N'-diethyl-2,4-pentanediketiminate)(pyrrolecarbaldnbutyliminate) palladium (II);
(N,N'-diethyl-2,4-pentanediketiminate)(pyrrolecarbaldsecbutyliminate) palladium (II);
(N,N'-diethyl-2,4-pentanediketiminate)(pyrrolecarbaldisobutyliminate) palladium (II);
(N,N'-diethyl-2,4-pentanediketiminate)(pyrrolecarbaldtertbutyliminate) palladium (II);
(N,N'-diethyl-2,4-pentanediketiminate)(pyrrolecarbaldtrimethylsilyliminate) palladium (II);
(N,N'-diisopropyl-2,4-pentanediketiminate)(pyrrolecarbaldiminate) palladium(II);
(N,N'-diisopropyl-2,4-pentanediketiminate)(pyrrolecarbaldmethyliminate) palladium (II);
(N,N'-diisopropyl-2,4-pentanediketiminate)(pyrrolecarbaldethyliminate) palladium (II);
(N,N'-diisopropyl-2,4-pentanediketiminate)(pyrrolecarbaldisopropyliminate) palladium(II);
(N,N'-diisopropyl-2,4-pentanediketiminate)(pyrrolecarbaldpropyliminate) palladium (II);
(N,N'-diisopropyl-2,4-pentanediketiminate)(pyrrolecarbaldnbutyliminate) palladium (II);
(N,N'-diisopropyl-2,4-pentanediketiminate)(pyrrolecarbaldsecbutyliminate) palladium (II);
(N,N'-diisopropyl-2,4-pentanediketiminate)(pyrrolecarbaldisobutyliminate) palladium (II);
(N,N'-diisopropyl-2,4-pentanediketiminate)(pyrrolecarbaldtertbutyliminate) palladium (II);
(N,N'-diisopropyl-2,4-pentanediketiminate)(pyrrolecarbaldtrimethylsilyliminate) palladium (II),
(N,N'-dipropyl-2,4-pentanediketiminate)(pyrrolecarbaldiminate) palladium(II);
(N,N'-dipropyl-2,4-pentanediketiminate)(pyrrolecarbaldmethyliminate) palladium (II);
(N,N'-dipropyl-2,4-pentanediketiminate)(pyrrolecarbaldethyliminate) palladium (II);
(N,N'-dipropyl-2,4-pentanediketiminate)(pyrrolecarbaldisopropyliminate) palladium(II);
(N,N'-dipropyl-2,4-pentanediketiminate)(pyrrolecarbaldpropyliminate) palladium (II);
(N,N'-dipropyl-2,4-pentanediketiminate)(pyrrolecarbaldnbutyliminate) palladium (II);
(N,N'-dipropyl-2,4-pentanediketiminate)(pyrrolecarbaldsecbutyliminate) palladium (II);
(N,N'-dipropyl-2,4-pentanediketiminate)(pyrrolecarbaldisobutyliminate) palladium (II);
(N,N'-dipropyl-2,4-pentanediketiminate)(pyrrolecarbaldtertbutyliminate) palladium (II);
(N,N'-dipropyl-2,4-pentanediketiminate)(pyrrolecarbaldtrimethylsilyliminate) palladium (II),
(N,N'-di-tert-butyl-2,4-pentanediketiminate)(pyrrolecarbaldiminate) palladium (II);
(N,N'-di-tert-butyl-2,4-pentanediketiminate)(pyrrolecarbaldmethyliminate) palladium (II);
(N,N'-di-tert-butyl-2,4-pentanediketiminate)(pyrrolecarbaldethyliminate) palladium (II);
(N,N'-di-tert-butyl-2,4-pentanediketiminate)(pyrrolecarbaldisopropyliminate) palladium(II);
(N,N'-di-tert-butyl-2,4-pentanediketiminate)(pyrrolecarbaldpropyliminate) palladium (II);
(N,N'-di-tert-butyl-2,4-pentanediketiminate)(pyrrolecarbaldnbutyliminate) palladium (II);
(N,N'-di-tert-butyl-2,4-pentanediketiminate)(pyrrolecarbaldsecbutyliminate) palladium (II),
(N,N'-di-tert-butyl-2,4-pentanediketiminate)(pyrrolecarbaldisobutyliminate) palladium (II);
(N,N'-di-tert-butyl-2,4-pentanediketiminate)(pyrrolecarbaldtertbutyliminate) palladium (II),
(N,N'-di-tert-butyl-2,4-pentanediketiminate)(pyrrolecarbaldtrimethylsilyliminate)palladium (II);
(N,N'-diisopropylformamidinate)(pyrrolecarbaldiminate) palladium(II);
(N,N'-diisopropylformamidinate)(pyrrolecarbaldmethyliminate) palladium (II);
(N,N'-diisopropylformamidinate)(pyrrolecarbaldethyliminate) palladium (II);
(N,N'-diisopropylformamidinate)(pyrrolecarbaldisopropyliminate) palladium(II);
(N,N'-diisopropylformamidinate)(pyrrolecarbaldpropyliminate) palladium (II);
(N,N'-diisopropylformamidinate)(pyrrolecarbaldnbutyliminate) palladium (II);
(N,N'-diisopropylformamidinate)(pyrrolecarbaldsecbutyliminate) palladium (II);
(N,N'-diisopropylformamidinate)(pyrrolecarbaldisobutyliminate) palladium (II);

(N,N'-diisopropylformamidinate)(pyrrolecarbaldtertbutyliminate) palladium (II);
(N,N'-diisopropylformamidinate)(pyrrolecarbaldtrimethylsilyliminate) palladium (II);
(N,N'-diisopropylacetamidinate)(pyrrolecarbaldiminate) palladium(II);
(N,N'-diisopropylacetamidinate)(pyrrolecarbaldmethyliminate) palladium (II);
(N,N'-diisopropylacetamidinate)(pyrrolecarbaldethyliminate) palladium (II);
(N,N'-diisopropylacetamidinate)(pyrrolecarbaldisopropyliminate) palladium(II);
(N,N'-diisopropylacetamidinate)(pyrrolecarbaldpropyliminate) palladium (II);
(N,N'-diisopropylacetamidinate)(pyrrolecarbaldnbutyliminate) palladium (II);
(N,N'-diisopropylacetamidinate)(pyrrolecarbaldsecbutyliminate) palladium (II);
(N,N'-diisopropylacetamidinate)(pyrrolecarbaldisobutyliminate) palladium (II);
(N,N'-diisopropylacetamidinate)(pyrrolecarbaldtertbutyliminate) palladium (II);
(N,N'-diisopropylacetamidinate)(pyrrolecarbaldtrimethylsilyliminate) palladium (II);
(N,N'-diisopropyl-N,N'-dimethylguanidinate)(pyrrolecarbaldiminate) palladium(II);
(N,N'-diisopropyl-N,N'-dimethylguanidinate)(pyrrolecarbaldmethyliminate) palladium (II);
(N,N'-diisopropyl-N,N'-dimethylguanidinate)(pyrrolecarbaldethyliminate) palladium (II);
(N,N'-diisopropyl-N,N'-dimethylguanidinate)(pyrrolecarbaldisopropyliminate) palladium(II);
(N,N'-diisopropyl-N,N'-dimethylguanidinate)(pyrrolecarbaldpropyliminate) palladium (II);
(N,N'-diisopropyl-N,N'-dimethylguanidinate)(pyrrolecarbaldnbutyliminate) palladium (II);
(N,N'-diisopropyl-N,N'-dimethylguanidinate)(pyrrolecarbaldsecbutyliminate) palladium (II);
(N,N'-diisopropyl-N,N'-dimethylguanidinate)(pyrrolecarbaldisobutyliminate) palladium (II);
(N,N'-diisopropyl-N,N'-dimethylguanidinate)(pyrrolecarbaldtertbutyliminate) palladium (II);
(N,N'-diisopropyl-N,N'-dimethylguanidinate)(pyrrolecarbaldtrimethylsilyliminate) palladium (II);
(N,N'-2,4-pentanediketiminate)(pyrrolecarbaldiminate) platinum(II);
(N,N'-2,4-pentanediketiminate)(pyrrolecarbaldmethyliminate) platinum (II);
(N,N'-2,4-pentanediketiminate)(pyrrolecarbaldethyliminate) platinum (II);
(N,N'-2,4-pentanediketiminate)(pyrrolecarbaldisopropyliminate) platinum (II);
(N,N'-2,4-pentanediketiminate)(pyrrolecarbaldpropyliminate) platinum (II);
(N,N'-2,4-pentanediketiminate)(pyrrolecarbaldnbutyliminate) platinum (II);
(N,N'-2,4-pentanediketiminate)(pyrrolecarbaldsecbutyliminate) platinum (II);
(N,N'-2,4-pentanediketiminate)(pyrrolecarbaldisobutyliminate) platinum (II);
(N,N'-2,4-pentanediketiminate)(pyrrolecarbaldtertbutyliminate) platinum (II);
(N,N'-2,4-pentanediketiminate)(pyrrolecarbaldtrimethylsilyliminate) platinum (II);
(N,N'-dimethyl-2,4-pentanediketiminate)(pyrrolecarbaldiminate) platinum (II);
(N,N'-dimethyl-2,4-pentanediketiminate)(pyrrolecarbaldmethyliminate) platinum (II);
(N,N'-dimethyl-2,4-pentanediketiminate)(pyrrolecarbaldethyliminate) platinum (II);
(N,N'-dimethyl-2,4-pentanediketiminate)(pyrrolecarbaldisopropyliminate) platinum (II);
(N,N'-dimethyl-2,4-pentanediketiminate)(pyrrolecarbaldpropyliminate) platinum (II);
(N,N'-dimethyl-2,4-pentanediketiminate)(pyrrolecarbaldnbutyliminate) platinum (II);
(N,N'-dimethyl-2,4-pentanediketiminate)(pyrrolecarbaldsecbutyliminate) platinum (II);
(N,N'-dimethyl-2,4-pentanediketiminate)(pyrrolecarbaldisobutyliminate) platinum (II);
(N,N'-dimethyl-2,4-pentanediketiminate)(pyrrolecarbaldtertbutyliminate) platinum (II);
(N,N'-dimethyl-2,4-pentanediketiminate)(pyrrolecarbaldtrimethylsilyliminate) platinum (II);
(N,N'-diethyl-2,4-pentanediketiminate)(pyrrolecarbaldiminate) platinum (II);
(N,N'-diethyl-2,4-pentanediketiminate)(pyrrolecarbaldmethyliminate) platinum (II);
(N,N'-diethyl-2,4-pentanediketiminate)(pyrrolecarbaldethyliminate) platinum (II);
(N,N'-diethyl-2,4-pentanediketiminate)(pyrrolecarbaldisopropyliminate) platinum (II);
(N,N'-diethyl-2,4-pentanediketiminate)(pyrrolecarbaldpropyliminate) platinum (II);
(N,N'-diethyl-2,4-pentanediketiminate)(pyrrolecarbaldnbutyliminate) platinum (II);
(N,N'-diethyl-2,4-pentanediketiminate)(pyrrolecarbaldsecbutyliminate) platinum (II);
(N,N'-diethyl-2,4-pentanediketiminate)(pyrrolecarbaldisobutyliminate) platinum (II);
(N,N'-diethyl-2,4-pentanediketiminate)(pyrrolecarbaldtertbutyliminate) platinum (II);
(N,N'-diethyl-2,4-pentanediketiminate)(pyrrolecarbaldtrimethylsilyliminate) platinum (II);
(N,N'-diisopropyl-2,4-pentanediketiminate)(pyrrolecarbaldiminate) platinum (II);
(N,N'-diisopropyl-2,4-pentanediketiminate)(pyrrolecarbaldmethyliminate) platinum (II);
(N,N'-diisopropyl-2,4-pentanediketiminate)(pyrrolecarbaldethyliminate) platinum (II);
(N,N'-diisopropyl-2,4-pentanediketiminate)(pyrrolecarbaldisopropyliminate) platinum (II);
(N,N'-diisopropyl-2,4-pentanediketiminate)(pyrrolecarbaldpropyliminate) platinum (II);
(N,N'-diisopropyl-2,4-pentanediketiminate)(pyrrolecarbaldnbutyliminate) platinum (II);
(N,N'-diisopropyl-2,4-pentanediketiminate)(pyrrolecarbaldsecbutyliminate) platinum (II);
(N,N'-diisopropyl-2,4-pentanediketiminate)(pyrrolecarbaldisobutyliminate) platinum (II);
(N,N'-diisopropyl-2,4-pentanediketiminate)(pyrrolecarbaldtertbutyliminate) platinum (II);
(N,N'-diisopropyl-2,4-pentanediketiminate)(pyrrolecarbaldtrimethylsilyliminate) platinum (II);
(N,N'-dipropyl-2,4-pentanediketiminate)(pyrrolecarbaldiminate) platinum (II);
(N,N'-dipropyl-2,4-pentanediketiminate)(pyrrolecarbaldmethyliminate) platinum (II);
(N,N'-dipropyl-2,4-pentanediketiminate)(pyrrolecarbaldethyliminate) platinum (II);
(N,N'-dipropyl-2,4-pentanediketiminate)(pyrrolecarbaldisopropyliminate) platinum (II);

(N,N'-dipropyl-2,4-pentanediketiminate)(pyrrolecarbaldpropyliminate) platinum (II);
(N,N'-dipropyl-2,4-pentanediketiminate)(pyrrolecarbaldnbutyliminate) platinum (II);
(N,N'-dipropyl-2,4-pentanediketiminate)(pyrrolecarbaldsecbutyliminate) platinum (II);
(N,N'-dipropyl-2,4-pentanediketiminate)(pyrrolecarbaldisobutyliminate) platinum (II);
(N,N'-dipropyl-2,4-pentanediketiminate)(pyrrolecarbaldtertbutyliminate) platinum (II);
(N,N'-dipropyl-2,4-pentanediketiminate)(pyrrolecarbaldtrimethylsilyliminate) platinum (II);
(N,N'-di-tert-butyl-2,4-pentanediketiminate)(pyrrolecarbaldiminate) platinum (II);
(N,N'-di-tert-butyl-2,4-pentanediketiminate)(pyrrolecarbaldmethyliminate) platinum (II);
(N,N'-di-tert-butyl-2,4-pentanediketiminate)(pyrrolecarbaldethyliminate) platinum (II);
(N,N'-di-tert-butyl-2,4-pentanediketiminate)(pyrrolecarbaldisopropyliminate) platinum (II);
(N,N'-di-tert-butyl-2,4-pentanediketiminate)(pyrrolecarbaldpropyliminate) platinum (II);
(N,N'-di-tert-butyl-2,4-pentanediketiminate)(pyrrolecarbaldnbutyliminate) platinum (II);
(N,N'-di-tert-butyl-2,4-pentanediketiminate)(pyrrolecarbaldsecbutyliminate) platinum (II);
(N,N'-di-tert-butyl-2,4-pentanediketiminate)(pyrrolecarbaldisobutyliminate) platinum (II);
(N,N'-di-tert-butyl-2,4-pentanediketiminate)(pyrrolecarbaldtertbutyliminate) platinum (II);
(N,N'-di-tert-butyl-2,4-pentanediketiminate)(pyrrolecarbaldtrimethylsilyliminate) platinum (II);
(N,N'-diisopropylformamidinate)(pyrrolecarbaldiminate) platinum (II);
(N,N'-diisopropylformamidinate)(pyrrolecarbaldmethyliminate) platinum (II);
(N,N'-diisopropylformamidinate)(pyrrolecarbaldethyliminate) platinum (II);
(N,N'-diisopropylformamidinate)(pyrrolecarbaldisopropyliminate) platinum (II);
(N,N'-diisopropylformamidinate)(pyrrolecarbaldpropyliminate) platinum (II);
(N,N'-diisopropylformamidinate)(pyrrolecarbaldnbutyliminate) platinum (II);
(N,N'-diisopropylformamidinate)(pyrrolecarbaldsecbutyliminate) platinum (II);
(N,N'-diisopropylformamidinate)(pyrrolecarbaldisobutyliminate) platinum (II);
(N,N'-diisopropylformamidinate)(pyrrolecarbaldtertbutyliminate) platinum (II);
(N,N'-diisopropylformamidinate)(pyrrolecarbaldtrimethylsilyliminate) platinum (II);
(N,N'-diisopropylacetamidinate)(pyrrolecarbaldiminate) platinum (II);
(N,N'-diisopropylacetamidinate)(pyrrolecarbaldmethyliminate) platinum (II);
(N,N'-diisopropylacetamidinate)(pyrrolecarbaldethyliminate) platinum (II);
(N,N'-diisopropylacetamidinate)(pyrrolecarbaldisopropyliminate) platinum (II);
(N,N'-diisopropylacetamidinate)(pyrrolecarbaldpropyliminate) platinum (II);
(N,N'-diisopropylacetamidinate)(pyrrolecarbaldnbutyliminate) platinum (II);
(N,N'-diisopropylacetamidinate)(pyrrolecarbaldsecbutyliminate) platinum (II);
(N,N'-diisopropylacetamidinate)(pyrrolecarbaldisobutyliminate) platinum (II);
(N,N'-diisopropylacetamidinate)(pyrrolecarbaldtertbutyliminate) platinum (II);
(N,N'-diisopropylacetamidinate)(pyrrolecarbaldtrimethylsilyliminate) platinum (II);
(N,N'-diisopropyl-N,N'-dimethylguanidinate)(pyrrolecarbaldiminate) platinum (II);
(N,N'-diisopropyl-N,N'-dimethylguanidinate)(pyrrolecarbaldmethyliminate) platinum (II);
(N,N'-diisopropyl-N,N'-dimethylguanidinate)(pyrrolecarbaldethyliminate) platinum (II);
(N,N'-diisopropyl-N,N'-dimethylguanidinate)(pyrrolecarbaldisopropyliminate) platinum (II);
(N,N'-diisopropyl-N,N'-dimethylguanidinate)(pyrrolecarbaldpropyliminate) platinum (II);
(N,N'-diisopropyl-N,N'-dimethylguanidinate)(pyrrolecarbaldnbutyliminate) platinum (II);
(N,N'-diisopropyl-N,N'-dimethylguanidinate)(pyrrolecarbaldsecbutyliminate) platinum (II);
(N,N'-diisopropyl-N,N'-dimethylguanidinate)(pyrrolecarbaldisobutyliminate) platinum (II);
(N,N'-diisopropyl-N,N'-dimethylguanidinate)(pyrrolecarbaldtertbutyliminate) platinum (II);
(N,N'-diisopropyl-N,N'-dimethylguanidinate)(pyrrolecarbaldtrimethylsilyliminate) platinum (II);
(N,N'-2,4-pentanediketiminate)(pyrrolecarbaldiminate) ruthenium (II);
(N,N'-2,4-pentanediketiminate)(pyrrolecarbaldmethyliminate) ruthenium (II);
(N,N'-2,4-pentanediketiminate)(pyrrolecarbaldethyliminate) ruthenium (II);
(N,N'-2,4-pentanediketiminate)(pyrrolecarbaldisopropyliminate) ruthenium (II);
(N,N'-2,4-pentanediketiminate)(pyrrolecarbaldpropyliminate) ruthenium (II);
(N,N'-2,4-pentanediketiminate)(pyrrolecarbaldnbutyliminate) ruthenium (II);
(N,N'-2,4-pentanediketiminate)(pyrrolecarbaldsecbutyliminate) ruthenium (II);
(N,N'-2,4-pentanediketiminate)(pyrrolecarbaldisobutyliminate) ruthenium (II);
(N,N'-2,4-pentanediketiminate)(pyrrolecarbaldtertbutyliminate) ruthenium (II);
(N,N'-2,4-pentanediketiminate)(pyrrolecarbaldtrimethylsilyliminate) ruthenium (II);
(N,N'-dimethyl-2,4-pentanediketiminate)(pyrrolecarbaldiminate) ruthenium (II);
(N,N'-dimethyl-2,4-pentanediketiminate)(pyrrolecarbaldmethyliminate) ruthenium (II);
(N,N'-dimethyl-2,4-pentanediketiminate)(pyrrolecarbaldethyliminate) ruthenium (II);
(N,N'-dimethyl-2,4-pentanediketiminate)(pyrrolecarbaldisopropyliminate) ruthenium (II);
(N,N'-dimethyl-2,4-pentanediketiminate)(pyrrolecarbaldpropyliminate) ruthenium (II);
(N,N'-dimethyl-2,4-pentanediketiminate)(pyrrolecarbaldnbutyliminate) ruthenium (II);
(N,N'-dimethyl-2,4-pentanediketiminate)(pyrrolecarbaldsecbutyliminate) ruthenium (II);
(N,N'-dimethyl-2,4-pentanediketiminate)(pyrrolecarbaldisobutyliminate) ruthenium (II);
(N,N'-dimethyl-2,4-pentanediketiminate)(pyrrolecarbaldtertbutyliminate) ruthenium (II);
(N,N'-dimethyl-2,4-pentanediketiminate)(pyrrolecarbaldtrimethylsilyliminate) ruthenium (II);

(N,N'-diethyl-2,4-pentanediketiminate)(pyrrolecarbaldiminate) ruthenium (II);
(N,N'-diethyl-2,4-pentanediketiminate)(pyrrolecarbaldmethyliminate) ruthenium (II);
(N,N'-diethyl-2,4-pentanediketiminate)(pyrrolecarbaldethyliminate) ruthenium (II);
(N,N'-diethyl-2,4-pentanediketiminate)(pyrrolecarbaldisopropyliminate) ruthenium (II);
(N,N'-diethyl-2,4-pentanediketiminate)(pyrrolecarbaldpropyliminate) ruthenium (II);
(N,N'-diethyl-2,4-pentanediketiminate)(pyrrolecarbaldnbutyliminate) ruthenium (II);
(N,N'-diethyl-2,4-pentanediketiminate)(pyrrolecarbaldsecbutyliminate) ruthenium (II);
(N,N'-diethyl-2,4-pentanediketiminate)(pyrrolecarbaldisobutyliminate) ruthenium (II);
(N,N'-diethyl-2,4-pentanediketiminate)(pyrrolecarbaldtertbutyliminate) ruthenium (II);
(N,N'-diethyl-2,4-pentanediketiminate)(pyrrolecarbaldtrimethylsilyliminate) ruthenium (II);
(N,N'-diisopropyl-2,4-pentanediketiminate)(pyrrolecarbaldiminate) ruthenium (II);
(N,N'-diisopropyl-2,4-pentanediketiminate)(pyrrolecarbaldmethyliminate) ruthenium (II);
(N,N'-diisopropyl-2,4-pentanediketiminate)(pyrrolecarbaldethyliminate) ruthenium (II);
(N,N'-diisopropyl-2,4-pentanediketiminate)(pyrrolecarbaldisopropyliminate) ruthenium (II);
(N,N'-diisopropyl-2,4-pentanediketiminate)(pyrrolecarbaldpropyliminate) ruthenium (II);
(N,N'-diisopropyl-2,4-pentanediketiminate)(pyrrolecarbaldnbutyliminate) ruthenium (II);
(N,N'-diisopropyl-2,4-pentanediketiminate)(pyrrolecarbaldsecbutyliminate) ruthenium (II);
(N,N'-diisopropyl-2,4-pentanediketiminate)(pyrrolecarbaldisobutyliminate) ruthenium (II);
(N,N'-diisopropyl-2,4-pentanediketiminate)(pyrrolecarbaldtertbutyliminate) ruthenium (II);
(N,N'-diisopropyl-2,4-pentanediketiminate)(pyrrolecarbaldtrimethylsilyliminate) ruthenium (II);
(N,N'-dipropyl-2,4-pentanediketiminate)(pyrrolecarbaldiminate) ruthenium (II);
(N,N'-dipropyl-2,4-pentanediketiminate)(pyrrolecarbaldmethyliminate) ruthenium (II);
(N,N'-dipropyl-2,4-pentanediketiminate)(pyrrolecarbaldethyliminate) ruthenium (II);
(N,N'-dipropyl-2,4-pentanediketiminate)(pyrrolecarbaldisopropyliminate) ruthenium (II);
(N,N'-dipropyl-2,4-pentanediketiminate)(pyrrolecarbaldpropyliminate) ruthenium (II);
(N,N'-dipropyl-2,4-pentanediketiminate)(pyrrolecarbaldnbutyliminate) ruthenium (II);
(N,N'-dipropyl-2,4-pentanediketiminate)(pyrrolecarbaldsecbutyliminate) ruthenium (II);
(N,N'-dipropyl-2,4-pentanediketiminate)(pyrrolecarbaldisobutyliminate) ruthenium (II);
(N,N'-dipropyl-2,4-pentanediketiminate)(pyrrolecarbaldtertbutyliminate) ruthenium (II);
(N,N'-dipropyl-2,4-pentanediketiminate)(pyrrolecarbaldtrimethylsilyliminate) ruthenium (II);
(N,N'-di-tert-butyl-2,4-pentanediketiminate)(pyrrolecarbaldiminate) ruthenium (II);
(N,N'-di-tert-butyl-2,4-pentanediketiminate)(pyrrolecarbaldmethyliminate) ruthenium (II);
(N,N'-di-tert-butyl-2,4-pentanediketiminate)(pyrrolecarbaldethyliminate) ruthenium (II);
(N,N'-di-tert-butyl-2,4-pentanediketiminate)(pyrrolecarbaldisopropyliminate) ruthenium (II);
(N,N'-di-tert-butyl-2,4-pentanediketiminate)(pyrrolecarbaldpropyliminate) ruthenium (II);
(N,N'-di-tert-butyl-2,4-pentanediketiminate)(pyrrolecarbaldnbutyliminate) ruthenium (II);
(N,N'-di-tert-butyl-2,4-pentanediketiminate)(pyrrolecarbaldsecbutyliminate) ruthenium (II);
(N,N'-di-tert-butyl-2,4-pentanediketiminate)(pyrrolecarbaldisobutyliminate) ruthenium (II);
(N,N'-di-tert-butyl-2,4-pentanediketiminate)(pyrrolecarbaldtertbutyliminate) ruthenium (II);
(N,N'-di-tert-butyl-2,4-pentanediketiminate)(pyrrolecarbaldtrimethylsilyliminate) ruthenium (II);
(N,N'-diisopropylformamidinate)(pyrrolecarbaldiminate) ruthenium (II);
(N,N'-diisopropylformamidinate)(pyrrolecarbaldmethyliminate) ruthenium (II);
(N,N'-diisopropylformamidinate)(pyrrolecarbaldethyliminate) ruthenium (II);
(N,N'-diisopropylformamidinate)(pyrrolecarbaldisopropyliminate) ruthenium (II);
(N,N'-diisopropylformamidinate)(pyrrolecarbaldpropyliminate) ruthenium (II);
(N,N'-diisopropylformamidinate)(pyrrolecarbaldnbutyliminate) ruthenium (II);
(N,N'-diisopropylformamidinate)(pyrrolecarbaldsecbutyliminate) ruthenium (II);
(N,N'-diisopropylformamidinate)(pyrrolecarbaldisobutyliminate) ruthenium (II);
(N,N'-diisopropylformamidinate)(pyrrolecarbaldtertbutyliminate) ruthenium (II);
(N,N'-diisopropylformamidinate)(pyrrolecarbaldtrimethylsilyliminate) ruthenium (II);
(N,N'-diisopropylacetamidinate)(pyrrolecarbaldiminate) ruthenium (II);
(N,N'-diisopropylacetamidinate)(pyrrolecarbaldmethyliminate) ruthenium (II);
(N,N'-diisopropylacetamidinate)(pyrrolecarbaldethyliminate) ruthenium (II);
(N,N'-diisopropylacetamidinate)(pyrrolecarbaldisopropyliminate) ruthenium (II);
(N,N'-diisopropylacetamidinate)(pyrrolecarbaldpropyliminate) ruthenium (II);
(N,N'-diisopropylacetamidinate)(pyrrolecarbaldnbutyliminate) ruthenium (II);
(N,N'-diisopropylacetamidinate)(pyrrolecarbaldsecbutyliminate) ruthenium (II);
(N,N'-diisopropylacetamidinate)(pyrrolecarbaldisobutyliminate) ruthenium (II);
(N,N'-diisopropylacetamidinate)(pyrrolecarbaldtertbutyliminate) ruthenium (II);
(N,N'-diisopropylacetamidinate)(pyrrolecarbaldtrimethylsilyliminate) ruthenium (II);
(N,N'-diisopropyl-N,N'-dimethylguanidinate)(pyrrolecarbaldiminate) ruthenium (II);
(N,N'-diisopropyl-N,N'-dimethylguanidinate)(pyrrolecarbaldmethyliminate) ruthenium (II);
(N,N'-diisopropyl-N,N'-dimethylguanidinate)(pyrrolecarbaldethyliminate) ruthenium (II);
(N,N'-diisopropyl-N,N'-dimethylguanidinate)(pyrrolecarbaldisopropyliminate) ruthenium (II);
(N,N'-diisopropyl-N,N'-dimethylguanidinate)(pyrrolecarbaldpropyliminate) ruthenium (II);
(N,N'-diisopropyl-N,N'-dimethylguanidinate)(pyrrolecarbaldnbutyliminate) ruthenium (II);

(N,N'-diisopropyl-N,N'-dimethylguanidinate)(pyrrolecarbaldsecbutyliminate) ruthenium (II);
(N,N'-diisopropyl-N,N'-dimethylguanidinate)(pyrrolecarbaldisobutyliminate) ruthenium (II);
(N,N'-diisopropyl-N,N'-dimethylguanidinate)(pyrrolecarbaldtertbutyliminate) ruthenium (II); and
(N,N'-diisopropyl-N,N'-dimethylguanidinate)(pyrrolecarbaldtrimethylsilyliminate) ruthenium (II).

3. The precursor of claim 2, selected from the group consisting of: (N,N'-diisopropylacetamidinate)(pyrrolylcarbaldisopropyliminate) palladium (II); (N,N'-diisopropylacetamidinate)(pyrrolylcarbaldisopropyliminate) platinum (II); and (N,N'-diisopropylacetamidinate)(pyrrolylcarbaldisopropyliminate) ruthenium (II).

4. A process for the deposition of a metalloid-containing film on a substrate, comprising the steps of:
introducing at least one metalloid-containing precursor into a reactor having at least one substrate disposed therein, the at least one metalloid-containing precursor having one of the following formula:

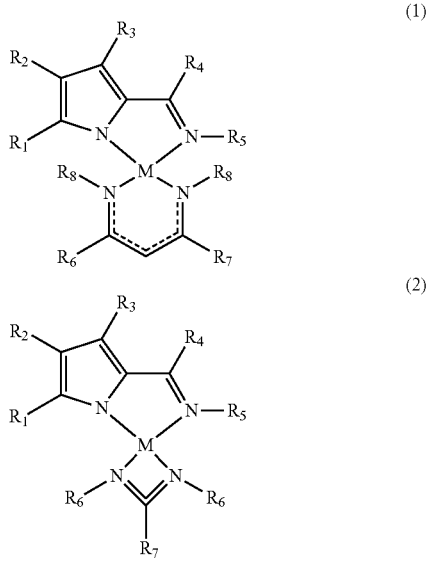

wherein:
M is an element selected from the group consisting of Pd, Pt, and Ru; and
each of $R_1$, $R_2$, $R_3$, $R_4$, $R_5$, $R_6$, $R_7$ and $R_8$ is independently selected from H; a C1-C4 linear, branched, or cyclic alkyl group; a C1-C4 linear, branched, or cyclic alkylsilyl group (mono, bis, or tris alkyl); a C1-C4 linear, branched, or cyclic alkylamino group; or
a C1-C4 linear, branched, or cyclic fluoroalkyl group; and
depositing at least part of the metalloid-containing precursor onto the at least one substrate to form the metalloid-containing film.

5. The process of claim 4, further comprising introducing at least one reactant into the reactor, wherein the reactant is selected from the croup consisting of $H_2$, $NH_3$, $SiH_4$, $Si_2H_6$, $Si_3H_8$, $SiH_2Me_2$, $SiH_2Et_2$, $N(SiH_3)_3$, hydrogen radicals thereof $O_2$, $O_3$, $H_2O$, NO, $N_2O$, oxygen radicals thereof, and mixtures thereof.

6. The process of claim 5, wherein the reactant is selected from the group consisting of $H_2$, $NH_3$, $SiH_4$, $Si_2H_6$, $Si_3H_8$, $SiH_2Me_2$, $SiH_2Et_2$, $N(SiH_3)_3$, hydrogen radicals thereof, and mixtures thereof.

7. The process of claim 5, wherein the reactant is selected from the group consisting of: $O_2$, $O_3$, $H_2O$, NO, $N_2O$, oxygen radicals thereof, and mixtures thereof.

8. The process of claim 5, wherein the metalloid-containing precursor and the reactant are introduced into the reactor substantially simultaneously and the reactor is configured for chemical vapor deposition.

9. The process of claim 8, wherein the reactor is configured for plasma enhanced chemical vapor deposition.

10. The process of claim 5, wherein the metalloid-containing precursor and the reactant are introduced into the chamber sequentially and the reactor is configured for atomic layer deposition.

11. The process of claim 10, wherein the reactor is configured for plasma enhanced atomic layer deposition.

12. The process of claim 4, wherein the metalloid-containing precursor is selected from the group consisting of:
(N,N'-2,4-pentanediketiminate)(pyrrolecarbaldiminate) palladium(II);
(N,N'-2,4-pentanediketiminate)(pyrrolecarbaldmethyliminate) palladium (II);
(N,N'-2,4-pentanediketiminate)(pyrrolecarbaldethyliminate) palladium (II);
(N,N'-2,4-pentanediketiminate)(pyrrolecarbaldisopropyliminate) palladium(II);
(N,N'-2,4-pentanediketiminate)(pyrrolecarbaldpropyliminate) palladium (II);
(N,N'-2,4-pentanediketiminate)(pyrrolecarbaldnbutyliminate) palladium (II);
(N,N'-2,4-pentanediketiminate)(pyrrolecarbaldsecbutyliminate) palladium (II);
(N,N'-2,4-pentanediketiminate)(pyrrolecarbaldisobutyliminate) palladium (II);
(N,N'-2,4-pentanediketiminate)(pyrrolecarbaldtertbutyliminate) palladium (II);
(N,N'-2,4-pentanediketiminate)(pyrrolecarbaldtrimethylsilyliminate) palladium (II);
(N,N'-dimethyl-2,4-pentanediketiminate)(pyrrolecarbaldiminate) palladium(II);
(N,N'-dimethyl-2,4-pentanediketiminate)(pyrrolecarbaldmethyliminate) palladium (II);
(N,N'-dimethyl-2,4-pentanediketiminate)(pyrrolecarbaldethyliminate) palladium (II);
(N,N'-dimethyl-2,4-pentanediketiminate)(pyrrolecarbaldisopropyliminate) palladium(II);
(N,N'-dimethyl-2,4-pentanediketiminate)(pyrrolecarbaldpropyliminate) palladium (II);
(N,N'-dimethyl-2,4-pentanediketiminate)(pyrrolecarbaldnbutyliminate) palladium (II);
(N,N'-dimethyl-2,4-pentanediketiminate)(pyrrolecarbaldsecbutyliminate) palladium (II);
(N,N'-dimethyl-2,4-pentanediketiminate)(pyrrolecarbaldisobutyliminate) palladium (II);
(N,N'-dimethyl-2,4-pentanediketiminate)(pyrrolecarbaldtertbutyliminate) palladium (II);
(N,N'-dimethyl-2,4-pentanediketiminate)(pyrrolecarbaldtrimethylsilyliminate) palladium (II);
(N,N'-diethyl-2,4-pentanediketiminate)(pyrrolecarbaldiminate) palladium(II);
(N,N'-diethyl-2,4-pentanediketiminate)(pyrrolecarbaldmethyliminate) palladium (II);
(N,N'-diethyl-2,4-pentanediketiminate)(pyrrolecarbaldethyliminate) palladium (II);
(N,N'-diethyl-2,4-pentanediketiminate)(pyrrolecarbaldisopropyliminate) palladium(II);
(N,N'-diethyl-2,4-pentanediketiminate)(pyrrolecarbaldpropyliminate) palladium (II);

(N,N'-diethyl-2,4-pentanediketiminate)(pyrrolecarbaldnbutyliminate) palladium (II);
(N,N'-diethyl-2,4-pentanediketiminate)(pyrrolecarbaldsecbutyliminate) palladium (II);
(N,N'-diethyl-2,4-pentanediketiminate)(pyrrolecarbaldisobutyliminate) palladium (II);
(N,N'-diethyl-2,4-pentanediketiminate)(pyrrolecarbaldtertbutyliminate) palladium (II);
(N,N'-diethyl-2,4-pentanediketiminate)(pyrrolecarbaldtrimethylsilyliminate) palladium (II);
(N,N'-diisopropyl-2,4-pentanediketiminate)(pyrrolecarbaldiminate) palladium(II);
(N,N'-diisopropyl-2,4-pentanediketiminate)(pyrrolecarbaldmethyliminate) palladium (II);
(N,N'-diisopropyl-2,4-pentanediketiminate)(pyrrolecarbaldethyliminate) palladium (II);
(N,N'-diisopropyl-2,4-pentanediketiminate)(pyrrolecarbaldisopropyliminate) palladium(II);
(N,N'-diisopropyl-2,4-pentanediketiminate)(pyrrolecarbaldpropyliminate) palladium (II);
(N,N'-diisopropyl-2,4-pentanediketiminate)(pyrrolecarbaldnbutyliminate) palladium (II);
(N,N'-diisopropyl-2,4-pentanediketiminate)(pyrrolecarbaldsecbutyliminate) palladium (II);
(N,N'-diisopropyl-2,4-pentanediketiminate)(pyrrolecarbaldisobutyliminate) palladium (II);
(N,N'-diisopropyl-2,4-pentanediketiminate)(pyrrolecarbaldtertbutyliminate) palladium (II);
(N,N'-diisopropyl-2,4-pentanediketiminate)(pyrrolecarbaldtrimethylsilyliminate)palladium (II);
(N,N'-dipropyl-2,4-pentanediketiminate)(pyrrolecarbaldiminate) palladium(II);
(N,N'-dipropyl-2,4-pentanediketiminate)(pyrrolecarbaldmethyliminate) palladium (II);
(N,N'-dipropyl-2,4-pentanediketiminate)(pyrrolecarbaldethyliminate) palladium (II);
(N,N'-dipropyl-2,4-pentanediketiminate)(pyrrolecarbaldisopropyliminate) palladium(II);
(N,N'-dipropyl-2,4-pentanediketiminate)(pyrrolecarbaldpropyliminate) palladium (II);
(N,N'-dipropyl-2,4-pentanediketiminate)(pyrrolecarbaldnbutyliminate) palladium (II);
(N,N'-dipropyl-2,4-pentanediketiminate)(pyrrolecarbaldsecbutyliminate) palladium (II);
(N,N'-dipropyl-2,4-pentanediketiminate)(pyrrolecarbaldisobutyliminate) palladium (II);
(N,N'-dipropyl-2,4-pentanediketiminate)(pyrrolecarbaldtertbutyliminate) palladium (II);
(N,N'-dipropyl-2,4-pentanediketiminate)(pyrrolecarbaldtrimethylsilyliminate)palladium (II);
(N,N'-di-tert-butyl-2,4-pentanediketiminate)(pyrrolecarbaldiminate) palladium(II);
(N,N'-di-tert-butyl-2,4-pentanediketiminate)(pyrrolecarbaldmethyliminate) palladium (II);
(N,N'-di-tert-butyl-2,4-pentanediketiminate)(pyrrolecarbaldethyliminate) palladium (II);
(N,N'-di-tert-butyl-2,4-pentanediketiminate)(pyrrolecarbaldisopropyliminate) palladium(II);
(N,N'-di-tert-butyl-2,4-pentanediketiminate)(pyrrolecarbaldpropyliminate) palladium (II);
(N,N'-di-tert-butyl-2,4-pentanediketiminate)(pyrrolecarbaldnbutyliminate) palladium (II);
(N,N'-di-tert-butyl-2,4-pentanediketiminate)(pyrrolecarbaldsecbutyliminate) palladium (II);
(N,N'-di-tert-butyl-2,4-pentanediketiminate)(pyrrolecarbaldisobutyliminate) palladium (II);
(N,N'-di-tert-butyl-2,4-pentanediketiminate)(pyrrolecarbaldtertbutyliminate) palladium (II);
(N,N'-di-tert-butyl-2,4-pentanediketiminate)(pyrrolecarbaldtrimethylsilyliminate)palladium (II);
(N,N'-diisopropylformamidinate)(pyrrolecarbaldiminate) palladium(II);
(N,N'-diisopropylformamidinate)(pyrrolecarbaldmethyliminate) palladium (II);
(N,N'-diisopropylformamidinate)(pyrrolecarbaldethyliminate) palladium (II);
(N,N'-diisopropylformamidinate)(pyrrolecarbaldisopropyliminate) palladium(II);
(N,N'-diisopropylformamidinate)(pyrrolecarbaldpropyliminate) palladium (II);
(N,N'-diisopropylformamidinate)(pyrrolecarbaldnbutyliminate) palladium (II);
(N,N'-diisopropylformamidinate)(pyrrolecarbaldsecbutyliminate) palladium (II);
(N,N'-diisopropylformamidinate)(pyrrolecarbaldisobutyliminate) palladium (II);
(N,N'-diisopropylformamidinate)(pyrrolecarbaldtertbutyliminate) palladium (II);
(N,N'-diisopropylformamidinate)(pyrrolecarbaldtrimethylsilyliminate) palladium (II);
(N,N'-diisopropylacetamidinate)(pyrrolecarbaldiminate) palladium(II);
(N,N'-diisopropylacetamidinate)(pyrrolecarbaldmethyliminate) palladium (II);
(N,N'-diisopropylacetamidinate)(pyrrolecarbaldethyliminate) palladium (II);
(N,N'-diisopropylacetamidinate)(pyrrolecarbaldisopropyliminate) palladium(II);
(N,N'-diisopropylacetamidinate)(pyrrolecarbaldpropyliminate) palladium (II);
(N,N'-diisopropylacetamidinate)(pyrrolecarbaldnbutyliminate) palladium (II);
(N,N'-diisopropylacetamidinate)(pyrrolecarbaldsecbutyliminate) palladium (II);
(N,N'-diisopropylacetamidinate)(pyrrolecarbaldisobutyliminate) palladium (II);
(N,N'-diisopropylacetamidinate)(pyrrolecarbaldtertbutyliminate) palladium (II);
(N,N'-diisopropylacetamidinate)(pyrrolecarbaldtrimethylsilyliminate) palladium (II);
(N,N'-diisopropyl-N,N'-dimethylguanidinate)(pyrrolecarbaldiminate) palladium(II);
(N,N'-diisopropyl-N,N'-dimethylguanidinate)(pyrrolecarbaldmethyliminate) palladium (II);
(N,N'-diisopropyl-N,N'-dimethylguanidinate)(pyrrolecarbaldethyliminate) palladium (II);
(N,N'-diisopropyl-N,N'-dimethylguanidinate)(pyrrolecarbaldisopropyliminate) palladium(II);
(N,N'-diisopropyl-N,N'-dimethylguanidinate)(pyrrolecarbaldpropyliminate) palladium (II);
(N,N'-diisopropyl-N,N'-dimethylguanidinate)(pyrrolecarbaldnbutyliminate) palladium (II);
(N,N'-diisopropyl-N,N'-dimethylguanidinate)(pyrrolecarbaldsecbutyliminate) palladium (II);
(N,N'-diisopropyl-N,N'-dimethylguanidinate)(pyrrolecarbaldisobutyliminate) palladium (II);
(N,N'-diisopropyl-N,N'-dimethylguanidinate)(pyrrolecarbaldtertbutyliminate) palladium (II);
(N,N'-diisopropyl-N,N'-dimethylguanidinate)(pyrrolecarbaldtrimethylsilyliminate) palladium (II);
(N,N'-2,4-pentanediketiminate)(pyrrolecarbaldiminate) platinum(II);

(N,N'-2,4-pentanediketiminate)(pyrrolecarbaldmethyliminate) platinum (II);
(N,N'-2,4-pentanediketiminate)(pyrrolecarbaldethyliminate) platinum (II);
(N,N'-2,4-pentanediketiminate)(pyrrolecarbaldisopropyliminate) platinum (II);
(N,N'-2,4-pentanediketiminate)(pyrrolecarbaldpropyliminate) platinum (II);
(N,N'-2,4-pentanediketiminate)(pyrrolecarbaldnbutyliminate) platinum (II);
(N,N'-2,4-pentanediketiminate)(pyrrolecarbaldsecbutyliminate) platinum (II);
(N,N'-2,4-pentanediketiminate)(pyrrolecarbaldisobutyliminate) platinum (II);
(N,N'-2,4-pentanediketiminate)(pyrrolecarbaldtertbutyliminate) platinum (II);
(N,N'-2,4-pentanediketiminate)(pyrrolecarbaldtrimethylsilyliminate) platinum (II);
(N,N'-dimethyl-2,4-pentanediketiminate)(pyrrolecarbaldiminate) platinum (II);
(N,N'-dimethyl-2,4-pentanediketiminate)(pyrrolecarbaldmethyliminate) platinum (II);
(N,N'-dimethyl-2,4-pentanediketiminate)(pyrrolecarbaldethyliminate) platinum (II);
(N,N'-dimethyl-2,4-pentanediketiminate)(pyrrolecarbaldisopropyliminate) platinum (II);
(N,N'-dimethyl-2,4-pentanediketiminate)(pyrrolecarbaldpropyliminate) platinum (II);
(N,N'-dimethyl-2,4-pentanediketiminate)(pyrrolecarbaldnbutyliminate) platinum (II);
(N,N'-dimethyl-2,4-pentanediketiminate)(pyrrolecarbaldsecbutyliminate) platinum (II);
(N,N'-dimethyl-2,4-pentanediketiminate)(pyrrolecarbaldisobutyliminate) platinum (II);
(N,N'-dimethyl-2,4-pentanediketiminate)(pyrrolecarbaldtertbutyliminate) platinum (II);
(N,N'-dimethyl-2,4-pentanediketiminate)(pyrrolecarbaldtrimethylsilyliminate) platinum (II);
(N,N'-diethyl-2,4-pentanediketiminate)(pyrrolecarbaldiminate) platinum (II);
(N,N'-diethyl-2,4-pentanediketiminate)(pyrrolecarbaldmethyliminate) platinum (II);
(N,N'-diethyl-2,4-pentanediketiminate)(pyrrolecarbaldethyliminate) platinum (II);
(N,N'-diethyl-2,4-pentanediketiminate)(pyrrolecarbaldisopropyliminate) platinum (II);
(N,N'-diethyl-2,4-pentanediketiminate)(pyrrolecarbaldpropyliminate) platinum (II);
(N,N'-diethyl-2,4-pentanediketiminate)(pyrrolecarbaldnbutyliminate) platinum (II);
(N,N'-diethyl-2,4-pentanediketiminate)(pyrrolecarbaldsecbutyliminate) platinum (II);
(N,N'-diethyl-2,4-pentanediketiminate)(pyrrolecarbaldisobutyliminate) platinum (II);
(N,N'-diethyl-2,4-pentanediketiminate)(pyrrolecarbaldtertbutyliminate) platinum (II);
(N,N'-diethyl-2,4-pentanediketiminate)(pyrrolecarbaldtrimethylsilyliminate) platinum (II);
(N,N'-diisopropyl-2,4-pentanediketiminate)(pyrrolecarbaldiminate) platinum (II);
(N,N'-diisopropyl-2,4-pentanediketiminate)(pyrrolecarbaldmethyliminate) platinum (II);
(N,N'-diisopropyl-2,4-pentanediketiminate)(pyrrolecarbaldethyliminate) platinum (II);
(N,N'-diisopropyl-2,4-pentanediketiminate)(pyrrolecarbaldisopropyliminate) platinum (II);
(N,N'-diisopropyl-2,4-pentanediketiminate)(pyrrolecarbaldpropyliminate) platinum (II);
(N,N'-diisopropyl-2,4-pentanediketiminate)(pyrrolecarbaldnbutyliminate) platinum (II);
(N,N'-diisopropyl-2,4-pentanediketiminate)(pyrrolecarbaldsecbutyliminate) platinum (II);
(N,N'-diisopropyl-2,4-pentanediketiminate)(pyrrolecarbaldisobutyliminate) platinum (II);
(N,N'-diisopropyl-2,4-pentanediketiminate)(pyrrolecarbaldtertbutyliminate) platinum (II);
(N,N'-diisopropyl-2,4-pentanediketiminate)(pyrrolecarbaldtrimethylsilyliminate) platinum (II);
(N,N'-dipropyl-2,4-pentanediketiminate)(pyrrolecarbaldiminate) platinum (II);
(N,N'-dipropyl-2,4-pentanediketiminate)(pyrrolecarbaldmethyliminate) platinum (II);
(N,N'-dipropyl-2,4-pentanediketiminate)(pyrrolecarbaldethyliminate) platinum (II);
(N,N'-dipropyl-2,4-pentanediketiminate)(pyrrolecarbaldisopropyliminate) platinum (II);
(N,N'-dipropyl-2,4-pentanediketiminate)(pyrrolecarbaldpropyliminate) platinum (II);
(N,N'-dipropyl-2,4-pentanediketiminate)(pyrrolecarbaldnbutyliminate) platinum (II);
(N,N'-dipropyl-2,4-pentanediketiminate)(pyrrolecarbaldsecbutyliminate) platinum (II);
(N,N'-dipropyl-2,4-pentanediketiminate)(pyrrolecarbaldisobutyliminate) platinum (II);
(N,N'-dipropyl-2,4-pentanediketiminate)(pyrrolecarbaldtertbutyliminate) platinum (II);
(N,N'-dipropyl-2,4-pentanediketiminate)(pyrrolecarbaldtrimethylsilyliminate) platinum (II);
(N,N'-di-tert-butyl-2,4-pentanediketiminate)(pyrrolecarbaldiminate) platinum (II);
(N,N'-di-tert-butyl-2,4-pentanediketiminate)(pyrrolecarbaldmethyliminate) platinum (II);
(N,N'-di-tert-butyl-2,4-pentanediketiminate)(pyrrolecarbaldethyliminate) platinum (II);
(N,N'-di-tert-butyl-2,4-pentanediketiminate)(pyrrolecarbaldisopropyliminate) platinum (II);
(N,N'-di-tert-butyl-2,4-pentanediketiminate)(pyrrolecarbaldpropyliminate) platinum (II);
(N,N'-di-tert-butyl-2,4-pentanediketiminate)(pyrrolecarbaldnbutyliminate) platinum (II);
(N,N'-di-tert-butyl-2,4-pentanediketiminate)(pyrrolecarbaldsecbutyliminate) platinum (II);
(N,N'-di-tert-butyl-2,4-pentanediketiminate)(pyrrolecarbaldisobutyliminate) platinum (II);
(N,N'-di-tert-butyl-2,4-pentanediketiminate)(pyrrolecarbaldtertbutyliminate) platinum (II);
(N,N'-di-tert-butyl-2,4-pentanediketiminate)(pyrrolecarbaldtrimethylsilyliminate) platinum (II);
(N,N'-diisopropylformamidinate)(pyrrolecarbaldiminate) platinum (II);
(N,N'-diisopropylformamidinate)(pyrrolecarbaldmethyliminate) platinum (II);
(N,N'-diisopropylformamidinate)(pyrrolecarbaldethyliminate) platinum (II);
(N,N'-diisopropylformamidinate)(pyrrolecarbaldisopropyliminate) platinum (II);
(N,N'-diisopropylformamidinate)(pyrrolecarbaldpropyliminate) platinum (II);
(N,N'-diisopropylformamidinate)(pyrrolecarbaldnbutyliminate) platinum (II);
(N,N'-diisopropylformamidinate)(pyrrolecarbaldsecbutyliminate) platinum (II);

(N,N'-diisopropylformamidinate)(pyrrolecarbaldisobutyliminate) platinum (II);
(N,N'-diisopropylformamidinate)(pyrrolecarbaldtertbutyliminate) platinum (II);
(N,N'-diisopropylformamidinate)(pyrrolecarbaldtrimethylsilyliminate) platinum (II);
(N,N'-diisopropylacetamidinate)(pyrrolecarbaldiminate) platinum (II);
(N,N'-diisopropylacetamidinate)(pyrrolecarbaldmethyliminate) platinum (II);
(N,N'-diisopropylacetamidinate)(pyrrolecarbaldethyliminate) platinum (II);
(N,N'-diisopropylacetamidinate)(pyrrolecarbaldisopropyliminate) platinum (II);
(N,N'-diisopropylacetamidinate)(pyrrolecarbaldpropyliminate) platinum (II);
(N,N'-diisopropylacetamidinate)(pyrrolecarbaldnbutyliminate) platinum (II);
(N,N'-diisopropylacetamidinate)(pyrrolecarbaldsecbutyliminate) platinum (II);
(N,N'-diisopropylacetamidinate)(pyrrolecarbaldisobutyliminate) platinum (II);
(N,N'-diisopropylacetamidinate)(pyrrolecarbaldtertbutyliminate) platinum (II);
(N,N'-diisopropylacetamidinate)(pyrrolecarbaldtrimethylsilyliminate) platinum (II);
(N,N'-diisopropyl-N,N'-dimethylguanidinate)(pyrrolecarbaldiminate) platinum (II);
(N,N'-diisopropyl-N,N'-dimethylguanidinate)(pyrrolecarbaldmethyliminate) platinum (II);
(N,N'-diisopropyl-N,N'-dimethylguanidinate)(pyrrolecarbaldethyliminate) platinum (II);
(N,N'-diisopropyl-N,N'-dimethylguanidinate)(pyrrolecarbaldisopropyliminate) platinum (II);
(N,N'-diisopropyl-N,N'-dimethylguanidinate)(pyrrolecarbaldpropyliminate) platinum (II);
(N,N'-diisopropyl-N,N'-dimethylguanidinate)(pyrrolecarbaldnbutyliminate) platinum (II);
(N,N'-diisopropyl-N,N'-dimethylguanidinate)(pyrrolecarbaldsecbutyliminate) platinum (II);
(N,N'-diisopropyl-N,N'-dimethylguanidinate)(pyrrolecarbaldisobutyliminate) platinum (II);
(N,N'-diisopropyl-N,N'-dimethylguanidinate)(pyrrolecarbaldtertbutyliminate) platinum (II);
(N,N'-diisopropyl-N,N'-dimethylguanidinate)(pyrrolecarbaldtrimethylsilyliminate) platinum (II);
(N,N'-2,4-pentanediketiminate)(pyrrolecarbaldiminate) ruthenium (II);
(N,N'-2,4-pentanediketiminate)(pyrrolecarbaldmethyliminate) ruthenium (II);
(N,N'-2,4-pentanediketiminate)(pyrrolecarbaldethyliminate) ruthenium (II);
(N,N'-2,4-pentanediketiminate)(pyrrolecarbaldisopropyliminate) ruthenium (II);
(N,N'-2,4-pentanediketiminate)(pyrrolecarbaldpropyliminate) ruthenium (II);
(N,N'-2,4-pentanediketiminate)(pyrrolecarbaldnbutyliminate) ruthenium (II);
(N,N'-2,4-pentanediketiminate)(pyrrolecarbaldsecbutyliminate) ruthenium (II);
(N,N'-2,4-pentanediketiminate)(pyrrolecarbaldisobutyliminate) ruthenium (II);
(N,N'-2,4-pentanediketiminate)(pyrrolecarbaldtertbutyliminate) ruthenium (II);
(N,N'-2,4-pentanediketiminate)(pyrrolecarbaldtrimethylsilyliminate) ruthenium (II);
(N,N'-dimethyl-2,4-pentanediketiminate)(pyrrolecarbaldiminate) ruthenium (II);
(N,N'-dimethyl-2,4-pentanediketiminate)(pyrrolecarbaldmethyliminate) ruthenium (II);
(N,N'-dimethyl-2,4-pentanediketiminate)(pyrrolecarbaldethyliminate) ruthenium (II);
(N,N'-dimethyl-2,4-pentanediketiminate)(pyrrolecarbaldisopropyliminate) ruthenium (II);
(N,N'-dimethyl-2,4-pentanediketiminate)(pyrrolecarbaldpropyliminate) ruthenium (II);
(N,N'-dimethyl-2,4-pentanediketiminate)(pyrrolecarbaldnbutyliminate) ruthenium (II);
(N,N'-dimethyl-2,4-pentanediketiminate)(pyrrolecarbaldsecbutyliminate) ruthenium (II);
(N,N'-dimethyl-2,4-pentanediketiminate)(pyrrolecarbaldisobutyliminate) ruthenium (II);
(N,N'-dimethyl-2,4-pentanediketiminate)(pyrrolecarbaldtertbutyliminate) ruthenium (II);
(N,N'-dimethyl-2,4-pentanediketiminate)(pyrrolecarbaldtrimethylsilyliminate) ruthenium (II);
(N,N'-diethyl-2,4-pentanediketiminate)(pyrrolecarbaldiminate) ruthenium (II);
(N,N'-diethyl-2,4-pentanediketiminate)(pyrrolecarbaldmethyliminate) ruthenium (II);
(N,N'-diethyl-2,4-pentanediketiminate)(pyrrolecarbaldethyliminate) ruthenium (II);
(N,N'-diethyl-2,4-pentanediketiminate)(pyrrolecarbaldisopropyliminate) ruthenium (II);
(N,N'-diethyl-2,4-pentanediketiminate)(pyrrolecarbaldpropyliminate) ruthenium (II);
(N,N'-diethyl-2,4-pentanediketiminate)(pyrrolecarbaldnbutyliminate) ruthenium (II);
(N,N'-diethyl-2,4-pentanediketiminate)(pyrrolecarbaldsecbutyliminate) ruthenium (II);
(N,N'-diethyl-2,4-pentanediketiminate)(pyrrolecarbaldisobutyliminate) ruthenium (II);
(N,N'-diethyl-2,4-pentanediketiminate)(pyrrolecarbaldtertbutyliminate) ruthenium (II);
(N,N'-diethyl-2,4-pentanediketiminate)(pyrrolecarbaldtrimethylsilyliminate) ruthenium (II);
(N,N'-diisopropyl-2,4-pentanediketiminate)(pyrrolecarbaldiminate) ruthenium (II);
(N,N'-diisopropyl-2,4-pentanediketiminate)(pyrrolecarbaldmethyliminate) ruthenium (II);
(N,N'-diisopropyl-2,4-pentanediketiminate)(pyrrolecarbaldethyliminate) ruthenium (II);
(N,N'-diisopropyl-2,4-pentanediketiminate)(pyrrolecarbaldisopropyliminate) ruthenium (II);
(N,N'-diisopropyl-2,4-pentanediketiminate)(pyrrolecarbaldpropyliminate) ruthenium (II);
(N,N'-diisopropyl-2,4-pentanediketiminate)(pyrrolecarbaldnbutyliminate) ruthenium (II);
(N,N'-diisopropyl-2,4-pentanediketiminate)(pyrrolecarbaldsecbutyliminate) ruthenium (II);
(N,N'-diisopropyl-2,4-pentanediketiminate)(pyrrolecarbaldisobutyliminate) ruthenium (II);
(N,N'-diisopropyl-2,4-pentanediketiminate)(pyrrolecarbaldtertbutyliminate) ruthenium (II);
(N,N'-diisopropyl-2,4-pentanediketiminate)(pyrrolecarbaldtrimethylsilyliminate) ruthenium (II);
(N,N'-dipropyl-2,4-pentanediketiminate)(pyrrolecarbaldiminate) ruthenium (II);
(N,N'-dipropyl-2,4-pentanediketiminate)(pyrrolecarbaldmethyliminate) ruthenium (II);
(N,N'-dipropyl-2,4-pentanediketiminate)(pyrrolecarbaldethyliminate) ruthenium (II);

(N,N'-dipropyl-2,4-pentanediketiminate)(pyrrolecarbaldisopropyliminate) ruthenium (II);
(N,N'-dipropyl-2,4-pentanediketiminate)(pyrrolecarbaldpropyliminate) ruthenium (II);
(N,N'-dipropyl-2,4-pentanediketiminate)(pyrrolecarbaldnbutyliminate) ruthenium (II);
(N,N'-dipropyl-2,4-pentanediketiminate)(pyrrolecarbaldsecbutyliminate) ruthenium (II);
(N,N'-dipropyl-2,4-pentanediketiminate)(pyrrolecarbaldisobutyliminate) ruthenium (II);
(N,N'-dipropyl-2,4-pentanediketiminate)(pyrrolecarbaldtertbutyliminate) ruthenium (II);
(N,N'-dipropyl-2,4-pentanediketiminate)(pyrrolecarbaldtrimethylsilyliminate) ruthenium (II);
(N,N'-di-tert-butyl-2,4-pentanediketiminate)(pyrrolecarbaldiminate) ruthenium (II);
(N,N'-di-tert-butyl-2,4-pentanediketiminate)(pyrrolecarbaldmethyliminate) ruthenium (II);
(N,N'-di-tert-butyl-2,4-pentanediketiminate)(pyrrolecarbaldethyliminate) ruthenium (II);
(N,N'-di-tert-butyl-2,4-pentanediketiminate)(pyrrolecarbaldisopropyliminate) ruthenium (II);
(N,N'-di-tert-butyl-2,4-pentanediketiminate)(pyrrolecarbaldpropyliminate) ruthenium (II);
(N,N'-di-tert-butyl-2,4-pentanediketiminate)(pyrrolecarbaldnbutyliminate) ruthenium (II);
(N,N'-di-tert-butyl-2,4-pentanediketiminate)(pyrrolecarbaldsecbutyliminate) ruthenium (II);
(N,N'-di-tert-butyl-2,4-pentanediketiminate)(pyrrolecarbaldisobutyliminate) ruthenium (II);
(N,N'-di-tert-butyl-2,4-pentanediketiminate)(pyrrolecarbaldtertbutyliminate) ruthenium (II);
(N,N'-di-tert-butyl-2,4-pentanediketiminate)(pyrrolecarbaldtrimethylsilyliminate) ruthenium (II);
(N,N'-diisopropylformamidinate)(pyrrolecarbaldiminate) ruthenium (II);
(N,N'-diisopropylformamidinate)(pyrrolecarbaldmethyliminate) ruthenium (II);
(N,N'-diisopropylformamidinate)(pyrrolecarbaldethyliminate) ruthenium (II);
(N,N'-diisopropylformamidinate)(pyrrolecarbaldisopropyliminate) ruthenium (II);
(N,N'-diisopropylformamidinate)(pyrrolecarbaldpropyliminate) ruthenium (II);
(N,N'-diisopropylformamidinate)(pyrrolecarbaldnbutyliminate) ruthenium (II);
(N,N'-diisopropylformamidinate)(pyrrolecarbaldsecbutyliminate) ruthenium (II);
(N,N'-diisopropylformamidinate)(pyrrolecarbaldisobutyliminate) ruthenium (II);
(N,N'-diisopropylformamidinate)(pyrrolecarbaldtertbutyliminate) ruthenium (II);
(N,N'-diisopropylformamidinate)(pyrrolecarbaldtrimethylsilyliminate) ruthenium (II);
(N,N'-diisopropylacetamidinate)(pyrrolecarbaldiminate) ruthenium (II);
(N,N'-diisopropylacetamidinate)(pyrrolecarbaldmethyliminate) ruthenium (II);
(N,N'-diisopropylacetamidinate)(pyrrolecarbaldethyliminate) ruthenium (II);
(N,N'-diisopropylacetamidinate)(pyrrolecarbaldisopropyliminate) ruthenium (II);
(N,N'-diisopropylacetamidinate)(pyrrolecarbaldpropyliminate) ruthenium (II);
(N,N'-diisopropylacetamidinate)(pyrrolecarbaldnbutyliminate) ruthenium (II);
(N,N'-diisopropylacetamidinate)(pyrrolecarbaldsecbutyliminate) ruthenium (II);
(N,N'-diisopropylacetamidinate)(pyrrolecarbaldisobutyliminate) ruthenium (II);
(N,N'-diisopropylacetamidinate)(pyrrolecarbaldtertbutyliminate) ruthenium (II);
(N,N'-diisopropylacetamidinate)(pyrrolecarbaldtrimethylsilyliminate) ruthenium (II);
(N,N'-diisopropyl-N,N'-dimethylguanidinate)(pyrrolecarbaldiminate) ruthenium (II);
(N,N'-diisopropyl-N,N'-dimethylguanidinate)(pyrrolecarbaldmethyliminate) ruthenium (II);
(N,N'-diisopropyl-N,N'-dimethylguanidinate)(pyrrolecarbaldethyliminate) ruthenium (II);
(N,N'-diisopropyl-N,N'-dimethylguanidinate)(pyrrolecarbaldisopropyliminate) ruthenium (II);
(N,N'-diisopropyl-N,N'-dimethylguanidinate)(pyrrolecarbaldpropyliminate) ruthenium (II);
(N,N'-diisopropyl-N,N'-dimethylguanidinate)(pyrrolecarbaldnbutyliminate) ruthenium (II);
(N,N'-diisopropyl-N,N'-dimethylguanidinate)(pyrrolecarbaldsecbutyliminate) ruthenium (II);
(N,N'-diisopropyl-N,N'-dimethylguanidinate)(pyrrolecarbaldisobutyliminate) ruthenium (II);
(N,N'-diisopropyl-N,N'-dimethylguanidinate)(pyrrolecarbaldtertbutyliminate) ruthenium (II); and
(N,N'-diisopropyl-N,N'-dimethylguanidinate)(pyrrolecarbaldtrimethylsilyliminate) ruthenium (II).

13. The process of claim 12, wherein the metalloid-containing precursor is selected from the group consisting of:
(N,N'-diisopropylacetamidinate)(pyrrolecarbaldisopropyliminate) palladium (II);
(N,N'-diisopropylacetamidinate)(pyrrolecarbaldisopropyliminate) platinum(II); and
(N,N'-diisopropylacetamidinate)(pyrrolecarbaldisopropyliminate) ruthenium(II).

14. The process of claim 12, wherein the metalloid-containing precursor is (N,N'-diisopropylacetamidinate)(pyrrolecarbaldisopropyliminate) palladium (II).

15. The process of claim 12, wherein the metalloid-containing precursor is (N,N'-diisopropylacetamidinate)(pyrrolecarbaldisopropyliminate) platinum(II).

16. The process of claim 12, wherein the metalloid-containing precursor is (N,N'-diisopropylacetamidinate)(pyrrolecarbaldisopropyliminate) ruthenium(II).

17. The precursor of claim 1, wherein the precursor is (N,N'-diisopropylacetamidinate)(pyrrolecarbaldisopropyliminate) palladium (II).

18. The precursor of claim 1, wherein the precursor is (N,N'-diisopropylacetamidinate)(pyrrolecarbaldisopropyliminate) platinum(II).

19. The precursor of claim 1, wherein the precursor is (N,N'-diisopropylacetamidinate)(pyrrolecarbaldisopropyliminate) ruthenium(II).

* * * * *